(12) United States Patent
Murray et al.

(10) Patent No.: US 11,771,475 B2
(45) Date of Patent: Oct. 3, 2023

(54) SYSTEMS AND METHODS FOR SURGICAL PROCEDURES USING BAND CLAMP IMPLANTS AND TENSIONING INSTRUMENTS

(71) Applicant: GLOBUS MEDICAL, INC., Audubon, PA (US)

(72) Inventors: Patrick Murray, Collegeville, PA (US); John LaColla, West Chester, PA (US); Jeff Nichols, Medford, NJ (US)

(73) Assignee: Globus Medical, Inc., Audubon, PA (US)

( * ) Notice: Subject to any disclaimer, the term of this patent is extended or adjusted under 35 U.S.C. 154(b) by 10 days.

(21) Appl. No.: 17/465,252

(22) Filed: Sep. 2, 2021

(65) Prior Publication Data
US 2022/0104853 A1    Apr. 7, 2022

Related U.S. Application Data

(63) Continuation-in-part of application No. 17/072,192, filed on Oct. 16, 2020, and a continuation-in-part of application No. 17/064,833, filed on Oct. 7, 2020, now Pat. No. 11,534,222.

(51) Int. Cl.
*A61B 17/70* (2006.01)
*A61B 17/00* (2006.01)

(52) U.S. Cl.
CPC ...... *A61B 17/7053* (2013.01); *A61B 17/7083* (2013.01); *A61B 2017/00407* (2013.01)

(58) Field of Classification Search
CPC .......................... A61B 17/842; A61B 17/7053
See application file for complete search history.

(56) References Cited

U.S. PATENT DOCUMENTS

| | | |
|---|---|---|
| 3,507,270 A | 4/1970 | Ferrier |
| 4,834,092 A | 5/1989 | Alexson et al. |
| 5,002,555 A | 3/1991 | Petersen |
| 5,201,749 A | 4/1993 | Sachse et al. |
| 5,207,697 A | 5/1993 | Carusillo et al. |
| 5,235,261 A | 8/1993 | Philipp |
| 5,263,972 A | 11/1993 | Evans et al. |
| 5,439,472 A | 8/1995 | Evans et al. |
| 5,697,158 A | 12/1997 | Klinzing et al. |
| 5,788,697 A | 8/1998 | Kilpela et al. |
| 6,013,991 A | 1/2000 | Philipp |
| 6,025,683 A | 2/2000 | Philipp et al. |
| 6,042,585 A | 3/2000 | Norman |
| 6,113,618 A | 9/2000 | Nic |

(Continued)

FOREIGN PATENT DOCUMENTS

| | | |
|---|---|---|
| CN | 103505259 A | 1/2014 |
| DE | 202008017023 U1 | 4/2009 |

(Continued)

*Primary Examiner* — Tessa M Matthews

(57) ABSTRACT

Implants, systems, and methods for securing a flexible band, thereby providing a desired correction to the spine. The implant may secure the flexible band to patient anatomy without the use of pedicle screws or spinal rods. The implant may include a locking member configured to secure the band. The band may be looped around bony anatomy and tensioned to achieve correction and provide fixation as an alternative to pedicle screws and spinal rods during spinal deformity surgery.

18 Claims, 66 Drawing Sheets

(56) References Cited

U.S. PATENT DOCUMENTS

| | | |
|---|---|---|
| 6,482,208 B1 | 11/2002 | Ahrend et al. |
| 6,689,140 B2 | 2/2004 | Cohen |
| 6,912,790 B2 | 7/2005 | James et al. |
| 6,949,110 B2 | 9/2005 | Ark et al. |
| 6,960,894 B2 | 11/2005 | Carusillo et al. |
| 7,400,107 B2 | 7/2008 | Schneider et al. |
| RE40,848 E | 7/2009 | Pitzen et al. |
| 7,691,106 B2 | 4/2010 | Schenberger et al. |
| 8,029,510 B2 | 10/2011 | Hoegerle |
| 8,100,912 B2 | 1/2012 | Marietta |
| 8,162,946 B2 | 4/2012 | Baccelli et al. |
| 8,257,367 B2 | 9/2012 | Bryant et al. |
| 8,323,285 B2 | 12/2012 | Walen et al. |
| 8,323,318 B2 | 12/2012 | Baccelli et al. |
| 8,469,966 B2 | 6/2013 | Allen et al. |
| 8,621,967 B2 | 1/2014 | Doumani |
| 8,672,943 B2 | 3/2014 | Fisher et al. |
| 8,728,083 B2 | 5/2014 | Baccelli et al. |
| 8,814,910 B2 | 8/2014 | Baccelli et al. |
| 8,945,188 B2 | 2/2015 | Rezach et al. |
| 9,078,671 B2 | 7/2015 | Beale et al. |
| 9,095,380 B2 | 8/2015 | Mir et al. |
| 9,204,902 B2 | 12/2015 | Belliard et al. |
| 9,204,903 B2 | 12/2015 | Belliard et al. |
| 9,314,275 B2 | 4/2016 | Clement et al. |
| 9,333,019 B2 | 5/2016 | Khosla et al. |
| 9,393,051 B2 | 7/2016 | Baccelli et al. |
| 9,439,655 B2 | 9/2016 | Cosgrove et al. |
| 9,451,976 B2 | 9/2016 | Schneider et al. |
| 9,510,862 B2 | 12/2016 | Montello et al. |
| 9,675,386 B2 | 6/2017 | Akbarnia et al. |
| 9,687,257 B2 | 6/2017 | Straslicka et al. |
| 9,924,954 B2 | 3/2018 | Guo et al. |
| 9,924,976 B2 | 3/2018 | Simpson et al. |
| 9,949,768 B2 | 4/2018 | Rathburn et al. |
| 10,064,656 B2 | 9/2018 | Mundis, Jr. et al. |
| 10,149,686 B2 | 12/2018 | Anderson |
| 10,231,742 B2 | 3/2019 | Lo et al. |
| 10,238,432 B2 | 3/2019 | Carruth et al. |
| 10,245,079 B2 | 4/2019 | Sournac et al. |
| 10,251,651 B2 | 4/2019 | Carusillo |
| 10,278,710 B2 | 5/2019 | Walen et al. |
| 10,307,186 B2 | 6/2019 | Schafer et al. |
| 10,342,553 B2 | 7/2019 | Gilhooley |
| 10,363,617 B2 | 7/2019 | Desoutter et al. |
| 10,420,590 B2 | 9/2019 | Le Couedic et al. |
| 10,433,879 B2 | 10/2019 | Pasquet et al. |
| 10,470,803 B2 | 11/2019 | Akbarnia et al. |
| 10,512,486 B2 | 12/2019 | Larroque-Lahitette |
| 10,517,610 B2 | 12/2019 | Philipp et al. |
| 10,543,023 B2 | 1/2020 | Le Couedic et al. |
| 10,687,823 B2 | 6/2020 | MacanTuile et al. |
| 10,687,824 B2 | 6/2020 | Shiels et al. |
| 2006/0217729 A1 | 9/2006 | Eskridge et al. |
| 2006/0271045 A1 | 11/2006 | Hubbard et al. |
| 2009/0248077 A1 | 10/2009 | Johns |
| 2011/0160772 A1 | 6/2011 | Arcenio et al. |
| 2012/0271354 A1 | 10/2012 | Baccelli et al. |
| 2013/0072983 A1* | 3/2013 | Lindquist ........... A61B 17/7032 |
| | | 606/279 |
| 2014/0243905 A1 | 8/2014 | Cavallazzi et al. |
| 2016/0000449 A1 | 1/2016 | Aman et al. |
| 2016/0242819 A1 | 8/2016 | Simpson et al. |
| 2018/0153591 A1 | 6/2018 | Schafer et al. |
| 2018/0221073 A1* | 8/2018 | Cremer ................ A61B 17/842 |
| 2018/0228516 A1 | 8/2018 | Armstrong et al. |
| 2019/0046244 A1 | 2/2019 | Nguyen et al. |
| 2019/0343537 A1 | 11/2019 | Fennessy et al. |
| 2019/0343568 A1 | 11/2019 | Childers et al. |
| 2020/0038040 A1 | 2/2020 | Mahaffey |
| 2020/0237411 A1 | 7/2020 | Jacobs et al. |
| 2021/0236175 A1* | 8/2021 | Hubbard ................ A61B 17/82 |

FOREIGN PATENT DOCUMENTS

| | | |
|---|---|---|
| DE | 102008062880 A1 | 6/2010 |
| DE | 102008063239 A1 | 6/2010 |
| EP | 2047813 A1 | 4/2009 |
| FR | 3022449 A1 | 12/2015 |
| JP | 8505304 A | 6/1996 |
| JP | 2004512899 A | 4/2004 |
| JP | 2010000352 A | 1/2010 |
| JP | 2011500120 A | 1/2011 |
| NO | 0238063 A2 | 5/2002 |
| WO | 9944526 A1 | 9/1999 |
| WO | 2009004347 A1 | 1/2009 |
| WO | 2012151122 A1 | 11/2012 |
| WO | 2012176096 A1 | 12/2012 |
| WO | 2013016472 A1 | 1/2013 |
| WO | 2019236701 A1 | 12/2019 |
| WO | 2020072511 A1 | 4/2020 |
| WO | 2021144128 A1 | 7/2021 |

* cited by examiner

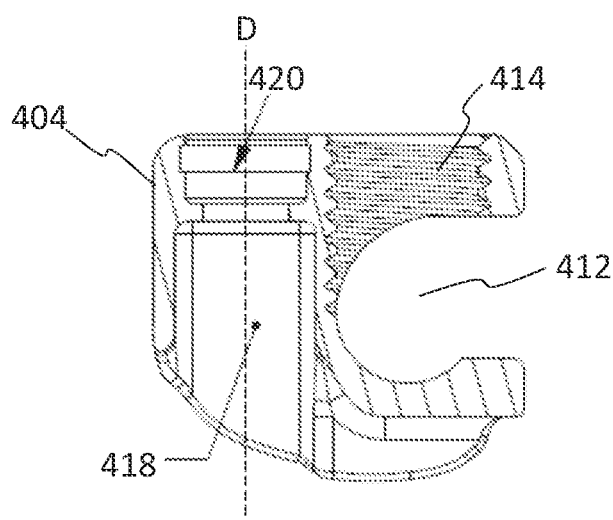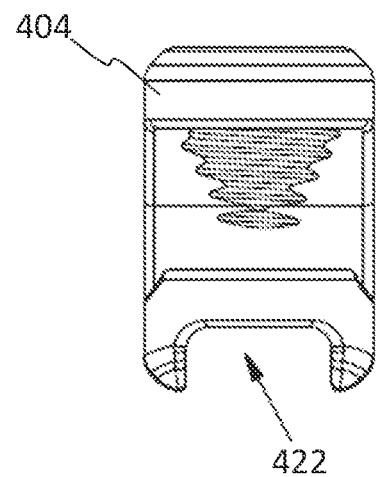
FIG. 42A  FIG. 42B
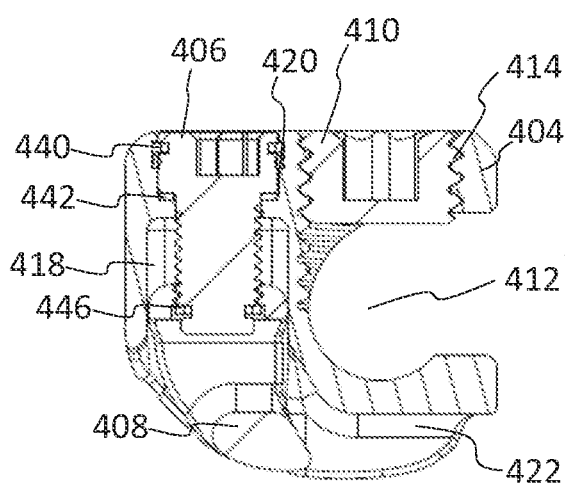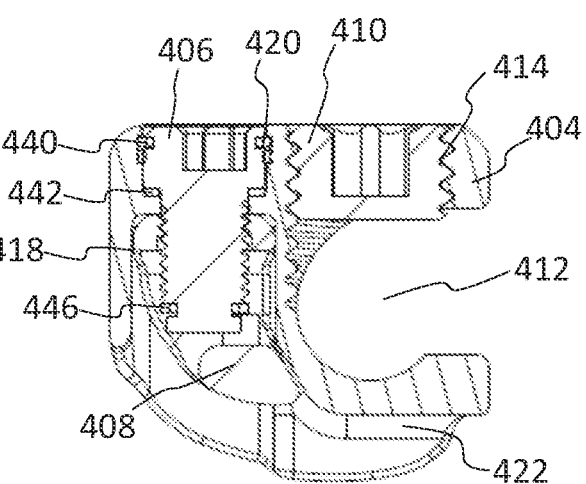
FIG. 42C  FIG. 42D

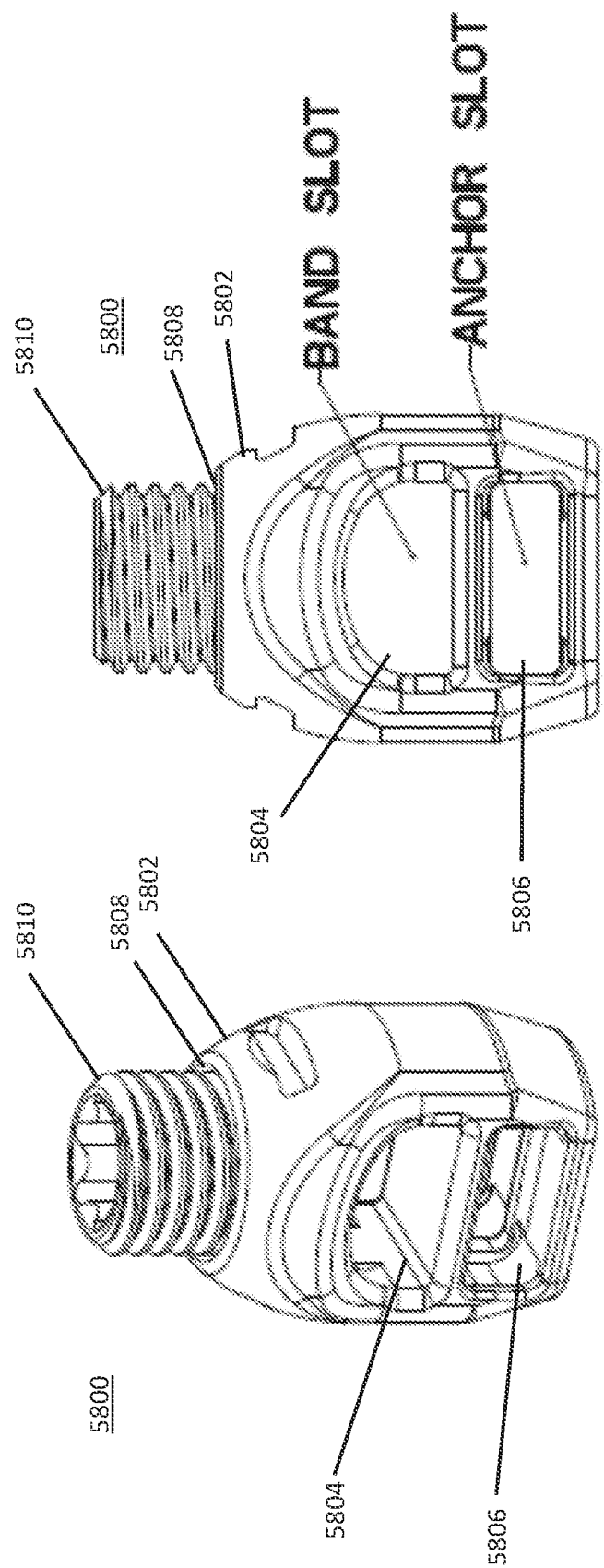

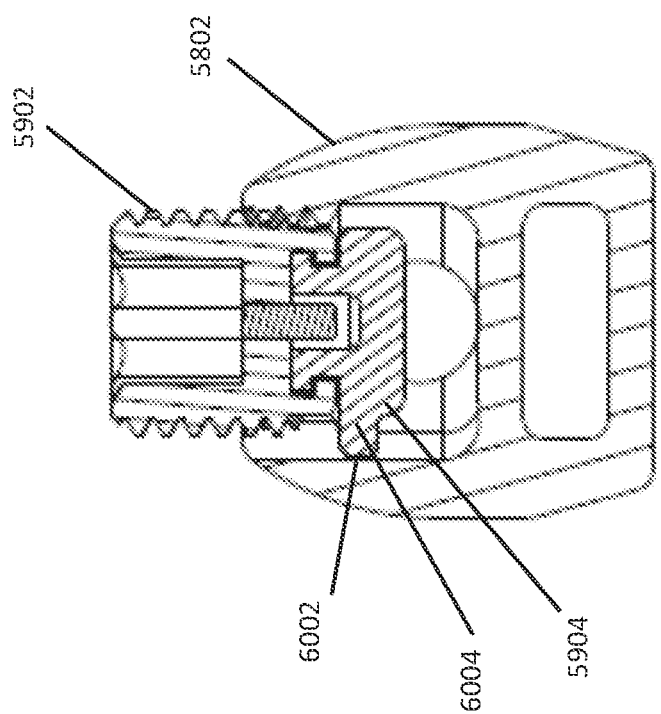
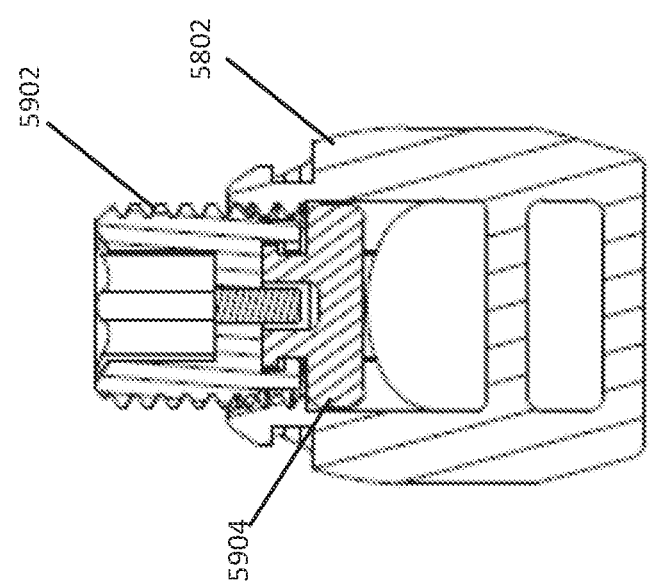
FIG. 60B
FIG. 60A

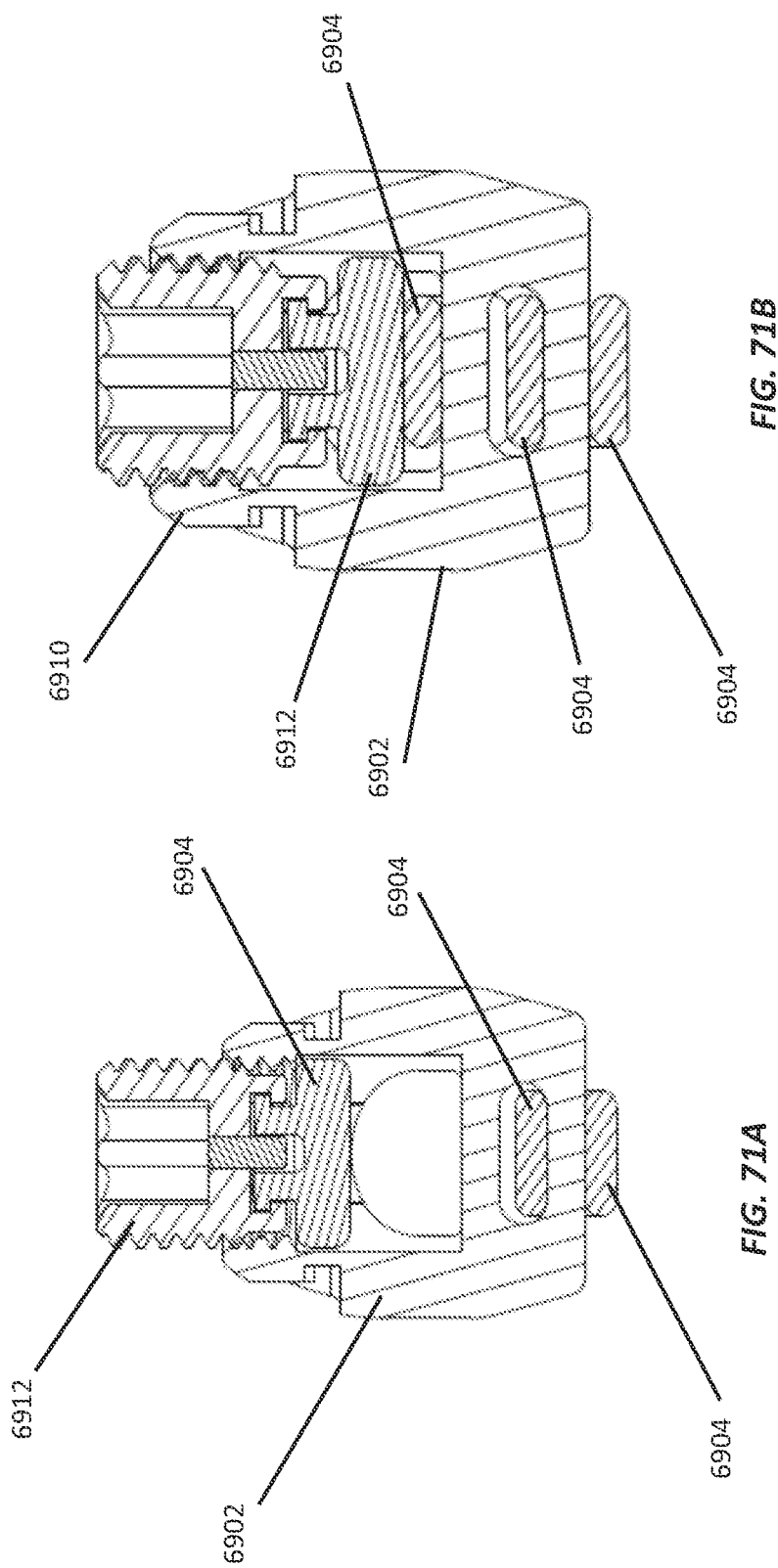

SYSTEMS AND METHODS FOR SURGICAL PROCEDURES USING BAND CLAMP IMPLANTS AND TENSIONING INSTRUMENTS

CROSS-REFERENCE TO RELATED APPLICATION(S)

This application is a continuation-in-part of U.S. patent application Ser. No. 17/072,192, filed Oct. 16, 2020. This application is also a continuation-in-part of U.S. patent application Ser. No. 17/064,833, filed Oct. 7, 2020. The entire contents of each of which is hereby incorporated by reference in its entirety for all purposes.

FIELD OF THE INVENTION

The present application relates generally to surgical devices and systems, and more particularly, to band clamp implants and tensioning instruments for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing screws, hooks and/or clamps to one or more vertebrae and connecting the screws, hooks and/or clamps to an elongate spinal rod that stabilizes members of the spine.

In addition, instability of the first and second cervical vertebrae is a common pathology caused by traumatic injury. While posterior fixation of the cervical spine is most commonly performed using screw fixation, there are times when it is advantageous to perform posterior cervical fixation using non-screw based techniques, including patients with low bone mineral density or fractured anatomy. In these cases, flexible bands may be used to achieve correction and provide fixation. The bands are wrapped around bony anatomy and then tensioned to provide fixation and promote healing. The same technique is commonly used with metal wires at C1-C2. However, metal wires have the potential to wear through bone or loosen over time leading to neurological injury.

Flexible bands may be used to achieve correction and provide fixation as an alternative and/or supplement to pedicle screws during spinal deformity surgery. The bands may be wrapped around bony anatomy and then a force may be applied to translate the spine to the spinal rod. Correction of the spinal deformity may be achieved and held by application of tension to the flexible band. Bands may be advantageous, for example, in pediatric and neuromuscular deformity cases due to the high prevalence of weak bone and dysmorphic vertebrae which make pedicle screw placement difficult or impossible. There exists a need for improved band clamp implants for securing the band to the bone.

SUMMARY OF THE INVENTION

According to some examples of the concepts described herein, a band clamp implant assembly may be provided. The band clamp assembly may include a band clamp having a main body, a locking member, a band slot, and an anchor slot. The main body may further include a mating recess. The band clamp assembly may also include a flexible band having a first end, a second end, and a middle portion therebetween. A leader may be attached to the first end, an anchor may be attached to the second end, and the middle portion may be is configured to contact bone. The anchor is configured to engage the mating recess. The leader is configured to loop around patient anatomy and pass through the band slot, and the threaded locking member is configured to lock the flexible band in band clamp.

According to other examples of the concepts described herein, a system for fixating adjacent vertebral bodies may be provided. The system may include a band clamp having a main body, a locking member, a band slot, and an anchor slot. The main body may include a mating recess. The system may also include a flexible band having a first end, a second end, and a middle portion therebetween. A leader may be attached to the first end, an anchor may be attached to the second end, and the middle portion may be configured to contact bone. The anchor may be configured to engage the mating recess. The leader may be configured to loop around patient anatomy and pass through the band slot. The threaded locking member may be configured to lock the flexible band in band clamp. The system may further include a tensioning instrument to provide tension to the flexible band prior to locking the flexible band in the band clamp.

Also provided are kits including implants of varying types and sizes, rods, tensioner instruments, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 42A-42D show cross-sectional views of the implant;

FIGS. 58A and 58B show an exemplary embodiment of a band clamp consistent with the principles of the present disclosure.

FIGS. 60A and 60B show an exemplary embodiment of a band clamp consistent with the principles of the present disclosure.

FIGS. 71A and 71B show cross-section view of an exemplary embodiment of a band clamp system consistent with the principles of the present disclosure.

DETAILED DESCRIPTION OF THE INVENTION

Figure 1:
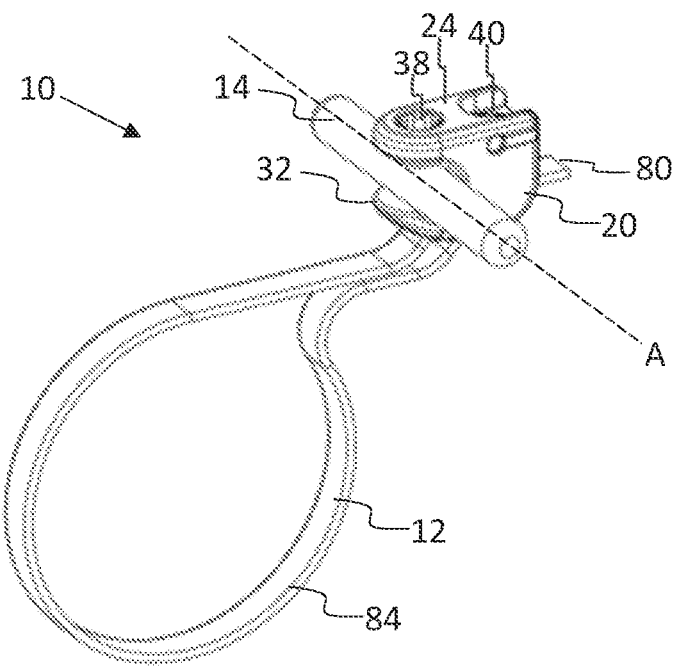
FIG. 1 shows a perspective view of a band clamp assembly with a band clamp implant securing a flexible band and spinal rod according to one embodiment.

Embodiments of the disclosure are generally directed to implants, systems, and methods for securing the flexible band to bone. Specifically, embodiments are directed to implants and systems configured to achieve correction and provide fixation as an alternative and/or supplement to pedicle screws during spinal deformity surgery.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

Referring now to FIGS. 1-9, a band clamp implant assembly or system 10 is shown according to one embodiment. The implant system 10 is configured to secure an elongate member, cable, tether, cord, or band 12 to a spinal rod 14. The band 12 may be a flexible member configured to be wrapped around bony anatomy or a portion of the spine, such as the lamina or transverse process, for example. The implant assembly 10 may engage with an elongate member, such as a spinal rod 14, to provide fixation between vertebrae. The flexible band 12 may be used as the primary fixation point at a particular spinal level when the placement of pedicle screws is difficult or impossible. Alternatively, the flexible band 12 may be used in conjunction with pedicle screws at a particular level to provide additional fixation. Although described with reference to the spine, it will be appreciated that the implants and systems described herein may be applied to other orthopedic locations and applications, such as trauma.

The flexible band 12 may be able to adapt to complex anatomies, such as severe spinal deformities. The assembly 10 allows the surgeon to achieve correction and fixation of a spinal deformity by securing the flexible band 12 to the spinal rod 14. This technique may be advantageous in pediatric and neuromuscular deformity cases when traditional pedicle screw fixation is compromised or not possible due to the presence of weak bone or dysmorphic vertebrae. Before or after the implant assembly 10 is affixed to bone and/or secured to bone by looping the band 12 around the bony anatomy, correction of the spinal deformity may be achieved and held by the application of tension to the flexible band 12.

The band 12 may be comprised of polyethylene terephthalates (PET), polyethylenes (e.g., ultrahigh molecular weight polyethylene or UHMWPE), polypropylenes, silk, polyamides, polyesters, polyacrylonitriles, silk cottons, combinations thereof, or other suitable biocompatible materials. The band 12 may be generally round, oval, or flat/tape geometry. The band 12 may transition from one geometry to another (e.g., a round to flat geometry or vice versa). If desired, the band 12 may be fully radiolucent or may have one or more marker strands that are designed to show up on fluoroscopy.

Figure 2:
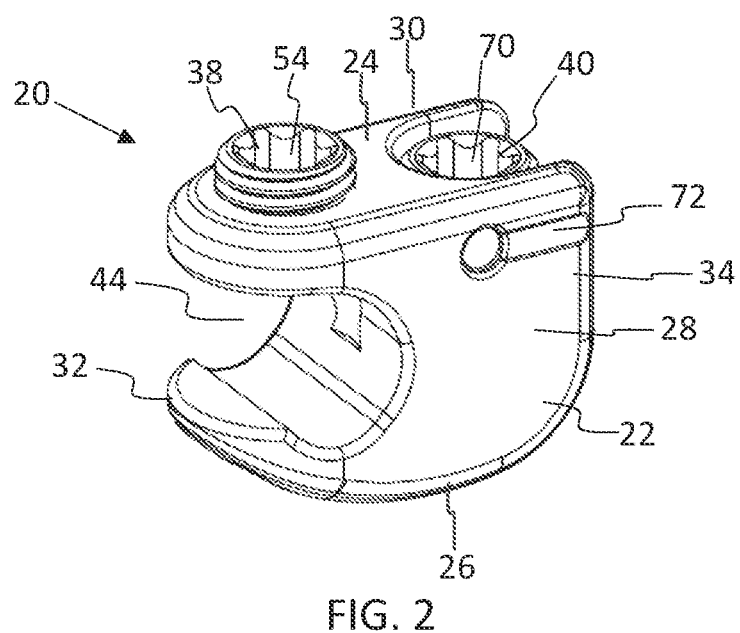
FIG. 2 is a perspective view of the band clamp implant shown in FIG. 1.

With emphasis on FIGS. 1 and 2, the implant assembly 10 includes a band clamp implant 20 capable of securing the flexible band 12 to the spinal rod 14. The band clamp implant 20 has a main body 22 including an upper surface 24, a lower surface 26, first and second opposed side surfaces 28, 30, a nose or front surface 32, and a back or rear surface 34. For example, the upper surface 24 and side surfaces 28, 30 may be generally flat or planar and the lower and back surfaces 26, 34 may be generally rounded or convex.

Figure 3:
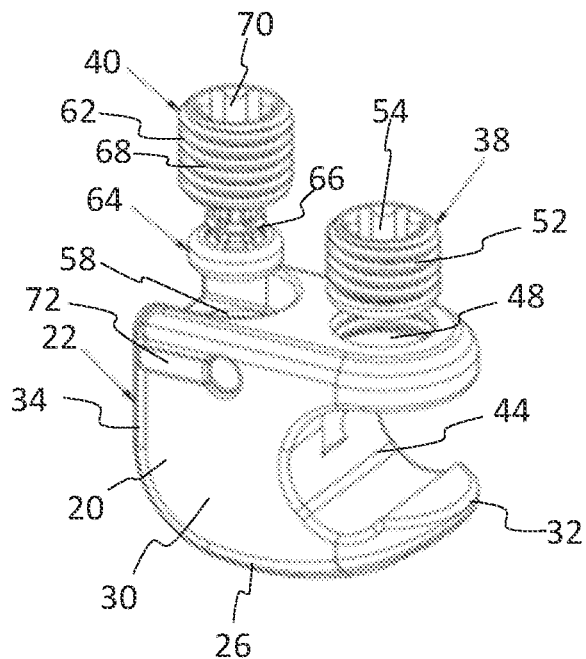
FIG. 3 is an exploded view of the band clamp implant.
Figure 4:
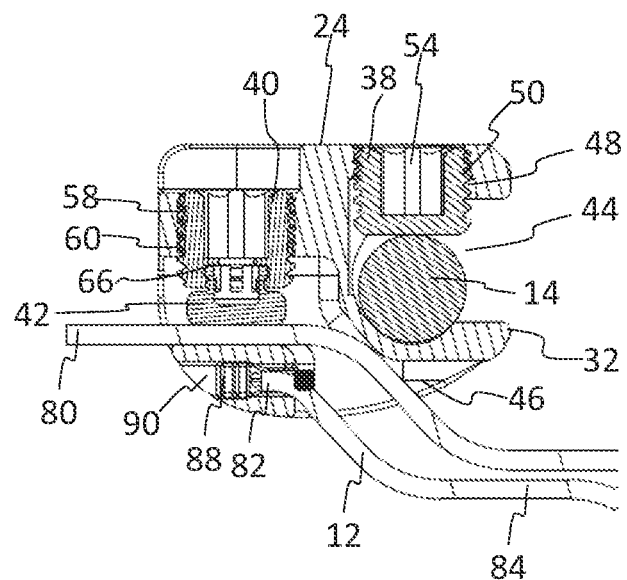
FIG. 4 shows a cross-sectional view of the flexible band secured in the band clamp implant.

As shown in FIGS. 3 and 4, the band clamp implant 20 includes a main body 22, a first locking member 38 configured to secure the rod 14, and a second locking member 40 with a saddle 64 configured to secure the band 12. With emphasis on FIG. 6, the main body 22 of the clamp 20 defines a first opening, recess, or rod slot 44 sized and dimensioned to accept the spinal rod 14 and a separate second opening or band slot 46 configured to accept the flexible band 12. The rod slot 44 may be recessed into the front surface 32 of the implant 20 and may define a generally c-shaped recess sized and dimensioned to receive the rod 14. The band slot 46 may extend from the lower surface 26 to the rear surface 34 of the implant 20. The band slot 46 may be stepped such that a first portion rises up from the lower surface 26 and a second portion runs over to the back surface 34. The band slot 46 is located beneath the rod slot 44 and is oriented perpendicular to a long axis A of the spinal rod 12.

The main body 22 has a first hole 48 in fluid communication with the rod slot 44. The first hole 48 may include a threaded portion 50 around an inner periphery of the hole 48. The first locking member 38 is positionable within the first hole 48, and when in a downward position, a bottom surface of the locking member 38 is configured to contact and secure the spinal rod 14 within the main body 22 of the implant 20. The first locking member 30 may include a threaded portion 52 around an outer surface, which is configured to threadedly mate with the first hole 48. The first locking member 30 may define an instrument recess 54 in an upper surface of the first locking member 30 configured to be engaged by an instrument, such as a driver, for rotating the locking member 38 into the locked position.

The main body 22 has a second hole 58 in fluid communication with the band slot 46. The hole axis of the second hole 58 may be generally parallel to the hole axis of the first hole 48. The second hole 58 may include a threaded portion 60 around an inner periphery of the hole 58. As shown in FIG. 4, the second locking member 40 may be positioned within the second hole 58 to secure the flexible band 12 within the band slot 46. The second locking member 40 may include a fastener or set screw 62 and a saddle 64. The set screw 62 and saddle 64 may be attachable to one another. The set screw 62 is able rotate independently of the saddle 64. The saddle 64 may define a ring or cylindrical body, and an upper surface of the saddle 64 may include one or more tabs or prongs 66 extending upwardly and/or outwardly. The prongs 66 may mate with a corresponding recess or groove within the lower surface of the set screw 62 to thereby connect the saddle 64 to the set screw 62. The prongs 66 on the saddle 64 may flex inward when pressed into the set screw 62 and snap back to its original shape when it reaches the groove in the set screw 62. The set screw 62 may include a threaded portion 68 around an outer surface, which is configured to threadedly mate with the second hole 58. The set screw 62 may define an instrument recess 70 in an upper surface configured to be engaged by an instrument, such as a driver, for rotating the set screw 62 and moving the locking member 40 into the locked position.

When the second locking member 40 is in a downward position, a bottom surface of the saddle 64 is configured to contact and secure the band 12 within the main body 22 of the implant 20. The set screw 62 and saddle 64 are able to travel up and down within the second threaded hole 58. The travel of the set screw 62 is such that the saddle 64 may reversibly interfere with the band slot 46. In a downward position, the saddle 64 is configured to press against the band 12, thereby locking the band 12 in position. For example, a free portion of the flexible band 12 may be locked to the band clamp 20 by tightening the set screw 62, which forces the bottom of the saddle 64 into contact with the flexible band 12. The flexible band 12 is then locked between the saddle 64 and the main body 22.

The main body 22 of the band clamp 20 may include one or more engagement recesses 72 for engagement with an insertion and/or tensioning instrument. For example, two opposed engagement recesses 72 may be defined within the side surfaces 28, 30, near the rear 34 of the implant 20. Each of the engagement recesses 72 may include a slot terminating in a circular divot, for example. It will be appreciated that other suitable engagement features may be used to temporarily couple the implant 20 to an instrument, such as inserter or tensioner.

Figure 5A:
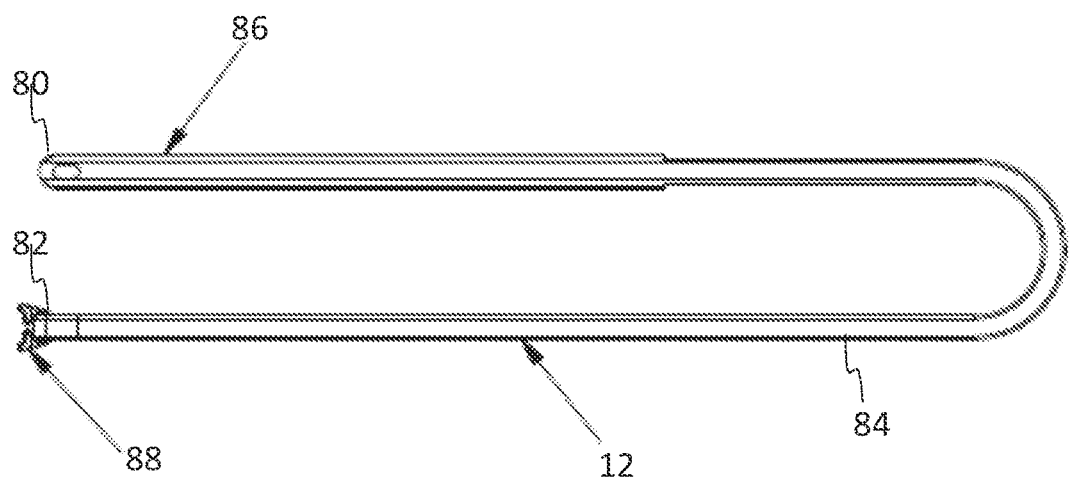
FIGS. 5A-5B show an embodiment of a flexible band and a close-up view of an anchor at the end of the flexible band.
Figure 6:
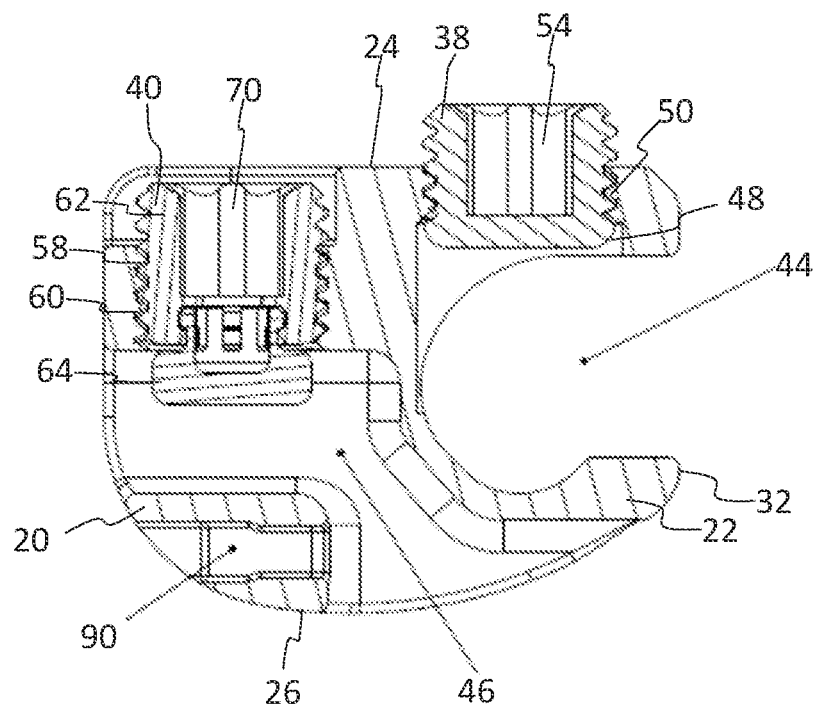
FIG. 6 is a side cross-sectional view of the band clamp implant.
Figure 7:
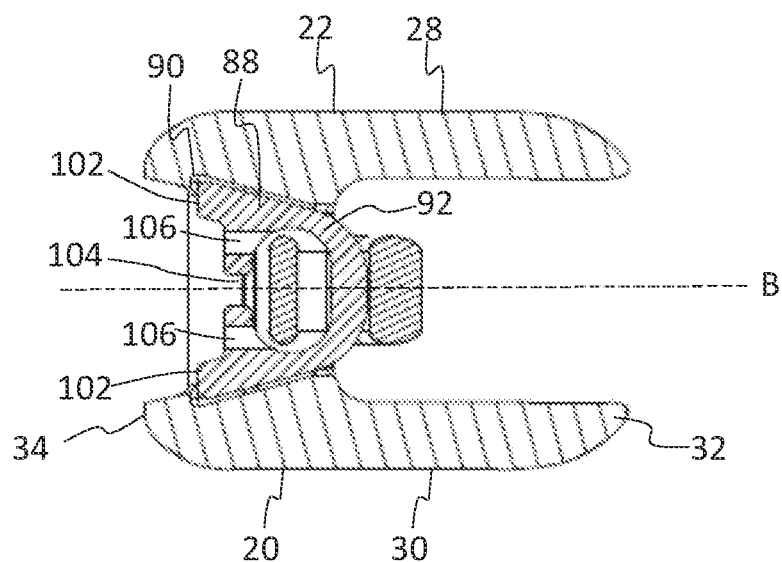
FIG. 7 is a top cross-sectional view of the anchor engaged with the band clamp implant.

With emphasis on FIG. 5A, the flexible band 12 may initially extend from a first free end 80 to an opposite free end 82 with a middle portion 84 in between. The middle portion 84 of the flexible band 12 is configured to contact and/or loop around bone. The first free end 80 of the flexible band 12 may be attached to a leader 86. The leader 86 may be a malleable leader configured to be fed around anatomy to wrap the flexible band 12 around the anatomy to be fixated. The second free end 82 of the flexible band 12 may be attached to an anchor 88. The anchor 88 may have a geometry such that the anchor 88 may be engaged with a mating recess 90 in the main body 22 of the band clamp 20. As shown in FIG. 6, the mating recess 90 may be located beneath the band slot 46. The entry of the mating recess 90 may be near the rear 34 of the implant 20 and the exit of the mating recess 90 may be into the band slot 46 near the bottom 26 of the implant 20. The geometry of the mating recess 90 is sized and dimensioned such that the anchor 88 is receivable and securable within the recess 90.

Figure 5B:
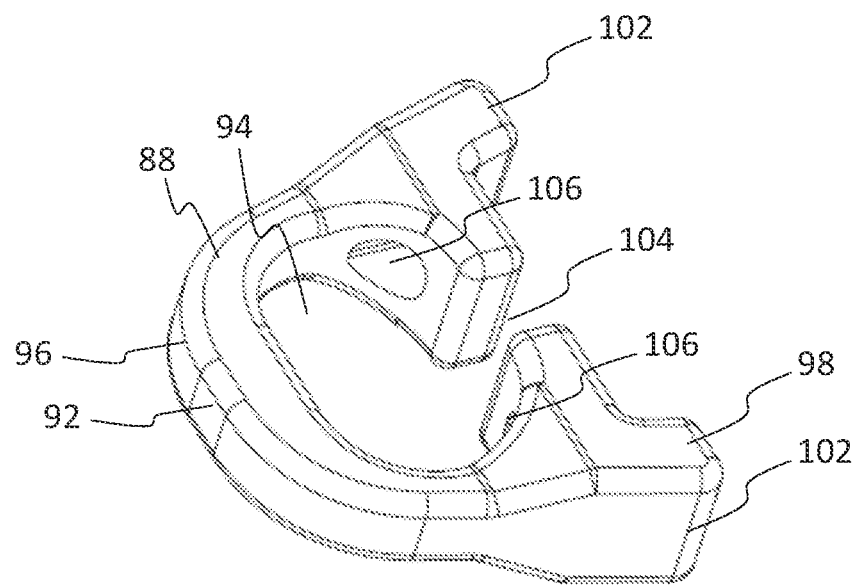

As shown in FIG. 5B, the anchor 88 may include a split ring body 92 with a central through opening 94. The anchor 88 may have a nose 96 configured to attach to the end 82 of the band 12, and a tail 98 receivable in the main body 22 of the implant 20. The tail 98 may include a pair of opposed projections 102. The projections 102 may be angled away from a central longitudinal axis B of the anchor 88 such that the projections 102 have a greater distance apart at the tail end 98. The projections 102 may also have a greater thickness than the nose 96. The central opening 94 may be in fluid communication with a cut 104. The cut 104 may allow the anchor 88 to flex and squeeze into the mating recess 90 in the main body 22. Once positioned fully within the mating recess 90, the anchor 88 may spring back open to prevent disassembly. The anchor 88 may also have one or more openings 106 configured to engage with a mating instrument to allow disassembly.

Figure 8:
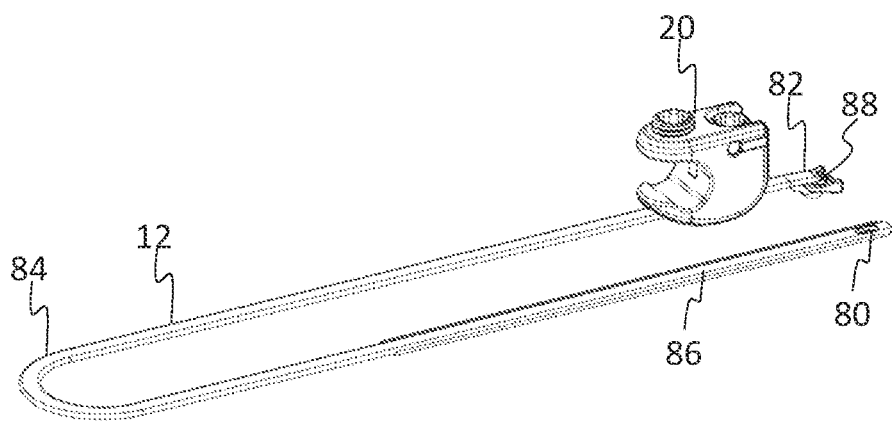
FIG. 8 shows the flexible band passed through the band clamp implant with anchor.
Figure 9:
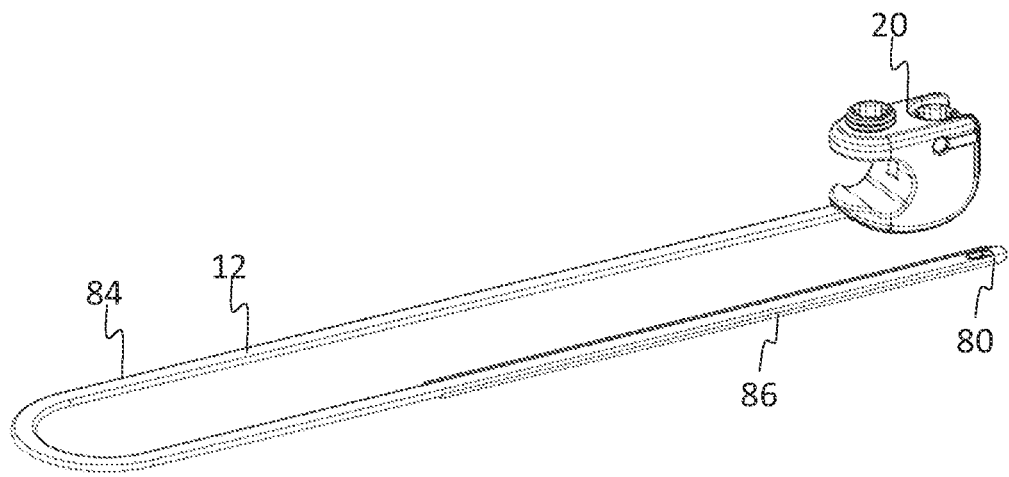
FIG. 9 shows the flexible band attached to the band clamp at the anchor.

As shown in FIG. 8, the flexible band 12 is inserted with the malleable leader 86 first, through recess 90 in the main body 22. As shown in FIG. 9, the band 12 is pulled through until the anchor 88 engages and is seated within the recess 90 in the implant 20. Engagement between the anchor 88 and the recess 90 causes the flexible band 12 to be securely attached to the main body 22 of the implant 20. The first free end 80 of the flexible band 12 with the malleable leader 86 and the middle portion 84 of the band 12 remain free to be positioned around patient anatomy. As shown in FIG. 1, the middle portion 84 of the band 12 may be looped around bone and the free end 80 of the band 12 may be threaded back into the implant 20 through the band opening 46. As shown in FIG. 4, the free end 80 may be pulled through the rear 34 of the implant 20. After tensioning the band 12, the second locking member 40 may be tightened, thereby securing the band 12 in the implant 20 and maintaining the desired tension around the bone.

Figure 10:
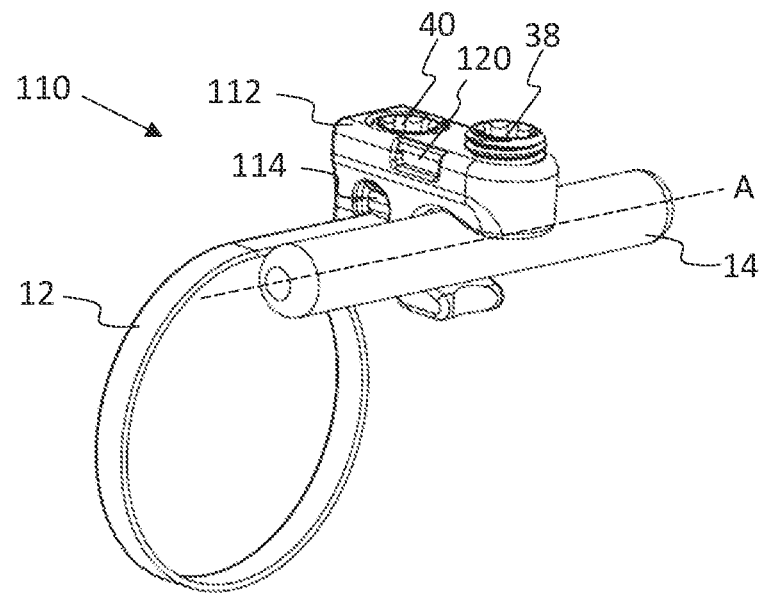
FIG. 10 shows a perspective view of a band clamp assembly according to one embodiment.
Figure 11:
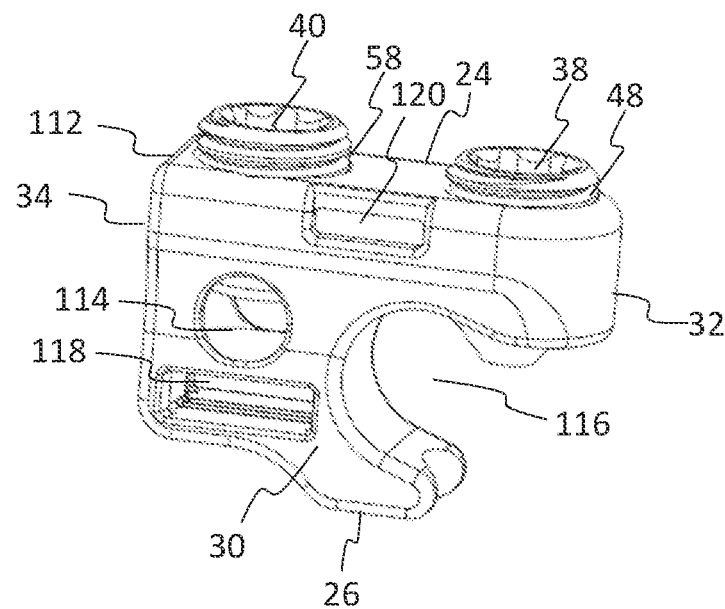
FIG. 11 is a perspective view of the band clamp implant show in FIG. 10.

Turning now to FIGS. 10 and 11, a band clamp implant assembly 110 is shown according to another embodiment. Band clamp implant assembly 110 is similar to implant assembly 10, except with a different configuration for the implant 112. Similar to implant 20, implant 112 includes a first locking member 38 for securing the rod 14 and a second locking member 40 for securing the band 12. In this embodiment, the band opening 114 is located adjacent to the rod slot 116 and the band opening 114 is oriented parallel to the long axis A of the spinal rod 14.

The implant 112 has a first opening or rod slot 116 to accept the spinal rod 14 and a second opening or band opening 114 to accept the flexible band 12. The rod slot 116 may be recessed into the front and bottom surfaces 32, 26 of the implant 20. The rod slot 116 may define a generally c-shaped recess sized and dimensioned to receive the rod 14. The band opening 114 may extend through the body between the first and second side surfaces 28, 30. The band opening 114 may define a generally cylindrical opening. The implant 112 has a first threaded hole 48 in fluid communication with the first opening 116. The first threaded locking member 38 may be positioned within the first threaded hole 48 to secure the spinal rod 14 to the implant 112. The implant 112 has a second threaded hole 58 in fluid communication with the second opening 114. The hole axis of the second threaded hole 58 may be generally perpendicular to the hole axis of the band opening 114.

The implant 112 has a separate mating recess 118 sized and dimensioned to mate with the anchor 88 on the flexible band 12. The mating recess 118 may be positioned beneath the band opening 114 and adjacent to the rod slot 116. The recess 118 may extend through the body between the first and second side surfaces 28, 30. The recess 118 may define a generally rectangular opening such that the recess 118 has a width greater than its height. The flexible band 12 may be inserted through the recess 118 such that the anchor 88 is engaged to the implant 112. In this manner, the anchor 88 secures the flexible band 12 to the implant 112 at free end 82 of the band 12. The flexible band 12 may be positioned around patient anatomy and the opposite free end 80 fed back through the band slot 114 in the implant 112, thereby creating a loop. The second threaded locking member 40 may be positioned within the second threaded hole 58 and moved downwardly to secure the flexible band 12 to the implant 112.

The implant 112 may define one or more engagement notches 120 for engagement with an insertion and/or tensioning instrument. For example, two opposed engagement notches 120 may be defined within the side surfaces 28, 30, near the top 24 of the implant 112. Each of the engagement notches 120 may include a slot extending along the length of the body, for example. It will be appreciated that other suitable engagement features may be used to temporarily couple the implant 112 to an instrument, such as inserter and/or tensioner.

According to one embodiment, a method of securing the flexible band 12 to the spinal rod 14 may involve one or more of the following steps in any suitable order. (1) Feeding the first free end 80 of flexible band 12 with the malleable leader 86 through the main body 22 of the band clamp implant 20, 112 and into a recess 90, 118 such that the first free end 80 and middle portion 84 of the flexible band 12 pass freely through the main body 22 while the second free end 82 of the flexible band 12 with the anchor 88 engages the recess 90, 118 and the flexible band 12 becomes secured to the band clamp 20, 112 at free end 82. (2) Passing the first free end 80 of the flexible band 12 around bony anatomy of the posterior spine creating a loop such that the middle portion 84 of the flexible band 12 contacts bone. (3) Passing the first free end 80 of the flexible band 12 back through the band slot 46, 114 of the band clamp 20, 112. (4) Positioning the band clamp 20, 112 along the spinal rod 14 such that the spinal rod 14 is accepted into the rod slot 44, 116 of the band clamp 20, 112. (5) Tightening the first threaded locking component 38 in the band clamp 20, 112 to secure the spinal rod 14 in the rod slot 44, 116 to the band clamp 20, 112. (6) Tensioning the flexible band 12 by providing a tensile force to the first free end 80 of the flexible band 12 thereby causing the loop to become tight around the bony anatomy. (7) Tightening the second threaded locking component 40 in the band clamp 20, 112 to force the saddle 64 into contact with the flexible band 12 in the band slot 46, 114 to secure the flexible band 12 to the band clamp 20, 112. (8) Cutting and removing any excess length of the flexible band 12 near the band clamp 20, 112. This method allows surgeons to achieve correction and fixation of a spinal deformity by securing the flexible band 12 to the spinal rod 14.

Turning now to FIGS. 12-18B, a band clamp implant assembly or system 130 is shown according to one embodiment. Similar to implant systems 10, 110, the implant 132 is configured to secure the flexible band 12 to the spinal rod 14. In addition, the implant 132 connects the flexible band 12 to a fastener, such as a pedicle screw 200, in order to provide additional fixation to the spine. The implant 132 is able to secure the flexible band 12 directly to the pedicle screw 200 without the need for additional rod connectors, which saves space on the construct and alleviates concerns over interference with other hardware and/or anatomy. Although a pedicle screw is exemplified herein, it will be appreciated that the fastener may include any suitable screw, anchor, or other device configured to attach to bone.

Figure 12:
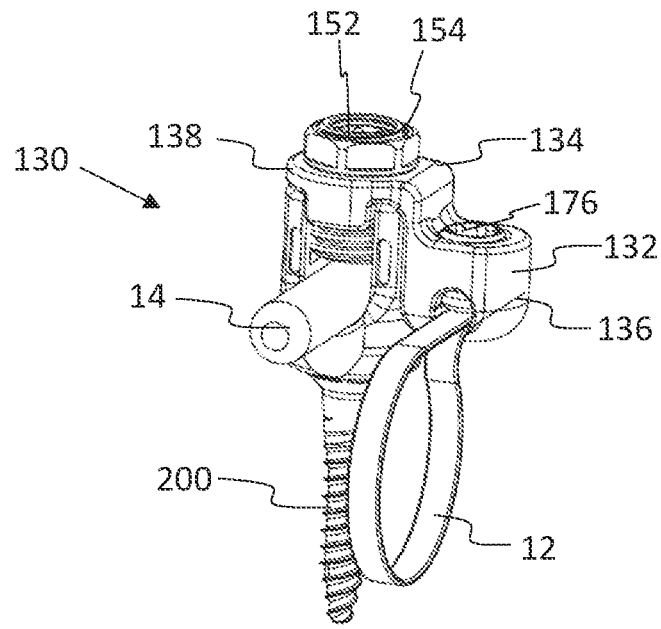
FIG. 12 is a perspective view of a band clamp assembly with a band clamp implant, a pedicle screw, a flexible band, and a spinal rod according to one embodiment.
Figure 13:
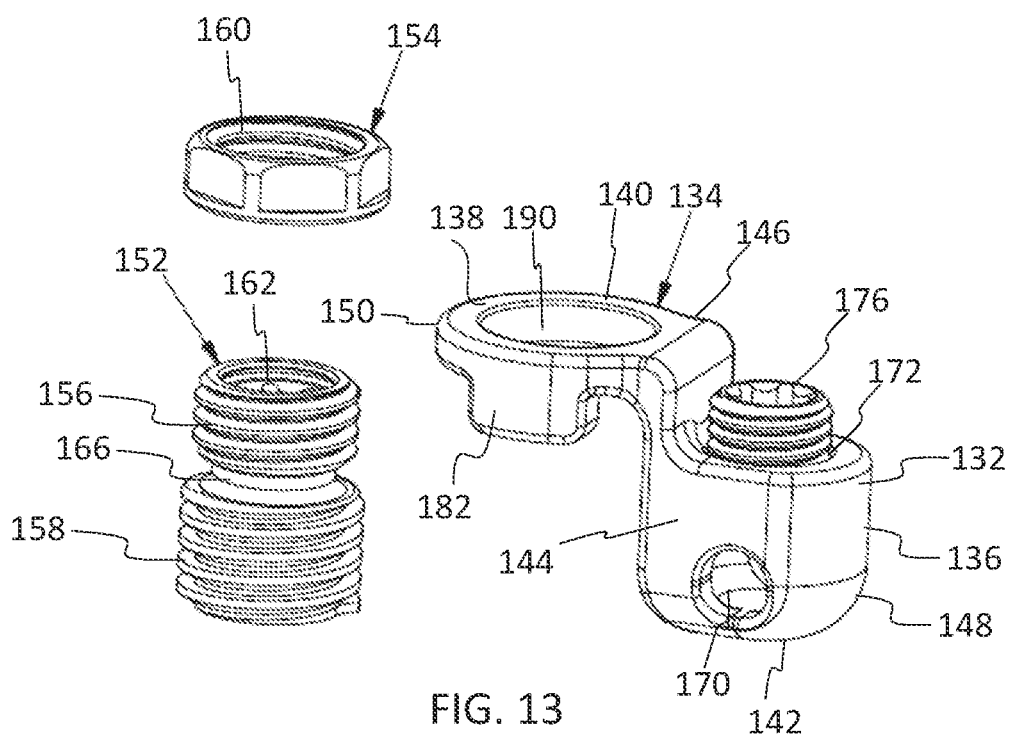
FIG. 13 is an exploded view of the band clamp implant of FIG. 12.

With emphasis on FIGS. 12 and 13, the implant system 130 includes a band clamp implant 132 capable of securing the flexible band 12 to the spinal rod 14. The band clamp 132 has an implant housing 134 with a first portion 136 configured for securing the band 12 and a second portion 138 configured for attaching the rod 14 and the pedicle screw 200. The second portion 138 may be stepped upward and may extend away from the first portion 138. The medial offset of the band clamp portion 136 allows the clamp to be located directly over the lamina for optimal placement of the flexible band 12. The implant housing 134 includes an upper surface 140, a lower surface 142, first and second side opposed surfaces 144, 146, a nose or front surface 148, and a back or rear surface 150.

Figure 14A:
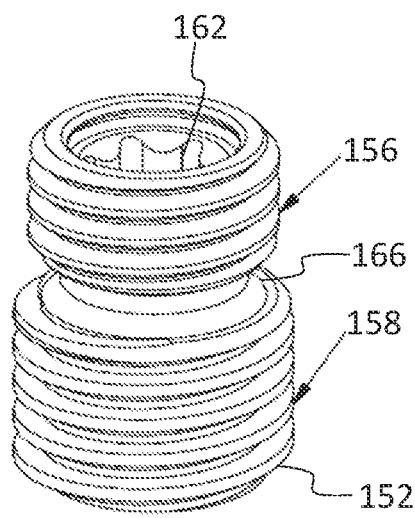
FIGS. 14A-14C show perspective, top, and cross-sectional views, respectively, of a locking cap post for securing the pedicle screw to the band clamp implant.
Figure 14B:
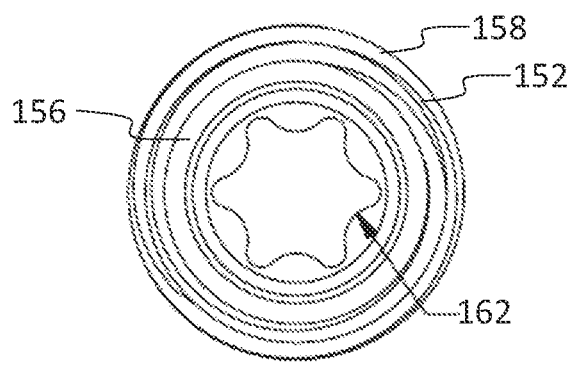
Figure 14C:
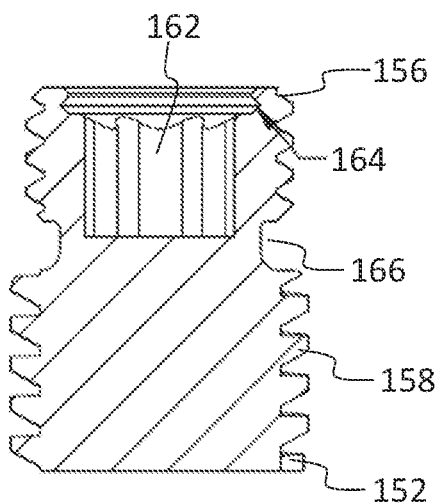

The implant system 130 includes an implant housing 132, a locking cap post 152, and a locking nut 154. As shown in FIGS. 14A-14C, the locking cap post 152 has two distinct threaded portions: an upper threaded portion 156 and a lower threaded portion 158. The upper threaded portion 156 is configured to mate with internal threads 160 in the locking nut 154. The lower threaded portion 158 is configured to mate with internal threads in the head 202 of the pedicle screw 200. The lower threaded portion 158 may be separated from the upper threaded portion 156 by a circumferential groove 166. The lower threaded portion 158 may have a major outer diameter greater than the major outer diameter of the upper threaded portion 156. The threads (e.g., handedness, form, angle, pitch, etc.) of the upper portion 156 may be the same or different than the threads of the lower portion 158. The upper threaded portion 156 may include an internal drive recess 162 configured for engagement with a driving instrument. The upper threaded portion 156 may also include an internal groove 164 for engagement with an insertion instrument. The spinal rod 14 may be secured into the head 202 of the pedicle screw 200 when the locking cap post 152 is threaded downwardly through an opening 190 in the implant housing 134, and the locking cap post 152 may be secured with the locking nut 154.

Figure 17A:
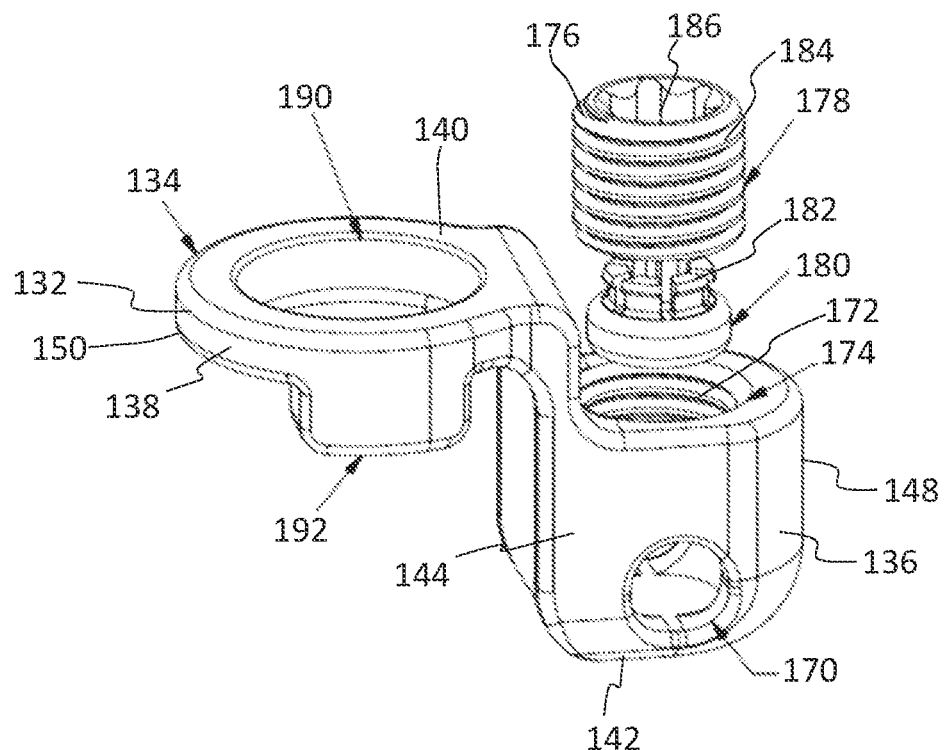
FIGS. 17A-17B show exploded and cross-sectional views, respectively, of the band clamp implant with the set screw and saddle configured for securing the band.
Figure 17B:
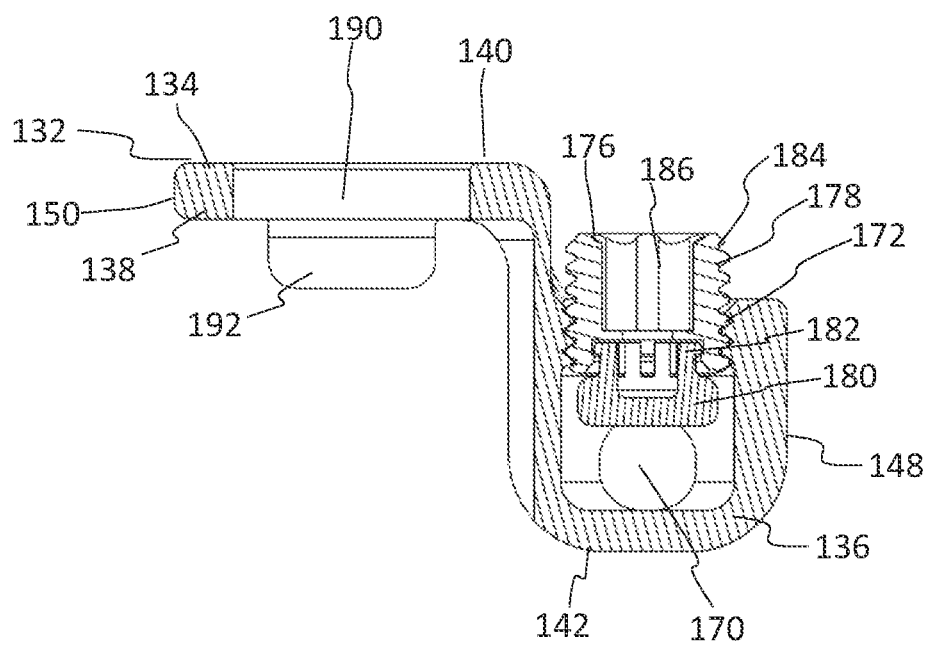

With reference to FIGS. 17A-17B, the first portion 136 of the implant housing 134 is configured to secure the flexible band 12. The first portion 136 of the implant housing 134 defines a band slot 170 configured to accept the flexible band 12. The band slot 170 may be cylindrical or of suitable shape. The band slot 170 is intersected by a hole 172. The hole 172 may be in fluid communication with the band slot 170. The hole 172 may include a threaded portion 174 around an inner periphery of the hole 172. A locking member 176 may be positioned within the hole 172 to secure the flexible band 12 within the band slot 170. The locking member 176 may include a fastener or set screw 178 and a saddle 180. The set screw 178 and saddle 180 may be attachable to one another. The saddle 180 may define a smooth, non-threaded ring or cylindrical body, and an upper surface of the saddle 180 may include one or more prongs 182 extending upwardly. The prongs 182 may mate with a corresponding recess within the lower surface of the set screw 178 to thereby connect the saddle 180 to the set screw 178. The set screw 178 may include a threaded portion 184 around an outer surface, which is configured to threadedly mate with the hole 174.

The set screw 178 may define an instrument recess 186 in an upper surface configured to be engaged by an instrument, such as a driver, for rotating the set screw 178 and moving the locking member 176 into the locked position. The set screw 178 and saddle 180 are attached to one another and are able to travel up and down within the threaded hole 174. The travel of the set screw 178 is such that the saddle 180 may reversibly interfere with the band slot 170 which accepts the flexible band 12. As shown in FIG. 17B, the flexible band 12 may be locked to the implant housing 134 by tightening the set screw 178, which forces the saddle 180 into contact with the flexible band 12. The flexible band 12 is then locked between the saddle 180 and the implant housing 134.

The second portion 138 of the implant housing 134 is configured to engage the head 202 of the pedicle screw 200. The second portion 138 of the implant housing 134 defines a thru hole 190 configured to accept the upper portion 156 of the locking cap post 152. The thru hole 190 may be non-threaded. The second portion 138 of the housing 134 may include one or more tabs 192. For example, the second portion 138 may include two opposed tabs 192 extending downwardly on opposite sides of the thru hole 190. The tabs 192 may be configured to engage the rod slot 206 of the pedicle screw 200. The geometry of the implant housing 134 is such that it fits tightly around the head 202 of the pedicle screw 200.

Figure 15:
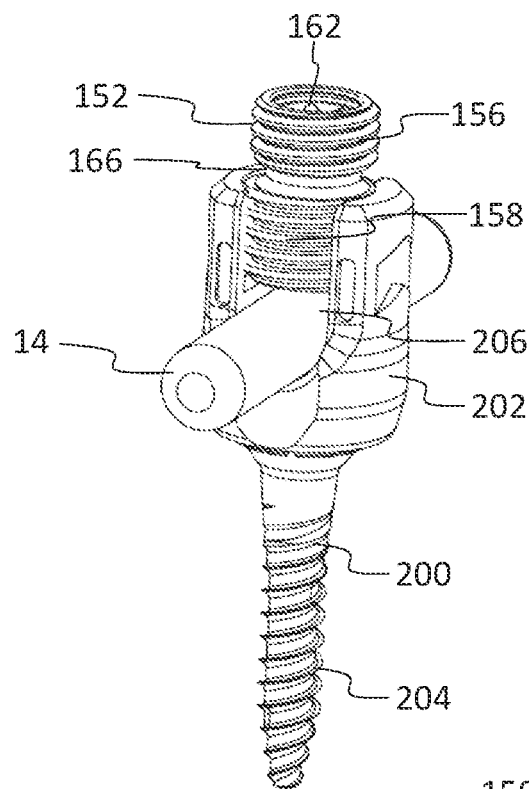
FIG. 15 is a perspective view of the locking cap post securing the spinal rod in the pedicle screw.
Figure 16:
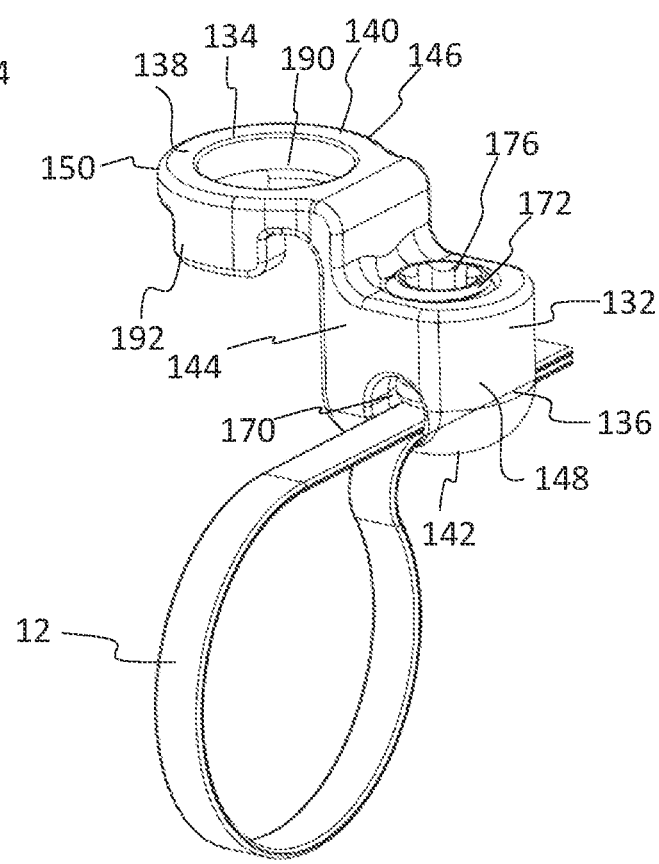
FIG. 16 shows a perspective view of the flexible band secured in the band clamp implant.

As shown in FIG. 15, the pedicle screw 200 includes a head 202 and a shaft 204. The head 202 may be in the form of a tulip with two opposing sides spaced apart by a slot 206 configured to receive the spinal rod 14. The rod 14 may be top-loaded into the tulip body. The tulip head 202 may define one or more recesses or engagement features configured to mate with an instrument, such as an inserter. The opposing sides of the tulip head 202 may define internal threads configured to mate with the exterior threads on the lower portion 158 of the locking cap post 152. The shaft 204 may include a threaded shank configured to engage bone. The pedicle screw 200 may be polyaxial, monoaxial, uniplanar, or of other suitable design.

Figure 18A:
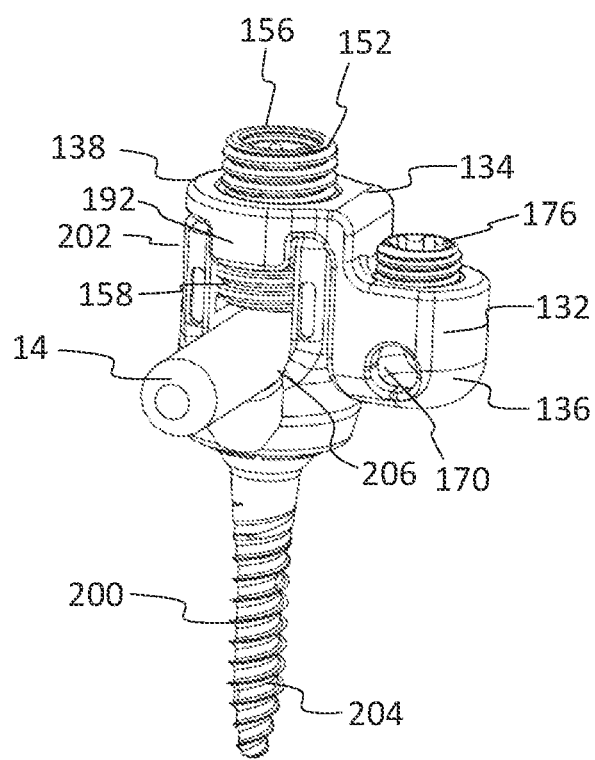
FIGS. 18A-18B show perspective views of the band clamp implant engaged with the pedicle screw and with a locking nut for securing the implant housing to the pedicle screw.
Figure 18B:
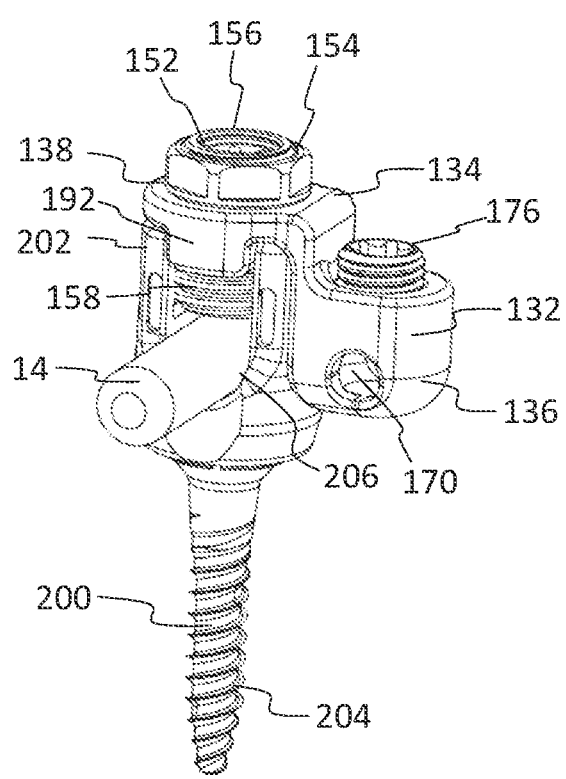

With emphasis on FIGS. 18A-18B, the implant housing 134 is secured to the pedicle screw 200 with the locking cap post 152 and the locking nut 154. In FIG. 18A, the locking cap post 152 is positioned through opening 190 in the implant housing 134 and into contact with the rod 14 positioned in the slot 206 in the head 202 of the pedicle screw 200. In FIG. 18B, the locking nut 154 is secured to the upper portion 156 of the locking cap post 152. The locking nut 154 has an internal thread 160 for engagement with the upper threaded portion 156 of the locking cap post 152. The outer geometry of the nut 154 is such that the nut 154 may be driven by an instrument. The bottom surface of the locking nut 154 contacts the upper surface 140 of the implant housing 134 to secure the implant housing 134 to the pedicle screw 200. The implant housing 134 is secured to the pedicle screw 134 via the force applied by the locking nut 154. The tabs 182 on the implant housing 134 allow the implant housing 134 to remain stable in torsion during tightening by preventing rotation of the implant housing 134.

According to one embodiment, a method of securing the flexible band 12 to the spinal rod 14 may involve one or more of the following steps in any suitable order: (1) securing the pedicle screw 200 into a pedicle of a vertebra; (2) positioning the rod 14 into the tulip head 202 of the pedicle screw 200; (3) attaching the implant 132 to the tulip head 202 of the pedicle screw 200 with the locking cap post 152 by threading the lower threaded portion 158 into mating threads within the tulip head 202; (4) connecting the locking nut 154 to the upper threaded portion 156 of the locking cap post 152 to lock the rod 14 in the tulip head 202; (5) feeding a free end of flexible band 12 into the band slot 170; (6) passing the other free end of the flexible band 12 around bony anatomy creating a loop that contacts bone; (7) passing the other free end of the flexible band 12 back through the band slot 170 of the band clamp 132; (8) tensioning the flexible band 12 by providing a tensile force to the free end(s) of the flexible band 12 thereby causing the loop to become tight around the bony anatomy; (9) tightening the locking member 176 in the band clamp 132 to force the saddle 180 into contact with the flexible band 12 in the band slot 170 to secure the flexible band 12 to the band clamp 132; and (10) cutting and removing any excess length of the flexible band 12 near the band clamp 132. This method allows surgeons to achieve correction and fixation of a spinal deformity by securing the flexible band 12 to the spinal rod 14.

Turning now to FIGS. 19-28C, a band clamp implant assembly or system 210 is shown according to one embodiment. Similar to implant system 130, the implant 212 is configured to secure the flexible band 12 to the spinal rod 14. In addition, the implant 210 connects the flexible band 12 to a bone fastener 214, such as a pedicle screw, in order to provide additional fixation to the spine. Although a pedicle screw is exemplified herein, it will be appreciated that the fastener may include any suitable screw, anchor, or other device configured to attach to bone.

Figure 19:
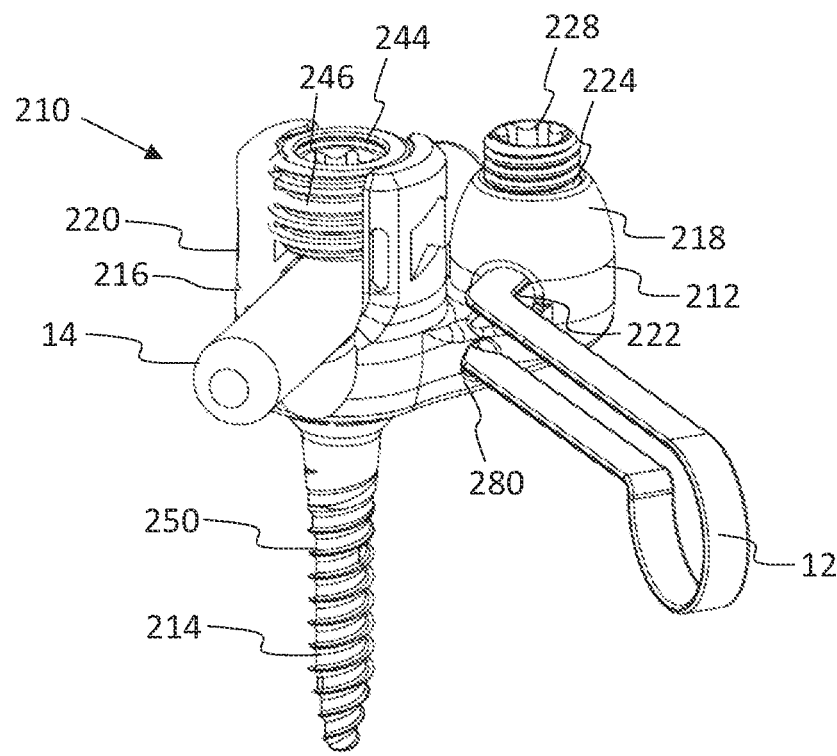
FIG. 19 shows a perspective view of a band clamp implant configured to secure the flexible band and spinal rod to a pedicle screw according to one embodiment.
Figure 20:
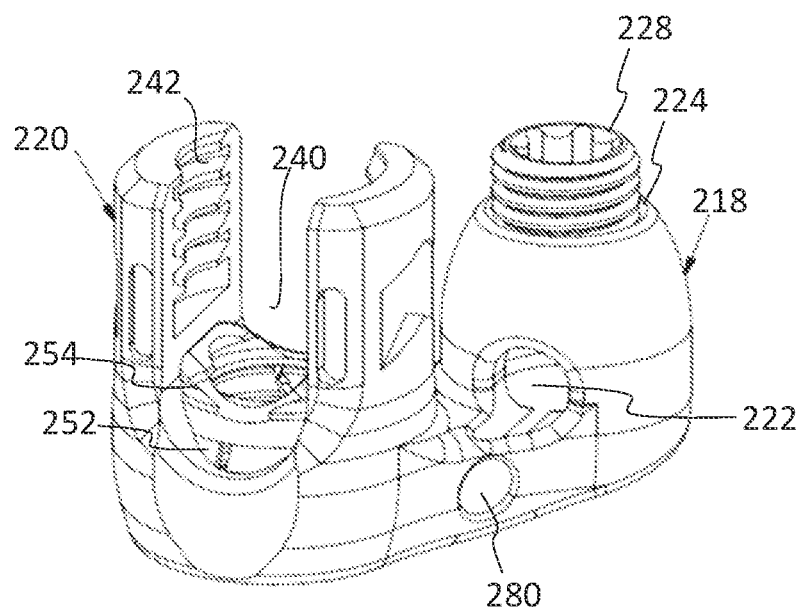
FIG. 20 is a perspective view of the band clamp implant of FIG. 19.

With emphasis on FIGS. 19 and 20, the implant system 210 includes a band clamp implant 212 capable of securing the flexible band 12 to the spinal rod 14. The implant 212 includes an integrated screw head 220 and band clamp 218. The main body 216 includes a first portion or band clamping portion 218 configured for securing the band 12 and a second portion or screw head portion 220 configured for attaching the rod 14 and the bone fastener or pedicle screw 214. The first portion 218 may be offset laterally and back from the second portion 220 of the implant 212. The medial offset of the band clamp portion 218 allows the clamp to be located directly over the lamina for optimal placement of the flexible band 12.

Figure 21:
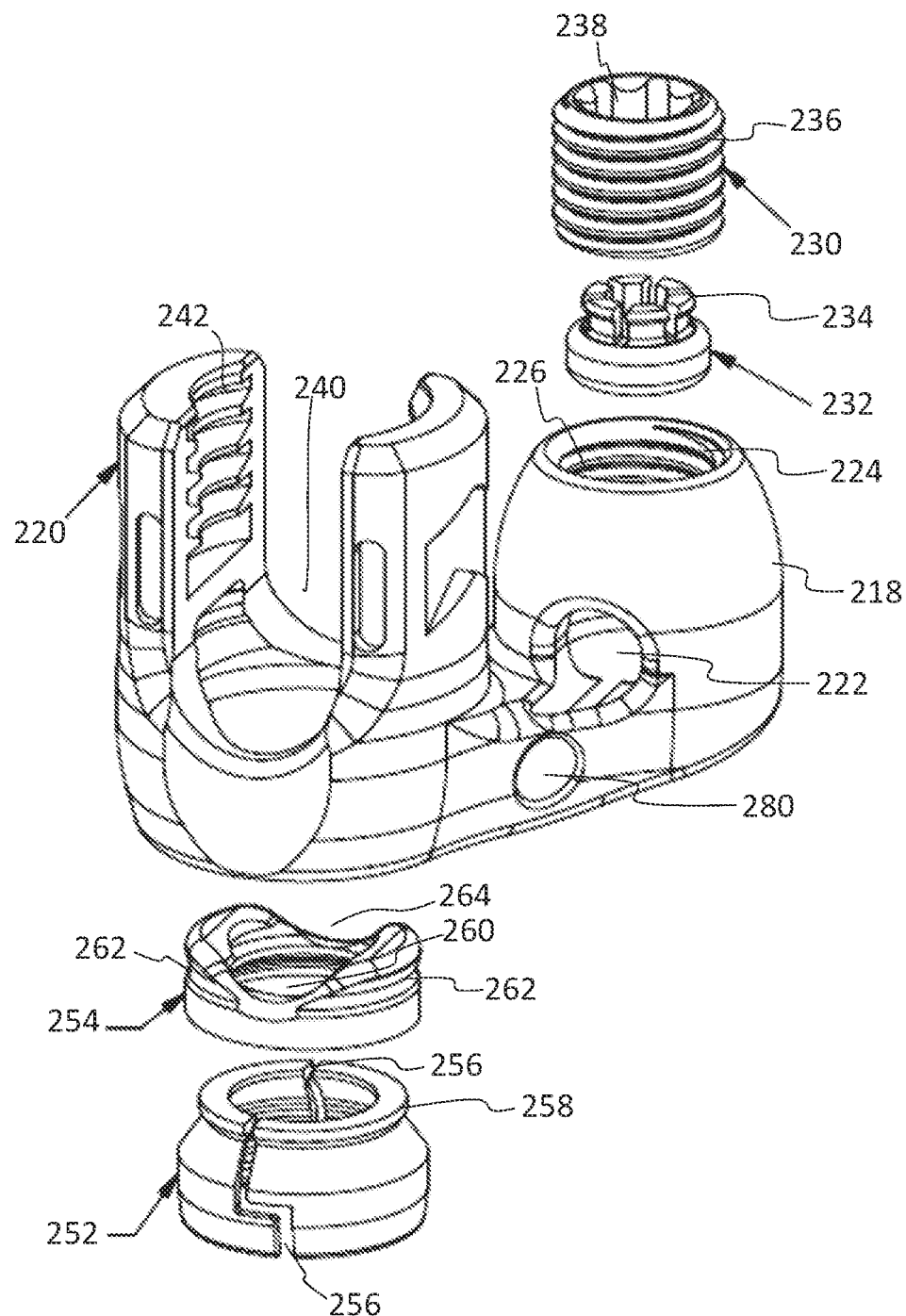
FIG. 21 is an exploded view of the band clamp implant of FIG. 20.

The band clamping portion 218 has a band slot 222 configured to accept the flexible band 12. The band clamping portion 218 has a through hole 224 intersecting and in fluid communication with the band slot 222. The hole 224 may include one or more threads 226 around an inner periphery of the hole 224. The locking member 228 may be positioned within the hole 224 to secure the flexible band 12 within the band slot 222. As shown in FIG. 21, the locking member 228 may include a fastener or set screw 230 and a saddle 232. The set screw 230 and saddle 232 may be attachable to one another. The saddle 232 may define a ring or cylindrical body, and an upper surface of the saddle 232 may include one or more prongs 234 extending upwardly. The prongs 234 may mate with a corresponding recess within the lower surface of the set screw 230 to thereby connect the saddle 232 to the set screw 230. The set screw 230 may include one or more external threads 236 around an outer surface, which is configured to threadedly mate with the interior threads 226 of hole 224. The set screw 236 may define an instrument recess 238 in an upper surface configured to be engaged by an instrument, such as a driver, for rotating the set screw 230 and moving the locking member 228 into the locked position.

The set screw 230 and saddle 232 may be attached to one another such that the set screw 230 and saddle 232 are able to travel up and down within the threaded hole 224. The travel of the set screw 230 is such that the saddle 232 may reversibly interfere with the band slot 222 which accepts the flexible band 12. The flexible band 12 may be locked to the band clamping portion 218 of the implant 212 by tightening the set screw 230, which forces the saddle 232 into contact with the flexible band 12. The flexible band 12 is locked between the saddle 232 and the band clamping portion 218 of the implant 212.

The screw head portion 220 may be in the form of a tulip with two opposing sides spaced apart by a slot 240 configured to receive the spinal rod 14. The rod 14 may be top-loaded into the tulip body. The opposing sides of the tulip head 220 may define internal threads 242 configured to mate with exterior threads 246 on the locking cap 244. The tulip head 220 may define one or more recesses or engagement features configured to mate with an instrument, such as an inserter. The screw head portion 220 of the implant 212 is configured to reversibly attach to the bone fastener 214. The bone fastener 214 may be bottom loaded into a bottom opening in the tulip body. The bone fastener 214 may include a head and a shaft portion 250. The shaft 250 may include a threaded shank configured to engage bone.

With emphasis on FIG. 21, the screw head portion 220 may retain a clamp 252 and a screw head saddle 254 configured to reversibly attach to the screw shank 250. The clamp 252 may include one or more clamp portions to provide a collar about the head of the bone fastener 214. The clamp 252 is configured to grip the bone fastener 214 when force is applied onto the clamp 252. The clamp 252 may define at least one slit 256 formed therein. For example, a pair of slits 256 may separate the clamp 252 into two clamp portions. The slit(s) 256 may be stepped, linear, curved, or otherwise configured. The slit(s) 256 may allow for first and second clamp portions to constrict and securely engage the head of the bone fastener 214. A portion of the outer surfaces of the clamp 252 may be tapered and an upper portion may define an external lip 258 configured to be mated with the saddle 254. An outer surface of the clamp 252 may abut and engage an inner surface of the tulip head 220 when fully installed and locked in place. When fully installed and locked in place, inner surfaces of the clamp 252 may abut and engage the head of the bone fastener 214. The inner surfaces of the clamp 252 may include a roughened, textured, or threaded surface configured to improve engagement with the head of the bone fastener 214.

The saddle 254 may be introduced downwardly from the top of the tulip head 220 to seat on top of the clamp 252. The saddle 254 may include a through bore 260. A lower portion of the bore 260 may be sized to receive the upper portion of the clamp 252, including external lip 258 of the clamp 252. The saddle 254 may include a generally rounded outer surface defining a recessed portion or groove 262. The upper surface of the saddle 254 may define a convex seat 264 that receives the rod 14, when loaded from the top of the tulip 220. The saddle 254 may engage interior surfaces of the tulip head 220 to prevent upward movement of the clamp 252, thereby locking the clamp 252 into engagement with the head of the bone fastener 214.

Figure 22A:
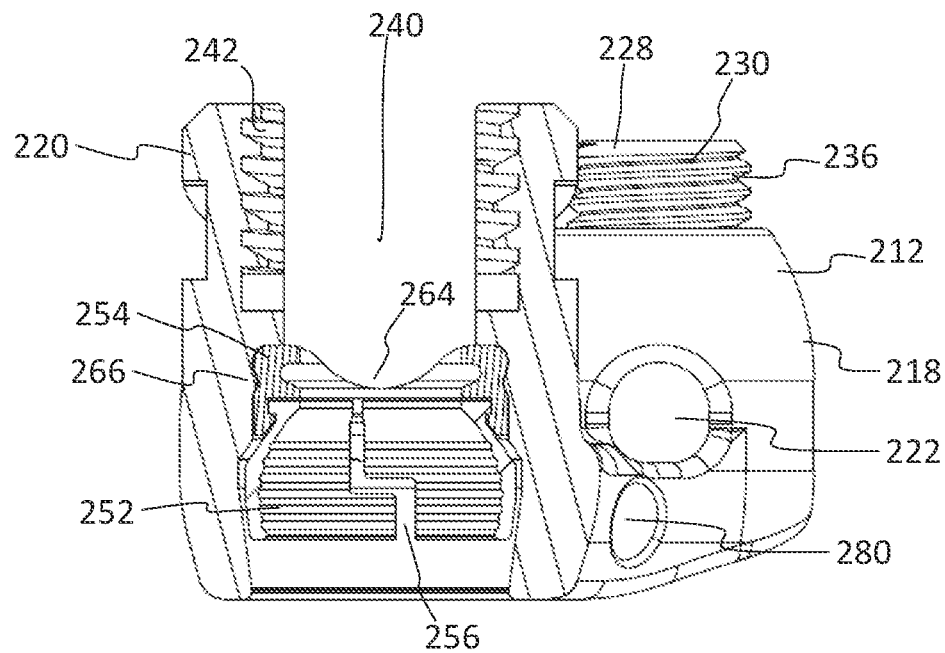
FIGS. 22A-22B show cross-sectional views of the integrated screw head with the saddle in a loading position and a locked position, respectively.
Figure 22B:
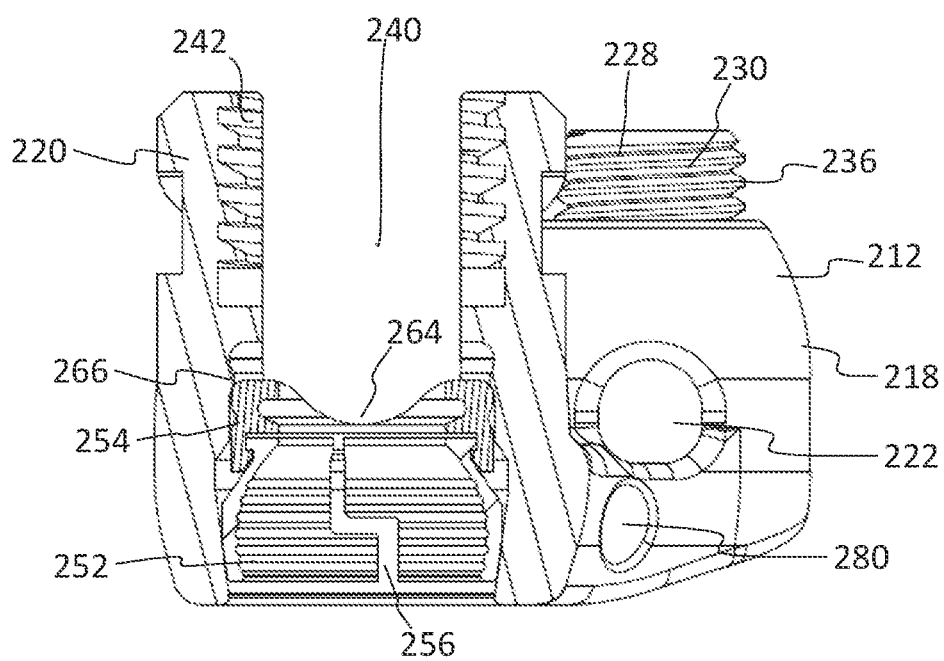

With emphasis on FIGS. 22A-22B, geometry within the head portion 220 allows the clamp 252 and saddle 254 to be positioned above or below a modular bump 266. In a loading position shown in FIG. 22A, the saddle 254 and clamp 252 are in an upward position. The clamp 252 and saddle 254 are positioned above the modular bump 266, and the clamp 252 is able to flex open to accept the head of the screw shank 250. In the locked position shown in FIG. 22B, the saddle 254 and clamp 252 are in a downward position. The clamp 252 and saddle 254 are positioned below the modular bump 266, and the clamp 252 is unable to open and prevents the head of the screw shank 250 from being released. Once the spinal rod 14 is seated in the rod slot 240 and onto seat 264 of the saddle 254, the threaded locking cap 244 is rotated downwardly to secure the spinal rod 14 and bone fastener 214 in the construct.

Figure 23A:
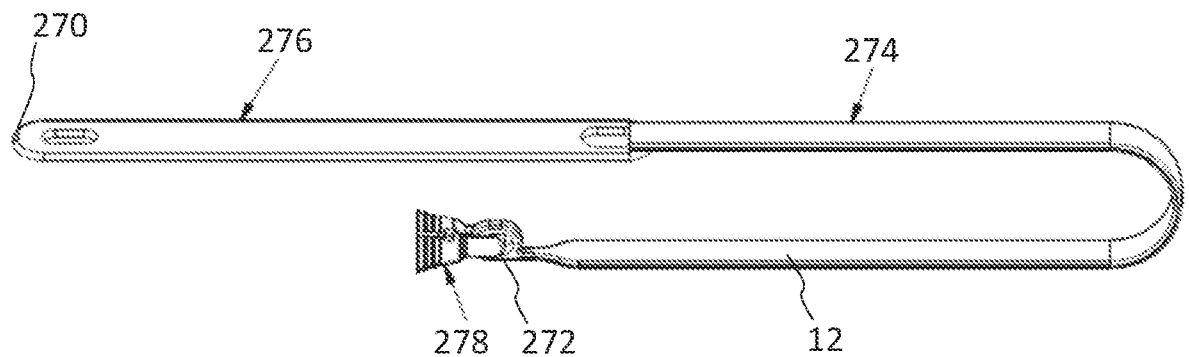
FIGS. 23A-23B show an embodiment of the flexible band with a leader and a close up of a buckle.
Figure 23B:
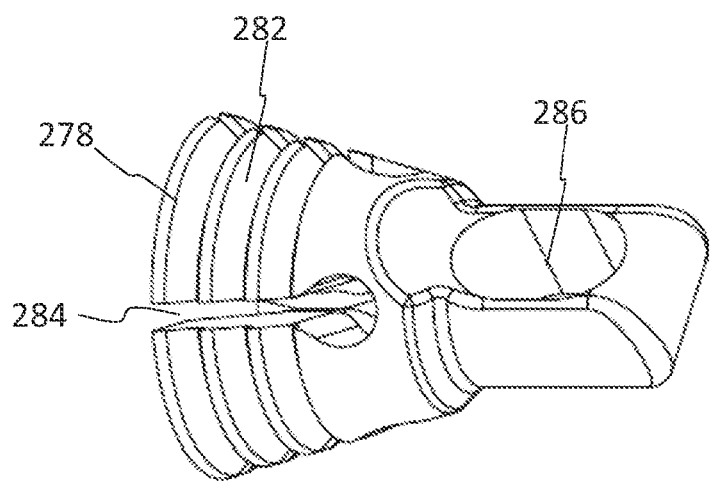
Figure 24:
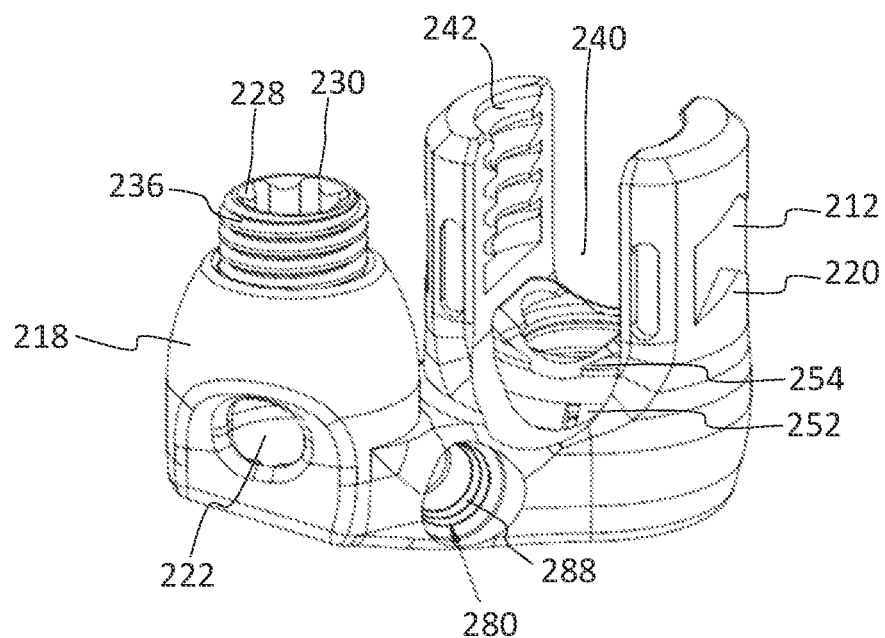
FIG. 24 is a perspective view of the back of the band clamp implant showing a recess for receiving the buckle.
Figure 25:
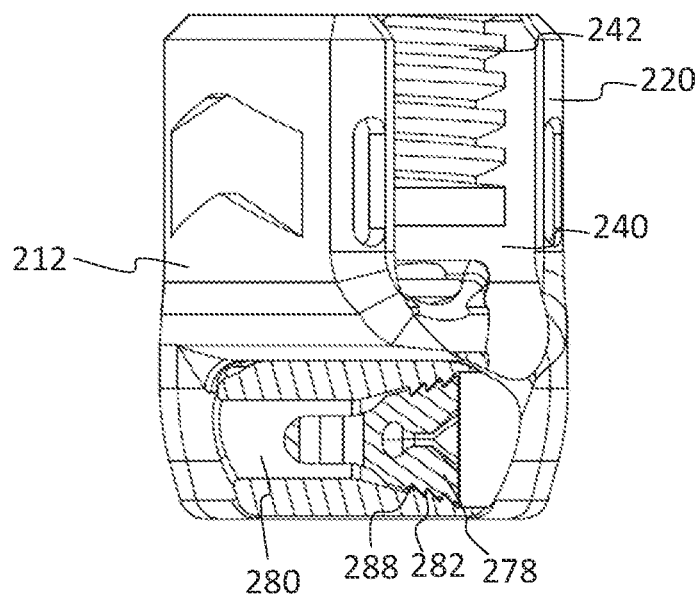
FIG. 25 is a cross-sectional view of the buckle in the recess.
Figure 26:
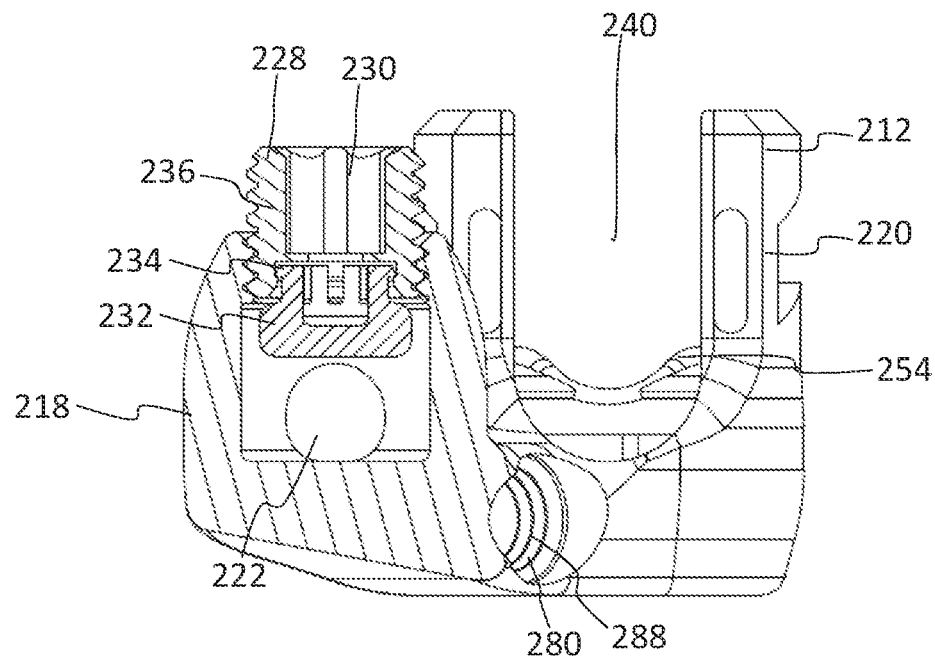
FIG. 26 is a cross-sectional view of the band clamp implant showing the set screw and saddle configured for securing the band.
Figure 27:
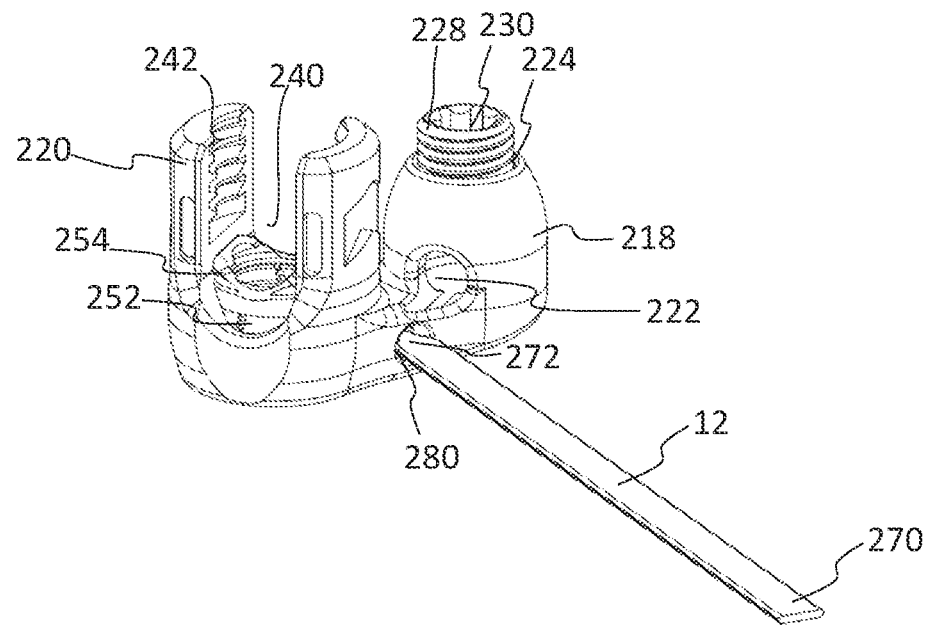
FIG. 27 is a perspective view of the band clamp implant with the flexible band attached.

Turning now to FIGS. 23A-23B, the flexible band 12 may extend from a first free end 270 to an opposite second free end 272 with a middle portion 274 in between. The middle portion 274 of the flexible band 12 is configured to contact and/or loop around bone. The first free end 270 of the flexible band 12 may be attached to a leader 276. The leader 276 may define an opening for guiding the band 12 with an instrument, k-wire, suture, or the like. The leader 276 may be a malleable leader configured to be fed around anatomy to wrap the flexible band 12 around the anatomy to be fixated. The second free end 272 of the flexible band 12 may be attached to an anchor or buckle 278. The buckle 278 may have a geometry such that the buckle 278 may be engaged with a mating recess 280 in the implant 212. As shown in FIG. 19, the mating recess 280 may be separate from and located beneath the band slot 222. The hole axis of the mating recess 280 may be offset and transverse to the hole axis of the band slot 222. The geometry of the mating recess 280 is sized and dimensioned such that the buckle 278 is receivable and securable within the recess 280.

The buckle 278 may be conical in shape with one or more grooves 282 for engagement with corresponding grooves 288 in the mating recess 280 in the implant 212. For example, the buckle 278 may include a plurality of circumferential grooves 282 extending from the widest part of the base of the buckle 278. The buckle 278 has at least one flexure cut 284 to allow the outer geometry of the buckle 278 to squeeze into the mating recess 280. The flexure cut 284 may cut through one or more of the grooves 282. When the grooves 282 on the buckle align with the grooves 288 in the recess 280, the flexure cut 284 allows the buckle 278 to spring back to its original shape, thus preventing disassembly. The buckle 278 includes a loop 286, around which the flexible band 12 may be attached. As shown in FIG. 23A, the free end 272 of the band 12 may be looped repeatedly around the loop 286 of the buckle 278 to secure the band 12 to the buckle 278. It will be appreciated that other suitable attachment mechanisms, such as knotting, fasteners, adhesives, or the like, may be used to secure the band 12 to the buckle 278.

As shown in FIGS. 24-27, the implant 212 defines an internal recess 280 configured to accept the flexible band 12 and buckle 278. The internal recess 280 defines a plurality of grooves 288 that mate with the grooves 282 on the buckle 278. As the flexible band 12 is passed through the recess 280, from back to front, the buckle 278 snaps into the mating grooves 288. After assembly, the flexible band 12 is securely attached to the implant 212 via buckle 278 at free end 272 of the band 12.

Figure 28A:
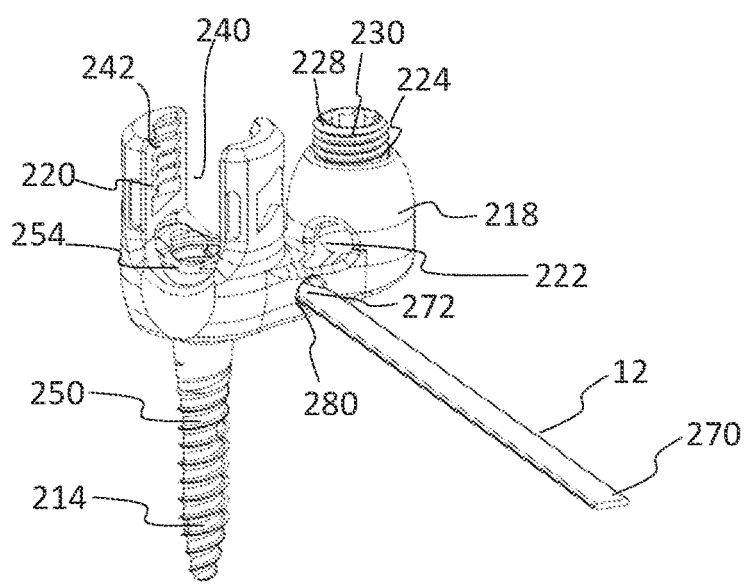
FIGS. 28A-28C show the band clamp implant attached to the screw shank, the rod secured to the implant, and the band secured to the implant to create a loop, respectively.
Figure 28B:
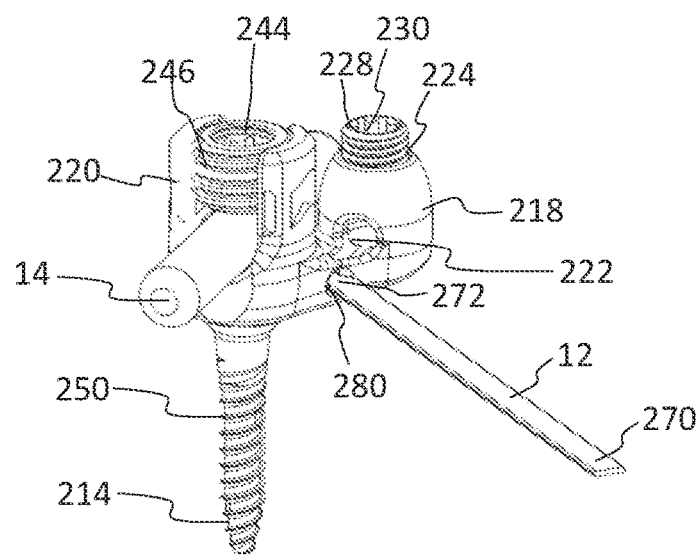
Figure 28C:
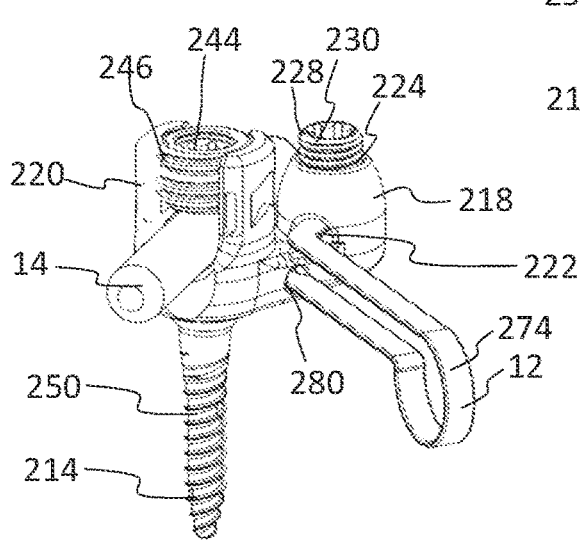
Figure 29:
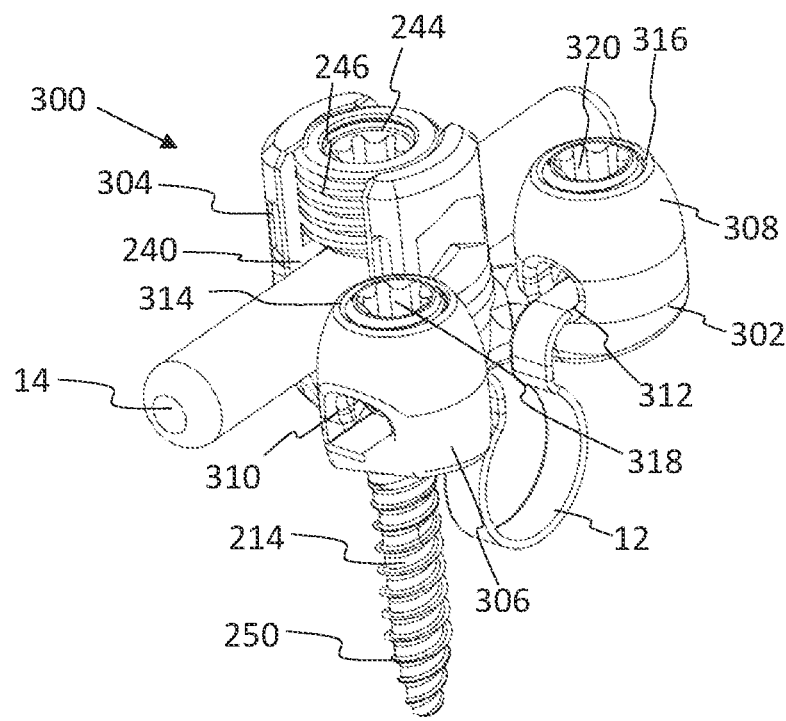
FIG. 29 shows a perspective view of an integral band clamp implant configured to secure the flexible band and spinal rod to a pedicle screw according to one embodiment.
Figure 30:
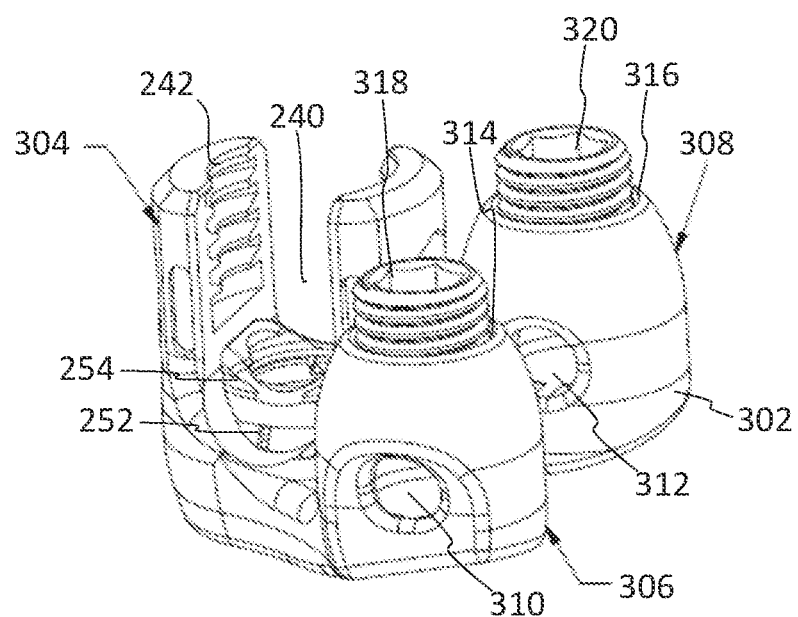
FIG. 30 is a perspective view of the band clamp implant of FIG. 29.
Figure 31:
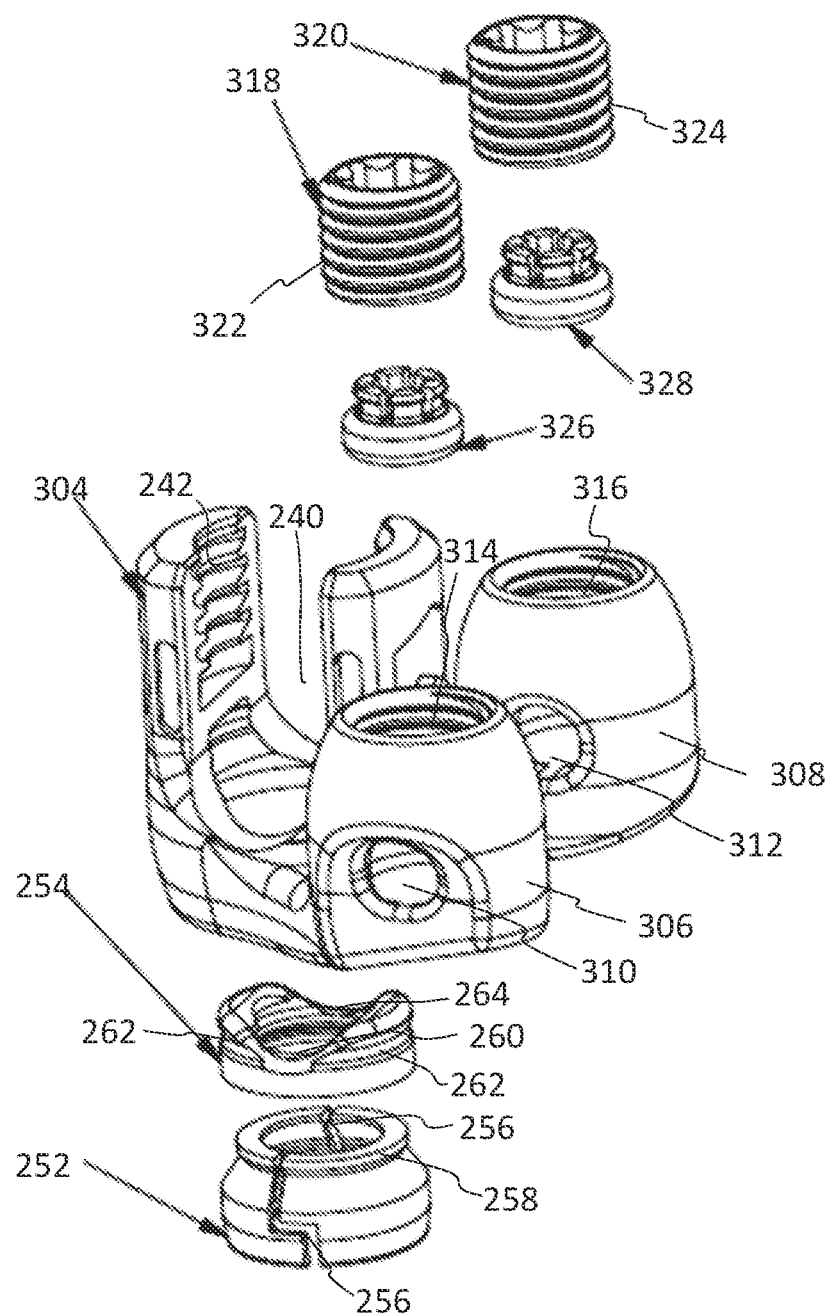
FIG. 31 is an exploded view of the band clamp implant of FIG. 30.
Figure 32:
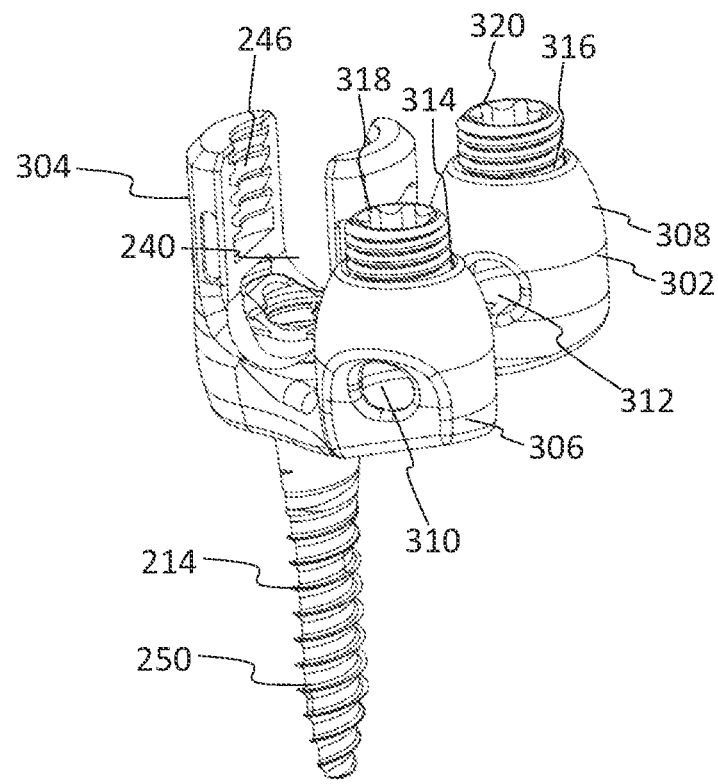
FIG. 32 is a perspective view of the band clamp implant attached to the screw shank.

As shown in FIGS. 28A-28C, after the flexible band 12 is passed through the recess 280, the buckle 278 snaps into place, thereby securing the flexible band 12 to the implant 212. As shown in FIG. 28A, the tulip body 220 is then attached to the screw shank 250 by bottom loading the screw 214 into the tulip 220. As shown in FIG. 28B, the spinal rod 14 may be placed in the rod slot 240 from the top of the tulip 220 and secured with the locking cap 244. The locking cap 244 also secures the polyaxial screw 214 via the downward force onto the screw head saddle 254 and clamp 252. As shown in FIG. 28C, the free end 270 of the flexible band 12 is passed around the bony anatomy and back into the band clamp portion 218 of the implant 212 through the band slot 222 to create a loop. The loop is tensioned to provide fixation to the bone and then the set screw 230 of the locking member 228 is tightened downwardly to lock the flexible band 12 to the implant 212.

Turning now to FIGS. 29-33, a band clamp implant assembly or system 300 is shown according to one embodiment. Similar to implant system 210, the implant 302 is configured to secure the flexible band 12, spinal rod 14, and bone fastener 214. In this embodiment, the system 300 includes two band clamp portions 306, 308 configured to receive and secure the band 12 integrally connected to a single tulip-style head 304.

The implant 302 includes an integrated screw head 304 with two band clamps 306, 308. As shown in the exploded view in FIG. 31, the integrated screw head portion 304 is the same as integrated tulip-style screw head 220 and includes clamp 252 and saddle 254, which reversibly attach to the screw shank 250. The geometry within the head portion 220 allows the clamp 252 and saddle 254 to be positioned above or below the modular bump 266. In the loading position when the clamp 252 and saddle 254 are positioned above the modular bump 266, the clamp 252 is able to flex open to accept the head of the screw shank 250. In the locked position when the clamp 252 and saddle 254 are positioned below the modular bump 266, the clamp 252 is unable to open and prevents the head of the screw shank 250 from being released. The screw head portion 304 includes rod slot 240 to accept the spinal rod 14 and accepts the threaded locking cap 244 to secure the spinal rod 14.

The implant 302 includes two band clamps 306, 308, which are separate and distinct from one another. A first band clamp 306 sits toward the front of the implant 302 and a second band clamp 308 sits toward the back of the implant 302. Both clamps 306, 308 may be medially offset to the pedicle screw 214, which allows the clamps 306, 308 to be located directly over the lamina for optimal placement of the flexible band 12.

Figure 33:
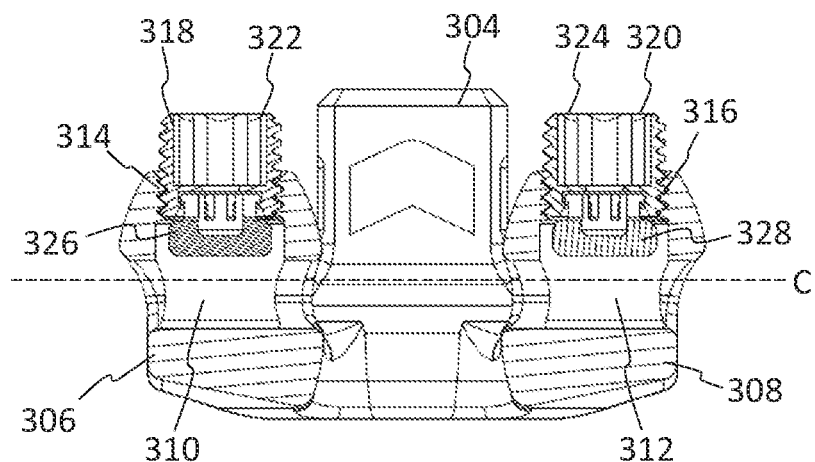
FIG. 33 is a cross-sectional view of the implant showing set screws and saddles in the two band clamp portions of the implant.

Band clamps 306, 308 may be similar to band clamp 218. Each band clamp portion 306, 308 has a band slot 310, 312 for accepting the flexible band 12 and a threaded hole 314, 316, which intersects the respective band slot 310, 312. The front band slot 310 may be aligned with the back band slot 312. For example, as shown in FIG. 33, a central hole axis of the front band slot 310 may be coaxial with a central hole axis of the back band slot 312 along axis C. The threaded holes 314, 316 may be aligned generally perpendicular to axis C. The front threaded hole 314 may be positioned generally parallel to the back threaded hole 316.

The implant 302 includes two locking members 318, 320 receivable in the respective holes 314, 316. Similar to locking member 228, each of the locking members 318, 320 may include a set screw 322, 324 engaged with a saddle 326, 328, respectively. The set screw 322, 324 and saddle 326, 328 travel within the respective threaded hole 314, 316 such that the saddle 326, 328 can reversibly interfere with the band slot 310, 312. Each band slot 310, 312 may accept one free end of the flexible band 12, thereby creating a loop therebetween. The set screws 322, 324 are threaded downward, which forces the saddles 326, 328 to contact the band 12. The force applied by the thread locks the flexible band 12 between the saddle 326, 328 and the main body of the clamps 306, 308.

According to one embodiment, a method of securing the flexible band 12 to the spinal rod 14 may involve one or more of the following steps in any suitable order: (1) securing the pedicle screw 214 into a pedicle of a vertebra; (2) bottom loading the pedicle screw 214 into the tulip head 304 of the implant 302; (3) top loading the rod 14 into the tulip head 304 of the implant 302; (4) connecting the locking cap 244 to the top of the tulip head 304 to lock the rod 14 and the position of the pedicle screw 214; (5) feeding a free end of flexible band 12 into the band slot 310 of the front band clamp 306; (6) passing the other free end of the flexible band 12 around bony anatomy creating a loop that contacts bone; (7) passing the other free end of the flexible band 12 into the band slot 312 of the rear band clamp 308; (8) tensioning the flexible band 12 by providing a tensile force to the free end(s) of the flexible band 12 thereby causing the loop to become tight around the bony anatomy; (9) tightening the locking members 318, 320 in the band clamps 306, 308 to force the respective saddles 326, 328 into contact with the flexible band 12 in the band slots 310, 312 to secure the flexible band 12 to the band clamps 306, 308; and (10) cutting and removing any excess length of the flexible band 12 near band clamps 306, 308. This method allows surgeons to achieve correction and fixation of a spinal deformity.

Figure 34A:
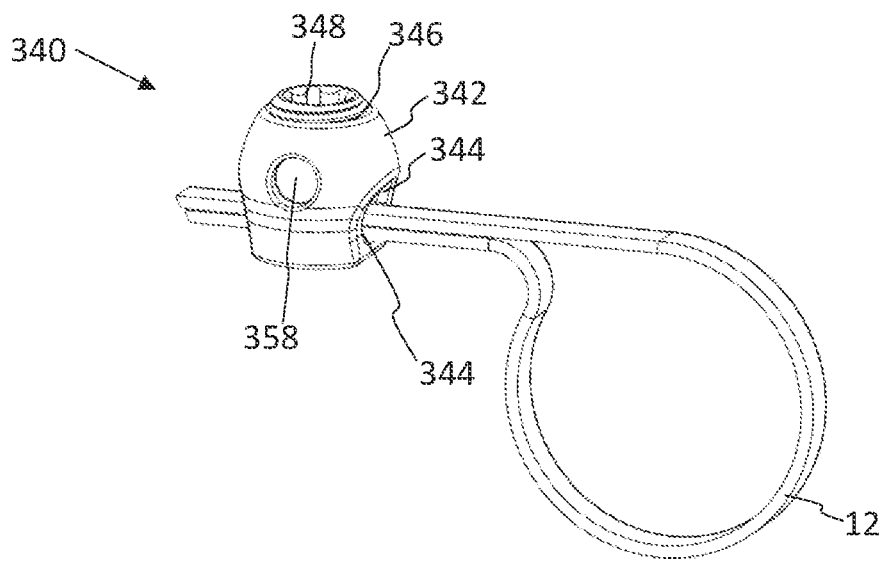
FIGS. 34A-34C show perspective and cross-sectional views of a free band clamp configured for securing the flexible band according to one embodiment.
Figure 34B:
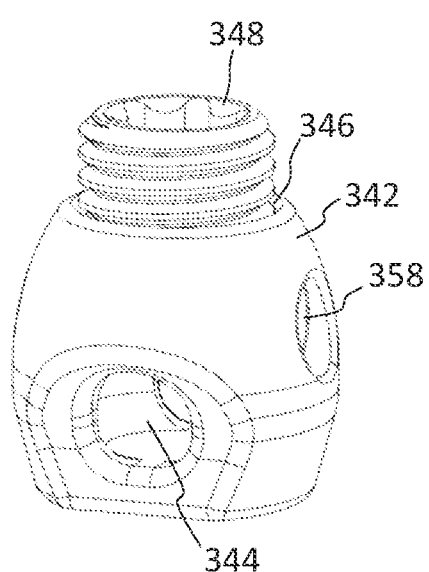
Figure 34C:
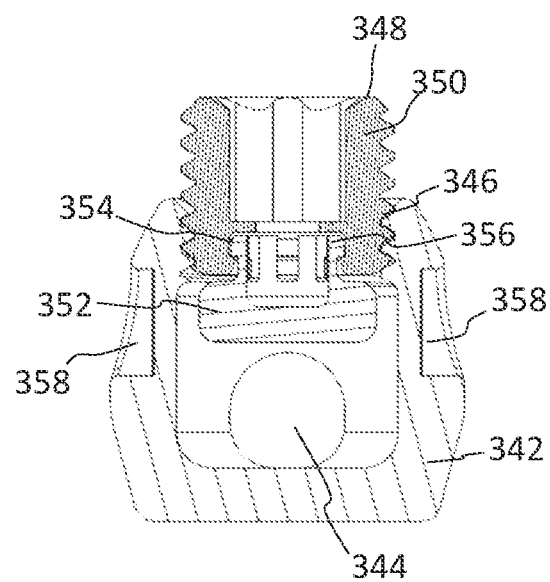

Turning now to FIGS. 34A-34C, a band clamp implant assembly or system 340 is shown according to one embodiment. The implant system 340 includes a free band clamp implant 342, which is not intended to secure the flexible band 12 to a pedicle screw or spinal rod. The free band clamp 342 has a main body defining a band slot 344 for receiving the band 12 therethrough. The band slot 344 may extend through the body of the clamp 342 from the front to the back of the implant 342. The body further defines a threaded hole 346, which intersects the band slot 344.

The implant 342 is configured to retain a locking member 348 which includes a set screw 350 and a saddle 352. The set screw 350 and saddle 352 are attached to one another and able to translate within the threaded hole 346. The set screw 350 may have a groove 354 on the lower inner portion that mates with one or more tabs or prongs 356 on the saddle 352. The tabs or prongs 356 on the saddle 352 may flex inward when pressed into the set screw 350 and snap back to its original shape when it reaches the groove 354. The set screw 350 is able rotate independently of the saddle 352.

The band slot 344 is able to accept one or both ends of the flexible band 12. When the set screw 350 is threaded downward, the saddle 352 is forced into contact with the flexible band 12. The force exerted by the threads of the set screw 350 secures the flexible band 12 in the band slot 344 between the saddle 352 and a lower surface of the implant 342. The implant 342 may include one or more recesses 358 or other suitable feature for engagement with an insertion and/or tensioning instrument. The implant 342 is configured to lock the flexible band 12 in tension after the flexible band 12 has been wrapped around bony anatomy to provide fixation. In particular, the band 12 may be threaded through the band slot 344, looped around bone, and threaded back through the same band slot 344. The single locking member 348 then locks both ends of the band 12, thereby maintaining the tension to the band 12.

Turning now to FIGS. 35-38C, a band clamp implant assembly or system 360 is shown according to one embodiment. Similar to implant system 10, the implant 362 is configured to connect the flexible band 12 to the spinal rod 14, which may provide supplemental fixation to pedicle screws, for example. The implant 362 may be useful in providing additional fixation in patients with poor bone quality and/or where pedicle screw fixation may be insufficient.

Figure 35:
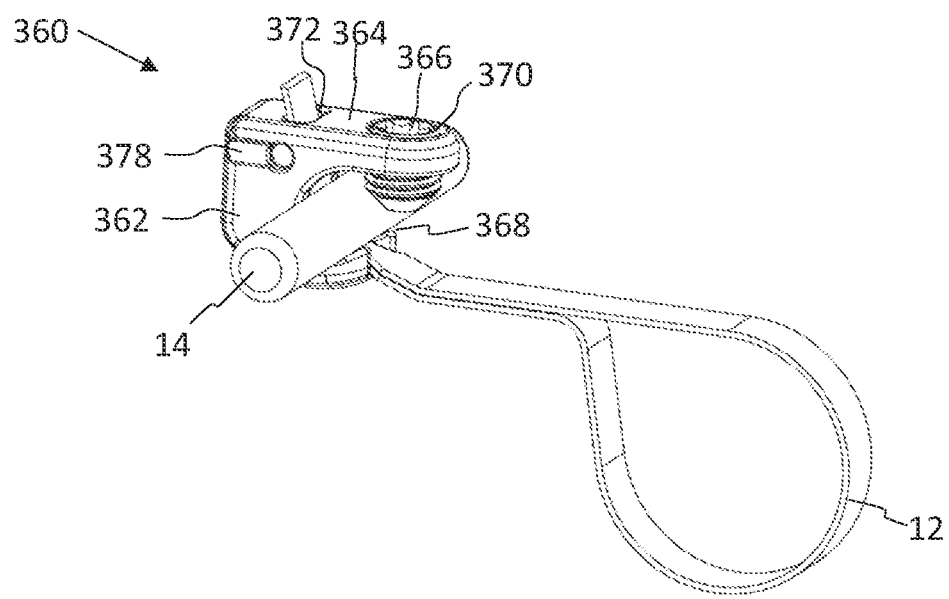
FIG. 35 shows a perspective view of a band clamp implant configured to secure the flexible band and spinal rod according to one embodiment.
Figure 36:
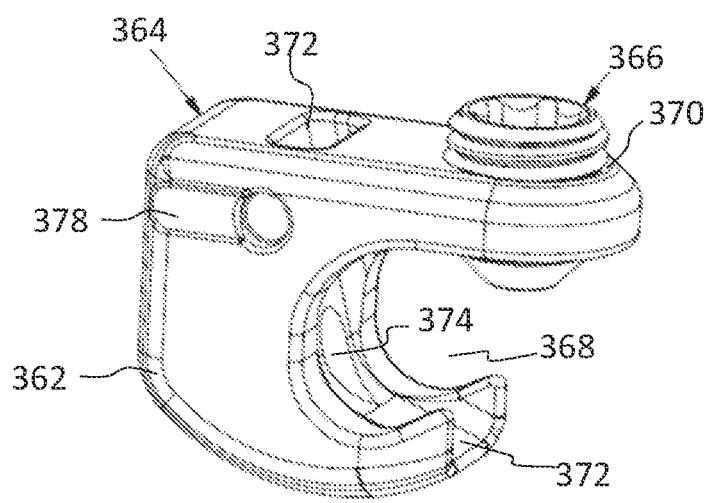
FIG. 36 is a perspective view of the band clamp implant of FIG. 35.

As shown in FIGS. 35 and 36, the implant 362 includes a main body 364 and a securing member, such as a set screw 366, configured for retaining the spinal rod 14 in the implant 362. The main body 364 defines a rod slot 368 configured to accept the spinal rod 14 and a threaded hole 370, which intersects the rod slot 368. The threaded hole 370 may be offset relative to the rod slot 368. The set screw 366 is able to thread up and down within the threaded hole 370 in order to reversibly interfere with the rod slot 368. The lower surface of the set screw 366 may be angled in order to press against the rod 14. In a locked position, the lower surface of the set screw 366 contacts the rod 14, thereby securing the rod 14 in the rod slot 368.

Figure 37A:
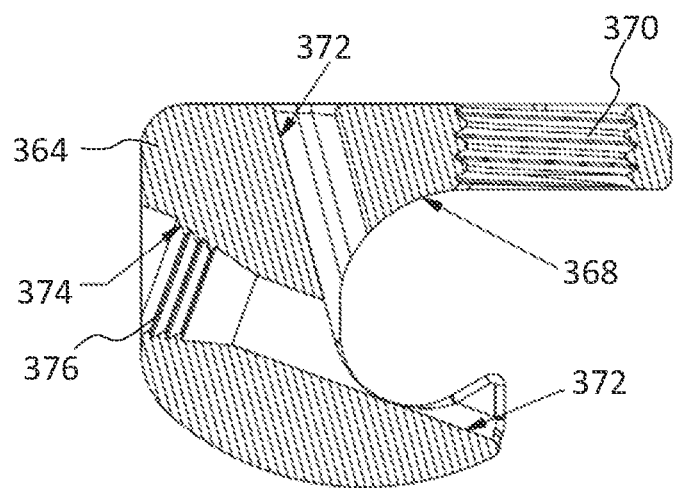
FIGS. 37A-37B show cross-sectional views of the band clamp implant without and with the buckle and band affixed thereto.
Figure 37B:
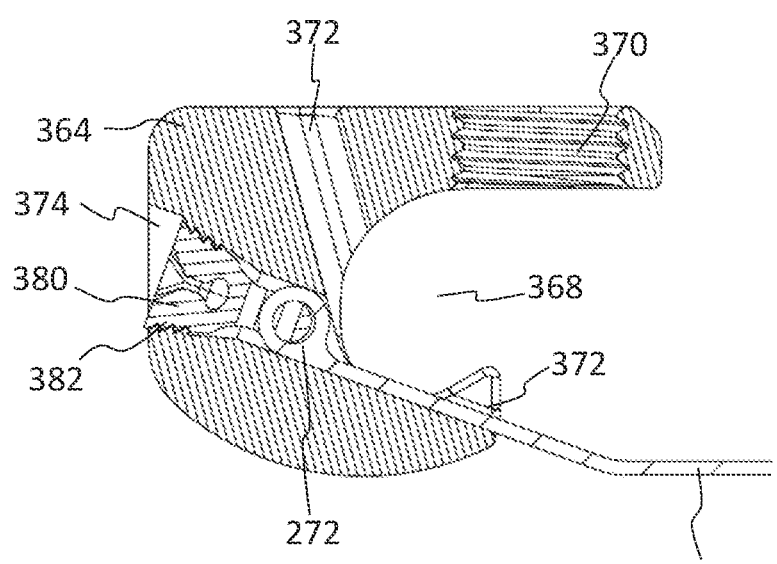

With emphasis on FIG. 37A, the main body 364 defines a band slot 372 perpendicular to the axis of the spinal rod 14. The band slot 374 may slope from a rear of the implant 362 towards rod slot 368. The band slot 372 may extend from an upper surface of the implant 362 into fluid communication with the rod slot 368. The band slot 372 may terminate below the rod slot 368 near the bottom of the implant 362. The main body 364 of the implant 362 further defines an internal recess 374 configured to receive an anchor or buckle 380. The internal recess 374 intersects the band slot 372 and the rod slot 368. The internal recess 374 extends from a rear of the main body 364 and is angled or sloped downward and into the rod slot 368. The internal recess 374 includes one or more grooves 376 configured to secure the buckle 380 in the implant 362.

The main body 364 of the band clamp 362 may include one or more engagement recesses 378 for engagement with an insertion and/or tensioning instrument. For example, two opposed engagement recesses 378 may be defined within the side surfaces near the rear of the implant 362. Each of the engagement recesses 378 may include a slot terminating in a circular divot, for example. It will be appreciated that other suitable engagement features may be used to temporarily couple the implant 362 to an instrument, such as inserter or tensioner.

As previously described for FIG. 23A, the flexible band may have two free ends 270, 272 with a middle portion 274 in between. The middle portion 274 of the flexible band 12 is intended to contact bone. One free end 270 of the flexible band 12 may be optionally attached to a malleable leader 276, which can be fed around anatomy to wrap the flexible band 12 around the anatomy. The second free end 272 of the flexible band 12 is attached to the buckle 380.

Similar to buckle 278, the buckle 380 may be conical in shape with grooves 382 for engagement with grooves 376 in the mating recess 374 in the main body 364 of the implant 362. The buckle 380 may include a flexure cut configured to allow the outer geometry to squeeze into the mating recess 374. When the grooves 382 on the buckle 380 align with the grooves 376 in the recess 374, the flexure allows the buckle 380 to spring back to its original shape, thus preventing disassembly. The buckle 380 may also include a loop, around which the flexible band 12 may be attached. The internal recess 374 in the main body 364 may accept the flexible band 12. The internal recess 374 has grooves 376 that mate with the grooves 382 on the buckle 380. The flexible band 12 is passed thru the recess 374 and the buckles 380 snaps into the mating grooves 376. After assembly, the flexible band 12 is securely attached to the main body 364 at one end.

Figure 38A:
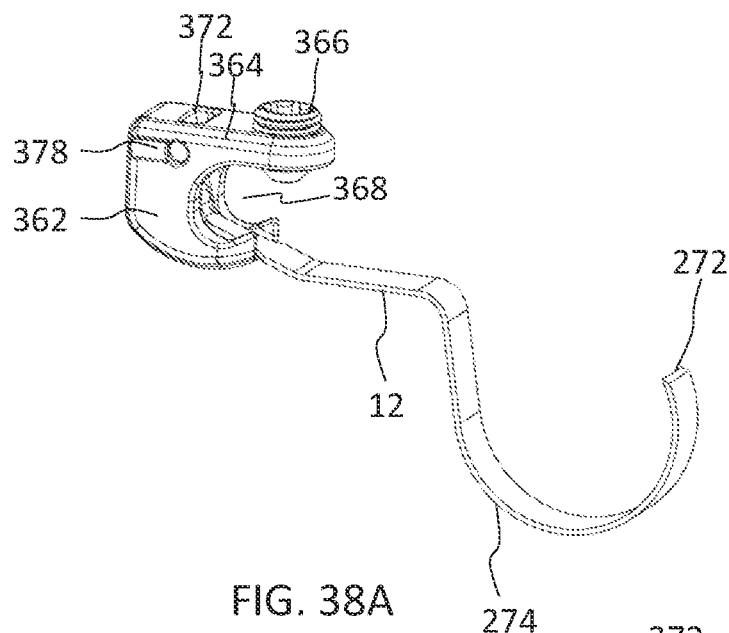
FIGS. 38A-38C show perspective views of the implant and band assembly, the band passed back through the implant to create a loop, and the implant assembly locked to the spinal rod.
Figure 38B:
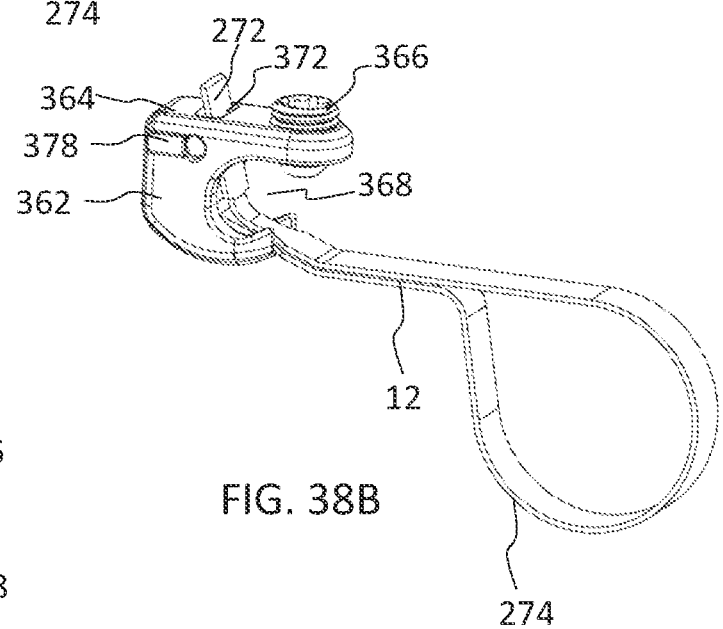
Figure 38C:
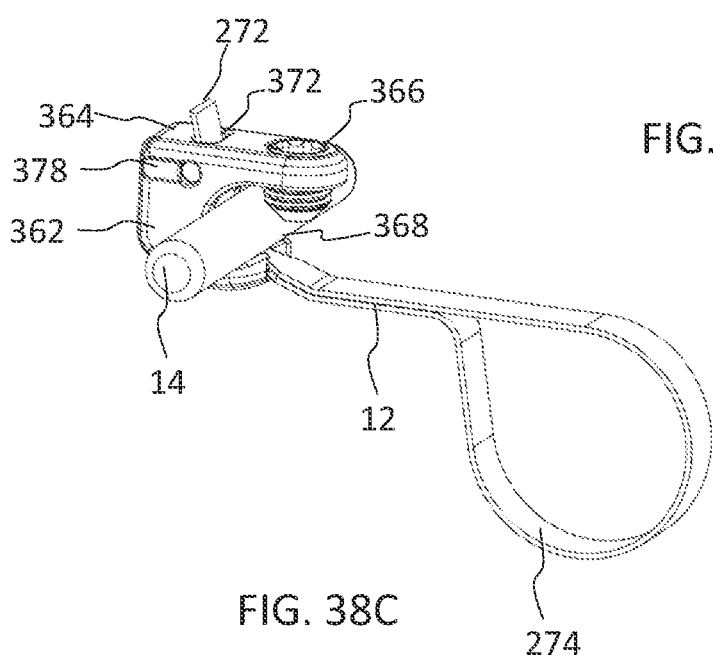
Figure 39:
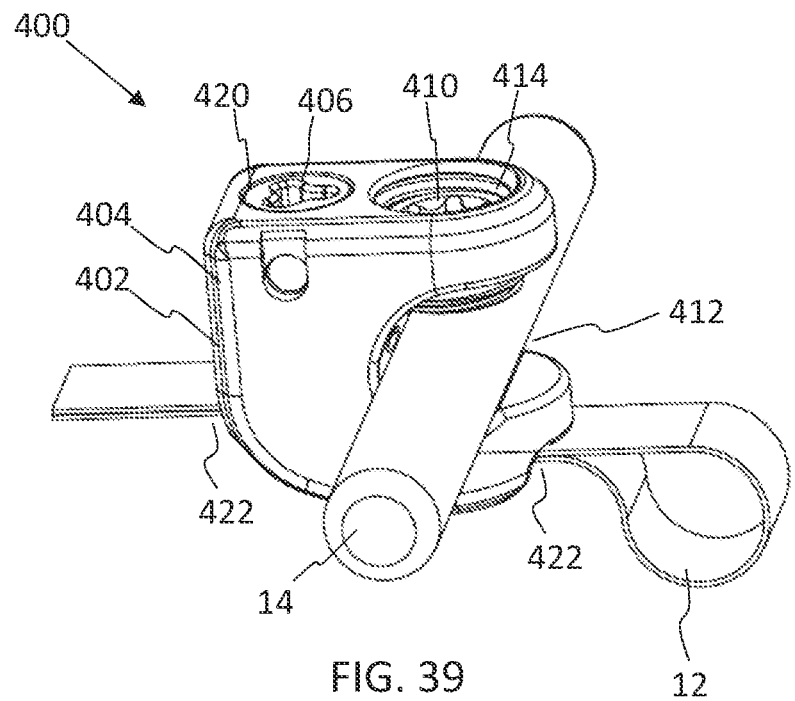
FIG. 39 shows a perspective view of an implant system configured to secure the flexible band to the spinal rod according to one embodiment.
Figure 40:
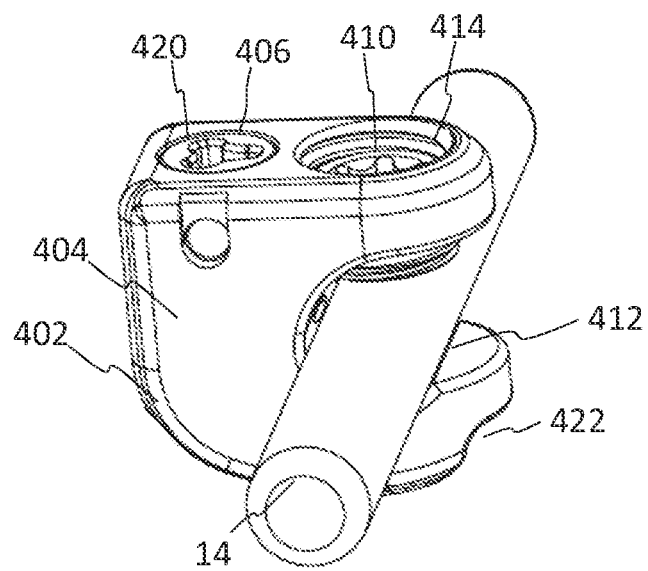
FIG. 40 shows a perspective view of the implant of FIG. 39 attached to the spinal rod.

As shown in FIGS. 38A-38C, the flexible band 12 is passed through the recess 374 in the main body 364 until the buckle 380 snaps into place and the flexible band 12 is secured to the main body 364. As shown in FIG. 38A, the band 12 travels beneath the rod slot 368, and the free end 274 of the flexible band 12 is passed around the bony anatomy. As shown in FIG. 38B, the free end 274 is passed back into the main body 364, beneath the rod slot 368 and up through the band slot 372 to create a loop. As shown in FIG. 38C, the implant 362 is placed onto the spinal rod 14 and the set screw 366 is partially tightened to provisionally secure the spinal rod 14 into the rod slot 368 of the implant 362. The partial tightening allows the flexible band 12 to slide freely through the band slot 372. A tensioning device may be used to apply tension to the free end 272 of the band 12. The loop is tensioned to provide fixation to the bone. Then, the set screw 366 is final tightened. Final tightening of the set screw 366 forces the rod 14 to contact the flexible band 12, locking the tension in the loop, as well as securing the implant 362 to the spinal rod 14.

Turning now to FIGS. 39-45B, a band clamp implant assembly or system 400 is shown according to one embodiment. Similar to implant system 362, the implant 402 is configured to connect the flexible band 12 to the spinal rod 14 in order to provide fixation to the spine. The band 12 is wrapped around bony anatomy, such as the lamina or transverse process, and then a tensile force is applied to translate the spine to the spinal rod 14. After sufficient translation has been achieved to correct the deformity, the tensioned band 12 is locked to the spinal rod 14 with the band clamp 402. Bands 12 may be advantageous in pediatric and neuromuscular deformity cases due to the high prevalence of weak bone and dysmorphic vertebrae which may make pedicle screw placement difficult or impossible.

Figure 41A:
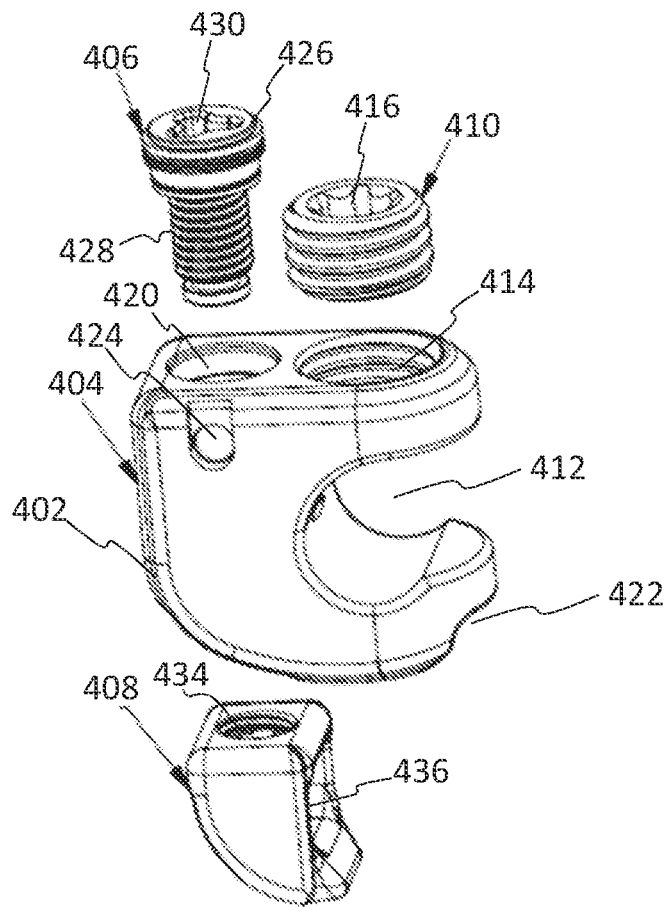
FIGS. 41A-41B show exploded and assembled views, respectively, of the implant of FIG. 40.
Figure 41B:
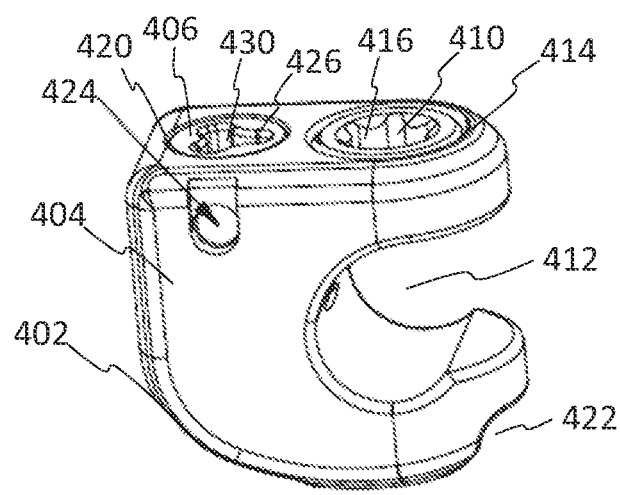

As shown in FIGS. 41A-41B, the implant 402 includes an implant housing 404, drive screw 406, clamp 408, and locking cap 410. The implant housing 404 has a rod slot 412 configured to accept the spinal rod 14 and a through hole 414, which intersects the rod slot 368. The rod 14 may be side loaded into the rod slot 412. The hole 414 may be generally in line with the rod slot 412 such that a hole axis of the hole 414 is generally perpendicular to the long axis of the rod 14. The hole 414 may define threads therein. The locking cap 410 is configured to engage the rod 14 located in the rod slot 412 to fix the rod 14 relative to the implant housing 404. The locking cap 410 may be in the form of a threaded set screw with a recess 416 in the upper surface of the locking cap 410 configured to receive a driver instrument. When rotated, the locking cap 410 is able to thread up and down within the threaded hole 414 in order to reversibly interfere with the rod slot 412. The lower surface of the locking cap 410 may be generally planar in order to press against the rod 14. In a locked position, the lower surface of the locking cap 410 contacts the rod 14, thereby securing the rod 14 in the rod slot 412.

As shown in FIGS. 42A-42D, the implant housing 404 has an elongate channel 418, a pocket 420, and a groove 422. The channel 418 is configured to accept the clamp 408 and the pocket 420 is configured to accept the drive screw 406. The pocket 420 may extend from an upper surface of the housing 404 and into fluid communication with the channel 418. The channel 418 may extend from the pocket 420 and through to the lower surface of the housing 404. The channel 418 and pocket 420 may be coaxial along axis D. The hole axis of the hole 414 for the locking cap 410 may be generally parallel to axis D. The groove 422 in the implant housing 404 is configured to receive the flexible band 12. The groove 422 is located beneath the rod slot 412. The groove 422 in the implant housing 404 is positioned such that the groove 422 intersects the implant passage 436 in the clamp 408.

The housing 404 of the band clamp 402 may include one or more engagement or holding recesses 424 for engagement with an insertion and/or tensioning instrument. For example, two opposed engagement recesses 424 may be defined within the side surfaces near the rear of the implant 402. Each of the engagement recesses 424 may include a slot from the upper surface and terminating in a circular divot, for example. It will be appreciated that other suitable engagement features may be used to temporarily couple the implant 402 to an instrument, such as inserter and/or tensioner.

The drive screw 406 includes an enlarged head 426 and a shaft 428. The head 426 may be define an instrument recess 430 in an upper surface configured to engage an instrument, such as a driver. Instrument recess 430 in the drive screw 406 may be different than instrument recess 416 in the locking cap 410. The shaft 428 may be threaded along its length. As shown in FIGS. 42C-42D, the drive screw 406 may engage the clamp 408 such that the clamp 408 is able to translate within the channel 418 in the implant housing 404 between a first position and a second position.

Figure 43:
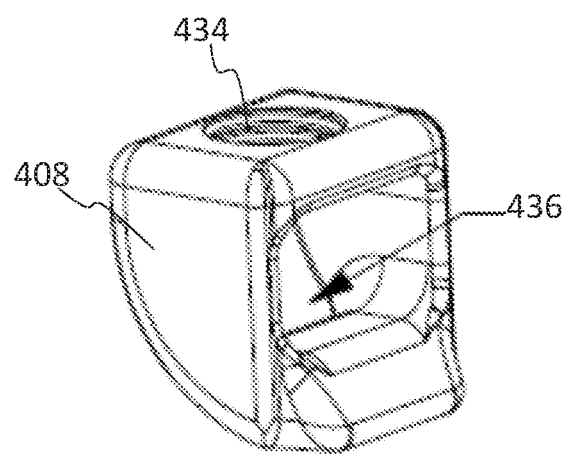
FIG. 43 shows the clamp for securing the band within the implant.

As shown in FIG. 43, the clamp 408 includes a bore 434 configured to accept the shaft 428 of the drive screw 406 and an intersecting implant passage 436 configured to accept the flexible band 12. The bore 434 extends from an upper surface of the clamp 408 and into fluid communication with the passage 436. The bore 434 may be at least partially threaded to engage the external threads of the shaft 428 of the drive screw 406. The passage 436 extends through the body of the clamp 480.

Figure 44A:
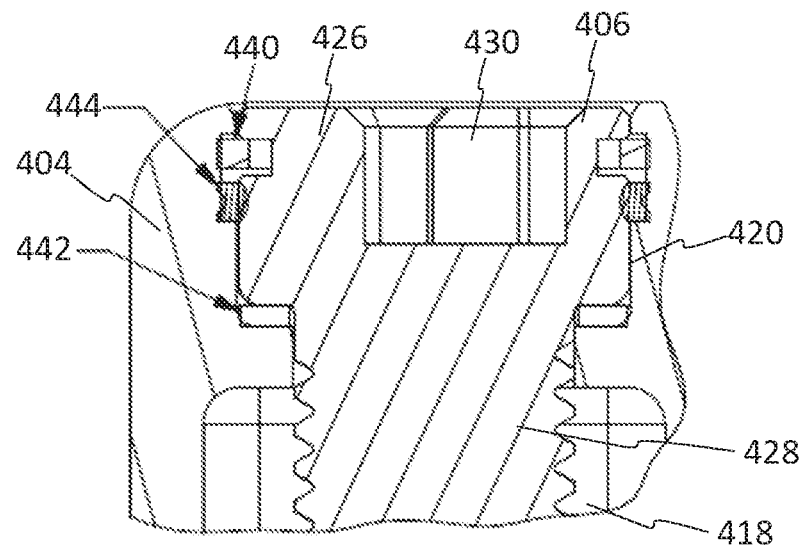
FIGS. 44A-44B show partial cross-sectional views of the drive screw in the implant.
Figure 44B:
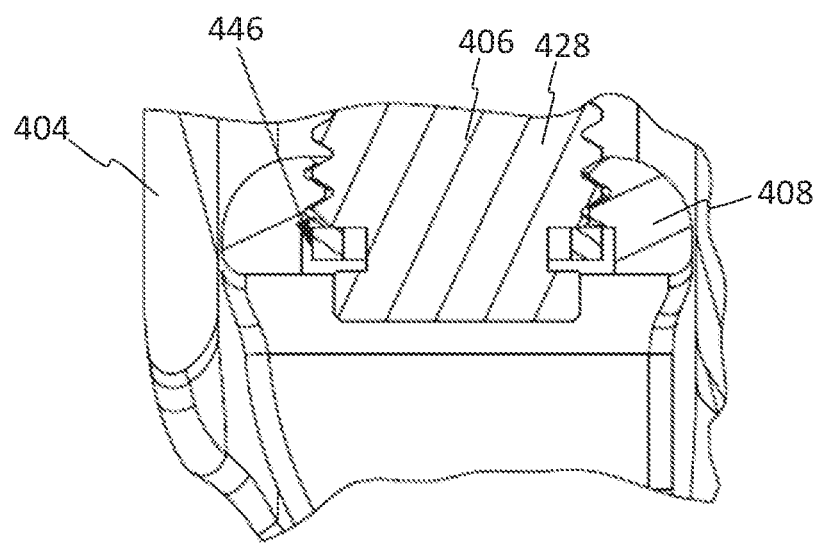

With emphasis on FIGS. 44A-44B, the pocket 420 in the implant housing 404 and the head 426 of the drive screw 406 each contain a groove configured to accept a first retaining ring 440. The first retaining ring 440 holds the drive screw 406 in position within the implant housing 404. The drive screw 406 is able is rotate freely about its long axis but may not translate within the implant housing 404. The implant 402 may optionally include a thrust washer 442 located between the head 426 of the drive screw 406 and the bottom of the pocket 420 in the implant housing 404. The implant 402 may also optionally include a drag ring 444 located around the head 426 of the drive screw 406 within the pocket 420 of the implant housing 404. The drag ring 444 may be positioned between the retaining ring 440 and the thrust washer 442. The clamp 408 may define a counter bore and the distal end of the drive screw 406 may define a groove configured to accept a second retaining ring 446. The second retaining ring 446 prevents the clamp 408 from disengaging from the drive screw 406 after assembly.

Figure 45A:
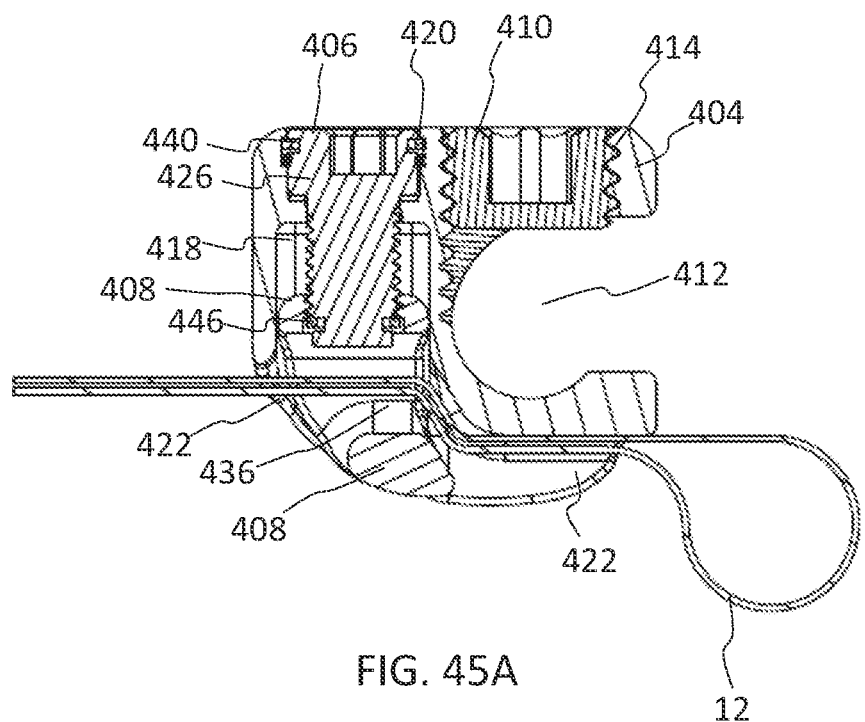
FIGS. 45A-45B shows cross-sectional views of the band threaded through the implant with the clamp in an unlocked position and a locked position, respectively.
Figure 45B:
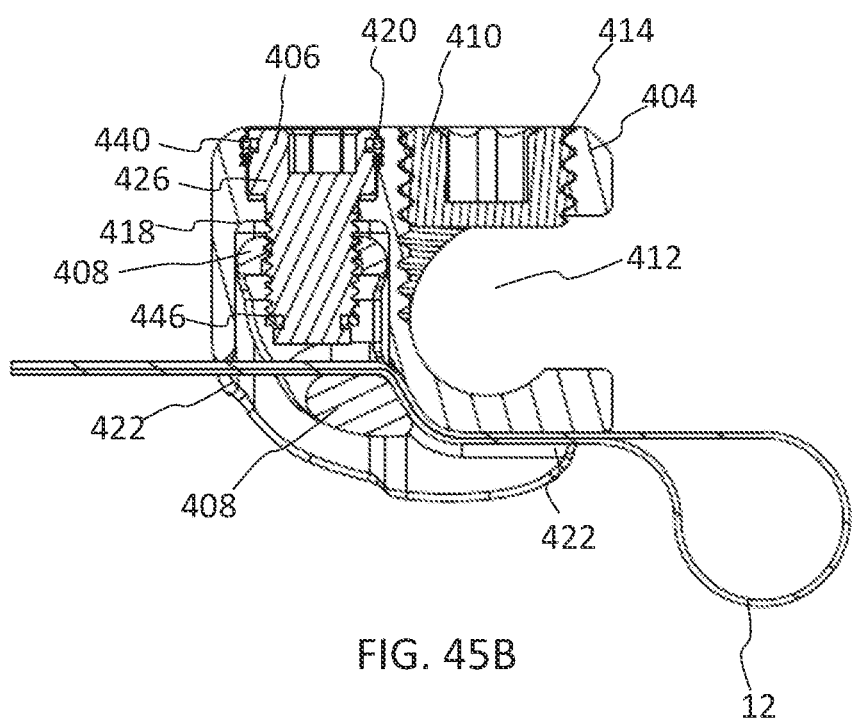

With emphasis on FIGS. 45A-45B, the implant housing 404 and the clamp 408 each have a surface configured to contact the flexible band 12. The implant housing 402 has geometry such that the distance between these surfaces changes depending on where the clamp 408 is located within the channel 418 in the implant housing 404. As shown in FIG. 45A, when the clamp 408 is located in a first unlocked position within the channel 418 in the implant housing 404, the distance between the surfaces is of sufficient space for the flexible band 12 to pass thru the implant passage 436 in the clamp 408. As shown in FIG. 45B, when the clamp 408 is located in a second locked position within the channel 418 in the implant housing 404, the distance between the surfaces is decreased such that the surfaces contact and pinch the flexible band 12, thereby securing the band 12 in the implant 402.

According to one embodiment, a method of securing the flexible band 12 may involve one or more of the following steps in any suitable order: (1) feeding a free end of flexible band 12 into the rear of the implant housing 404 through the band slot 422 and out through the front of the implant housing 404; (2) passing the free end of the flexible band 12 around bony anatomy creating a loop that contacts bone; (3) passing the free end of the flexible band 12 back into the same band slot 422 at the front of the housing 404 beneath the rod slot 412 and though to the back of the housing 404; (4) tensioning the flexible band 12 by providing a tensile force to the free end(s) of the flexible band 12 thereby causing the loop to become tight around the bony anatomy; (5) rotating the drive screw 406 to move the clamp 408 to the locked position, thereby securing the flexible band 12 in the clamp 408; and (6) cutting and removing any excess length of the flexible band 12 near the rear of the housing 404. This method allows surgeons to achieve correction and fixation of a spinal deformity. This technique may be advantageous in pediatric and/or neuromuscular deformity cases when traditional pedicle screw fixation is compromised or not possible due to the presence of weak bone or dysmorphic vertebrae.

Turning now to FIGS. 46-50B, a band clamp implant assembly or system 460 is shown according to one embodiment. The implant 462 is configured to lock the flexible band 12 in tension without the presence of a spinal rod. Sublaminar bands 12 may be used to provide posterior fixation of the spine as an alternative or supplement to pedicle screw instrumentation. The implant 462 may be useful in patients with poor bone quality or difficult anatomy where the interface between bone and implant is compromised. For example, patients with pediatric deformity may present with dysmorphic vertebrae, which restrict the use of pedicle screws. The risk of screw pullout may be increased in patients with osteoporosis due to weak connection between the bone and the implant. Additionally, sublaminar bands 12 may be used in cases where patients present with fractured anatomy. The band 12 may wrapped around the fracture site, such as C2 fracture(s) of the odontoid, and tensioned to provide fixation and promote healing. In these clinical scenarios, it may be advantageous to have implants 462 which lock the sublaminar band 12 in tension.

Figure 46A:
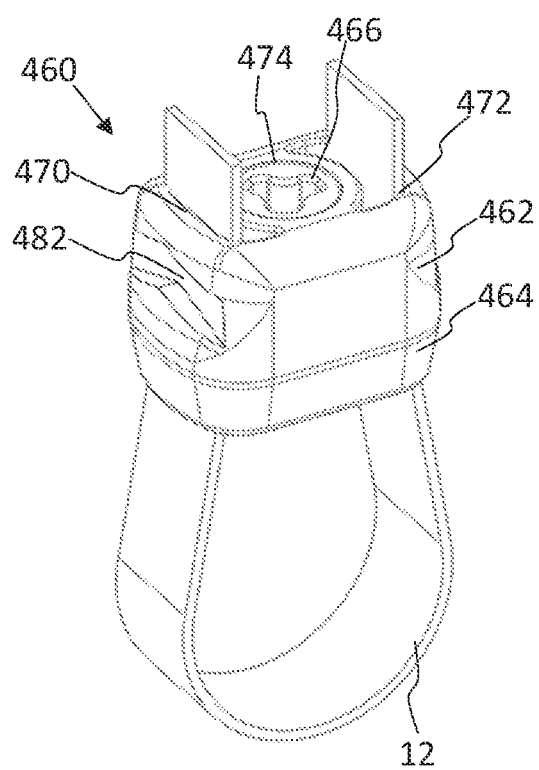
FIG. 46A-46B show a perspective view and an exploded view, respectively, of an implant system configured to lock a flexible band in tension without the presence of a spinal rod according to one embodiment.
Figure 46B:
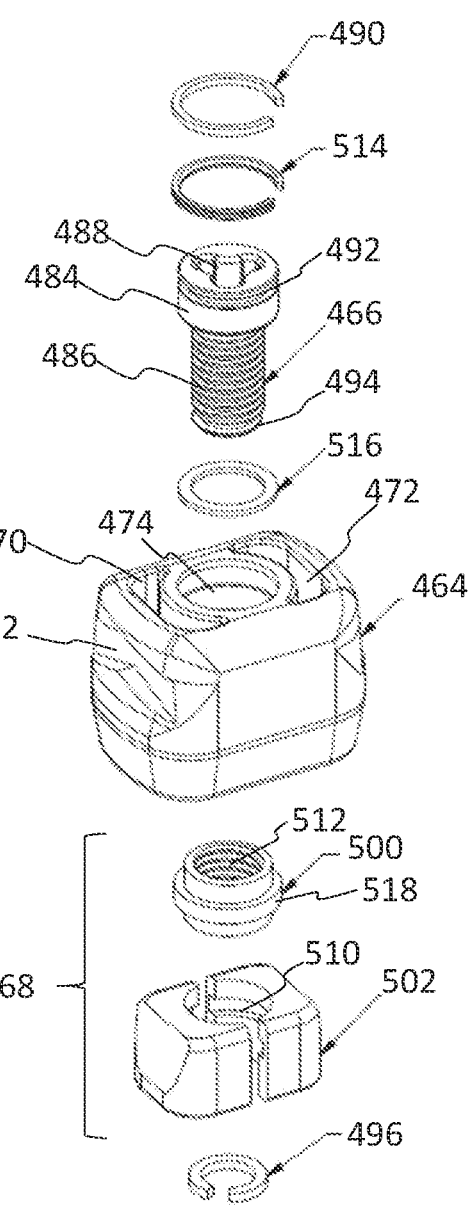
Figure 47A:
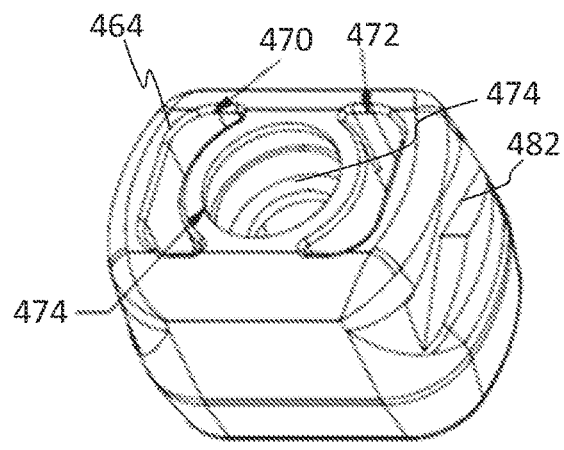
FIGS. 47A-47B show perspective and cross-sectional views, respectively, of the implant of FIGS. 46A-46B.
Figure 47B:
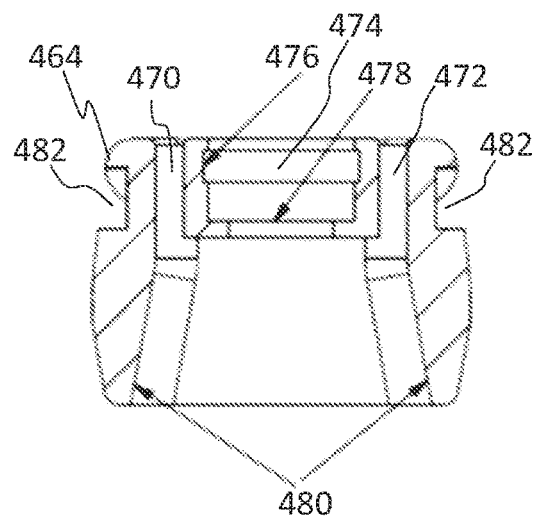

As shown in FIGS. 46A-46B, the implant 462 may include an outer body 464, a drive screw 466, and a clamping assembly 468. With emphasis on FIG. 47A, the outer body 464 defines first and second band slots 470, 472 configured to accept the flexible band 12. The band slots 470, 472 may each extend from the upper surface to the lower surface of the body 464. The band slots 470, 472 may be elongated in width to accommodate the flat profile of the band 12. With emphasis on FIG. 47B, the outer body 464 defines a recess 474 extending from the upper surface to the lower surface of the body 464. The recess 474 includes a pocket 476 and a through hole 478, where the drive screw 466 rests. The band slots 470, 472 and recess 474 may form ramped surfaces 480 toward a lower portion of the body 464. The ramped surfaces 480 may be angled such that they have a narrow width toward the top of the body 464 and a greater width toward the bottom of the body 464.

The outer body 464 defines one or more engagement recesses 482 configured to mate with an instrument for providing tension to the flexible band 12 before locking. For example, two opposed engagement recesses 482 may be defined within the side surfaces near the top of the implant 462. It will be appreciated that other suitable engagement features may be used to temporarily couple the implant 462 to an instrument, such as inserter and/or tensioner.

The drive screw 466 includes an enlarged head 484 and a shaft 486. The head 484 may be define an instrument recess 488 in an upper surface configured to engage an instrument, such as a driver. The shaft 486 may be threaded along its length. The drive screw 466 is retained within the outer body 464 by a first retaining ring 490. The drive screw retaining ring 490 may be in the form of a split ring. The split ring 490 may sit in a groove 492 in the head 484 of the drive screw 466.

Figure 48:
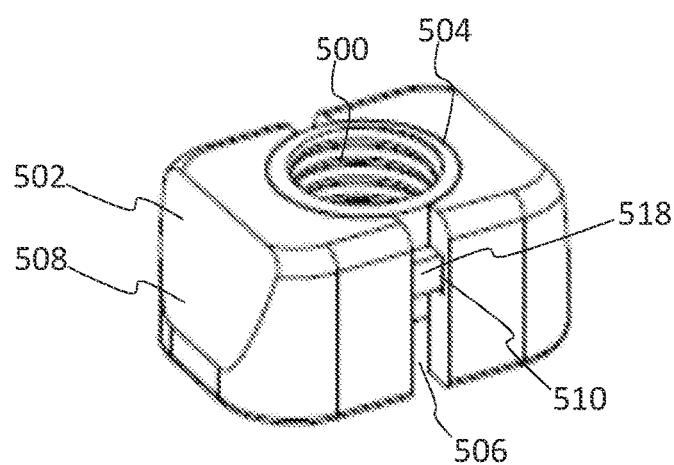
FIG. 48 is a perspective view of the carriage and clamp of the clamping assembly of the implant.

With emphasis on FIG. 48, the clamping assembly 468 includes a carriage 500 and a clamp 502. The clamp 502 is split into two halves defining a cylindrical opening 504 for receiving the carriage 500. When assembled with the carriage 500, the two halves of the clamp 502 may be separated by a gap 506. The side surfaces of the clamp 502 may be angled surfaces 508, which mimic the ramped surfaces 480 in the body 464 of the implant 462. The opening 504 defines an internal groove 510 configured to engage the carriage 500. The carriage 500 defines a generally cylindrical body with a central hole 512 extending from the upper surface to the lower surface of the carriage 500. The central hole 512 may be threaded such that the clamping assembly 468 may threaded onto the drive screw 466. The distal end of the drive screw 466 has a groove 494, in which a second retaining ring 496 sits. The second retaining ring 496 may be in the form of a split ring, which prevents the clamping assembly 468 from threading off of the drive screw 466. The carriage 500 may define an exterior annulus 518 forming a middle band around the center of the carriage 500. The annulus 518 may be received within the groove 510 in the clamp 502, thereby connecting the clamp 502 to the carriage 500.

The implant 462 may optionally include a drag ring 514 located around the head 484 of the drive screw 466 within the pocket 476 of the body 464. The drag ring 514 may be in the form of a split ring. The implant 462 may also optionally include a friction ring 516 to impart friction to the drive screw 466. The friction ring 516 may be in the form of a washer located between the head 484 of the drive screw 466 and the bottom of the pocket 476 in the body 464 of the implant 462.

Figure 49A:
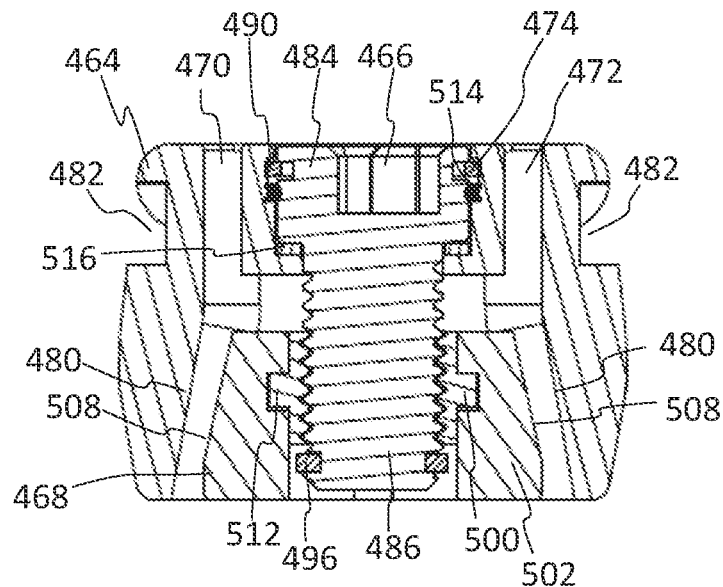
FIGS. 49A-49B show cross-sectional views of the implant with the locking assembly in unlocked and locked positions, respectively.
Figure 49B:
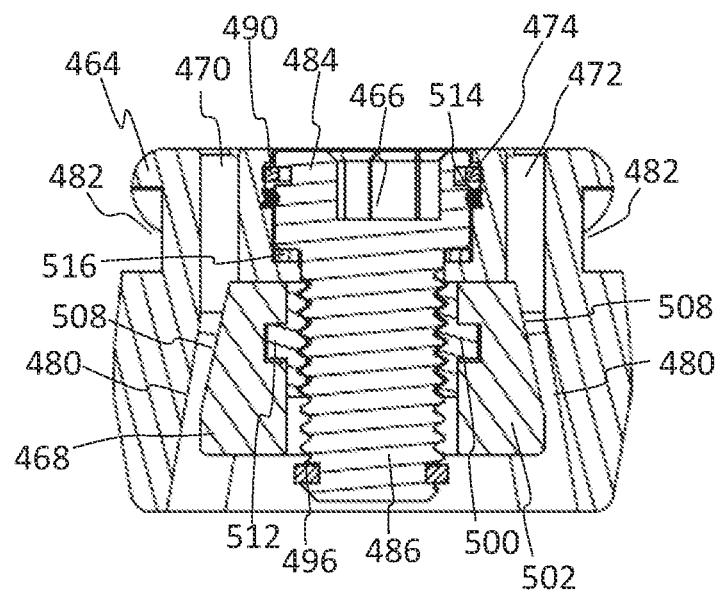

With emphasis on FIGS. 49A-49B, when the drive screw 466 is actuated, the clamping assembly 468 may translate up and down. As shown in FIG. 49A, the inner surface of the outer body 464 and the outer surface of the clamp 502 have mating ramped geometries 480, 508 such that there is clearance for the flexible band 12 to pass through the implant 462 when the clamping assembly 468 is in a first open position. In the open position, the clamping assembly 468 is in a downward location to allow the band 12 to pass through the band slots 470, 472. As shown in FIG. 49B, actuation of the drive screw 466 translates the clamping assembly 468 into a locked second position, in which the clamping assembly 468 contacts the flexible band 12 against the inner surface of the outer body 464, thus locking the band 12. In the locked position, the clamping assembly 468 is in an upward location which pinches the band 12 between the clamp 502 and the body 464 of the implant 462.

Figure 50A:
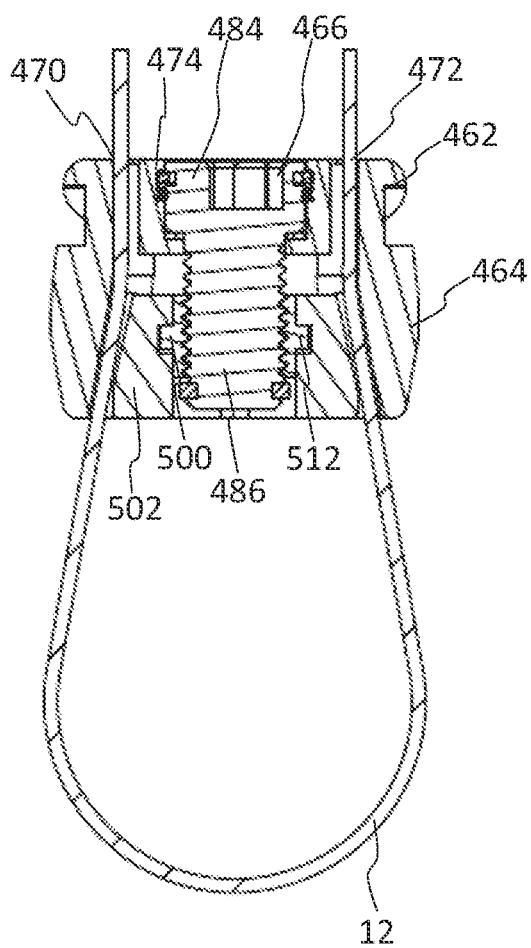
FIGS. 50A-50B show cross-sectional view of the implant with the band in the unlocked and locked positions, respectively.
Figure 50B:
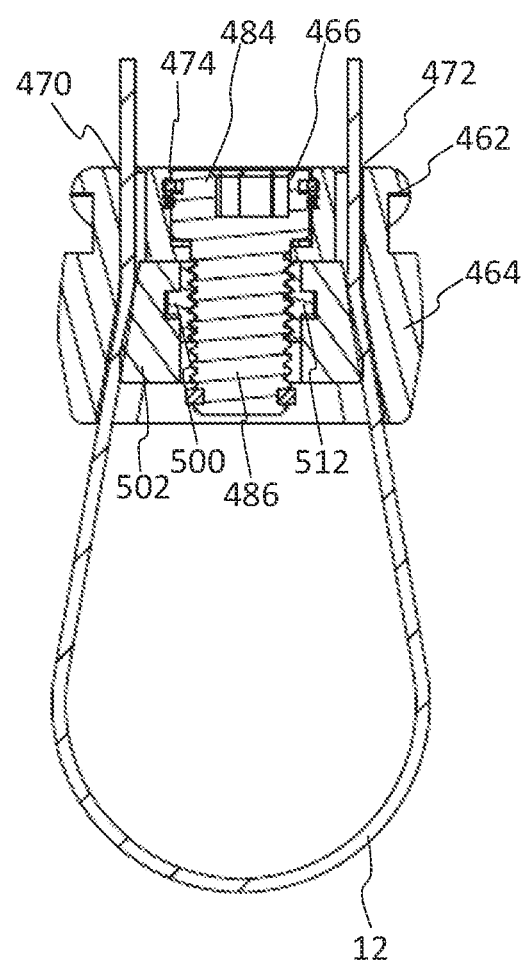

According to one embodiment, a method of securing the flexible band 12 to the spinal rod 14 may involve one or more of the following steps in any suitable order: (1) while the clamping assembly 468 is in a downward open position as shown in FIG. 50A, feeding a free end of flexible band 12 through the first band slot 470; (2) passing the other free end of the flexible band 12 around bony anatomy creating a loop that contacts bone; (3) passing the other free end of the flexible band 12 through the second band slot 472; (4) tensioning the flexible band 12 by providing a tensile force to the free end(s) of the flexible band 12 thereby causing the loop to become tight around the bony anatomy; (5) rotating the drive screw 466 to move the clamp 502 upward into the locked position as shown in FIG. 50B, thereby securing the flexible band 12 in the implant 462; and (6) cutting and removing any excess length of the flexible band 12.

Figure 51A:
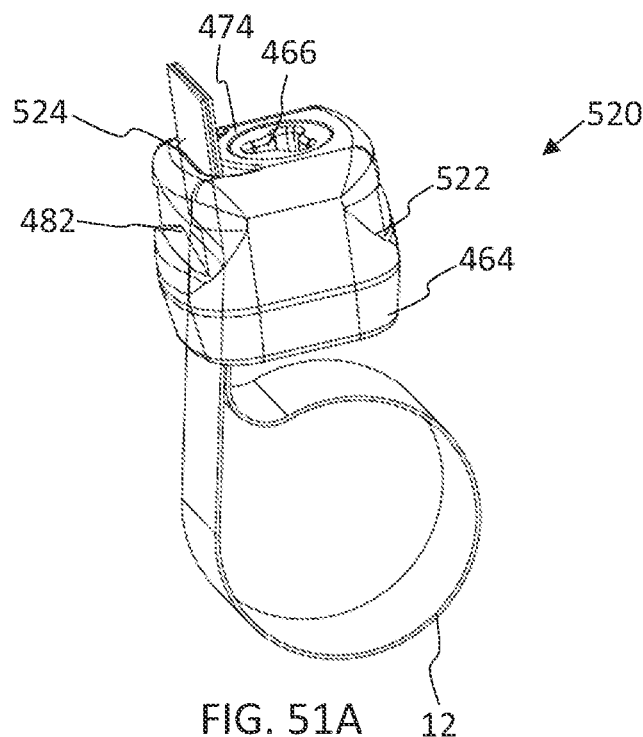
FIGS. 51A-51C show an embodiment of an implant with a single thru hole to accept the band.
Figure 51B:
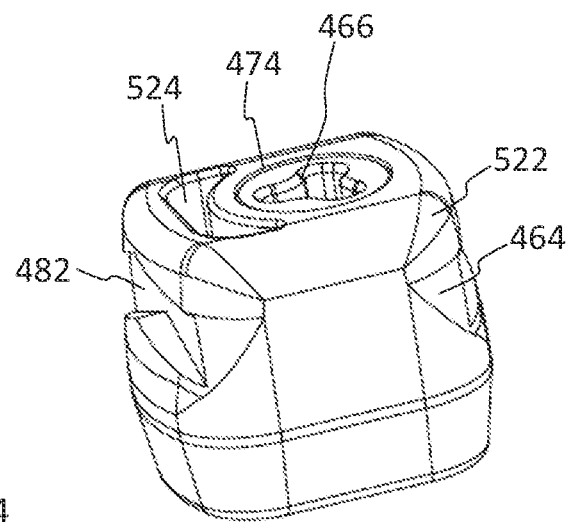
Figure 51C:
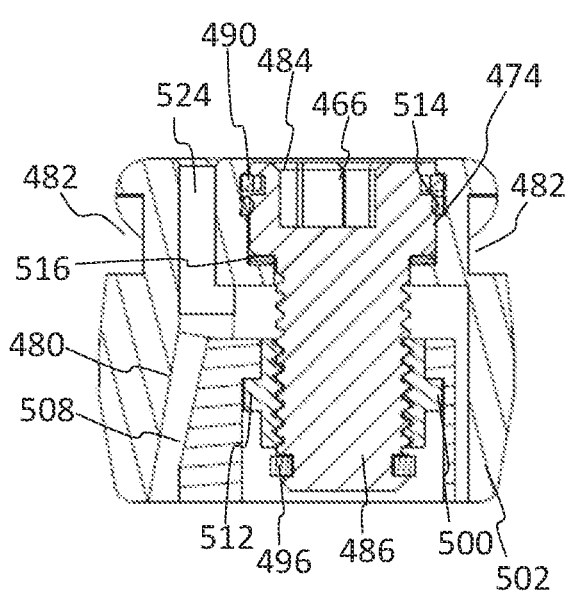

Turning now to FIGS. 51A-51C, a band clamp implant assembly or system 520 is shown according to one embodiment. Implant 522 is similar to implant 462 except only a single band slot 524 is provided, which accepts both ends of the band 12. The single band slot 524 extends from the top to the bottom of the implant 522. Actuation of the drive screw 466 causes the clamping assembly 468 to translate up and down within the implant 522. In FIG. 51C, the clamping assembly 468 is shown in the open configuration with the clamp 502 positioned downward in the body 464. The band 12 may be threaded through the single band slot 524, wrapped around bone, and then threaded back through the same band slot 524. After tensioning the band 12, the clamping assembly 468 may be moved upward to lock the band 12. The ramped geometry 508 of the clamp 502 contacts the band 12 and secures the band 12 against the ramped geometry 480 of the outer body 464. Since the opposite side of the clamp 502 and recess 474 is absent the second band slot, the mating geometry may be generally planar or of other suitable configuration.

Turning now to FIGS. 52-55, a band clamp implant assembly or system 530 is shown according to one embodiment. Similar to implant 522, the implant 532 includes a single band slot 538, which accepts both ends of the band 12. In this embodiment, a rotatable cam lock 536 is used to secure the band 12 in the implant 532.

Figure 52:
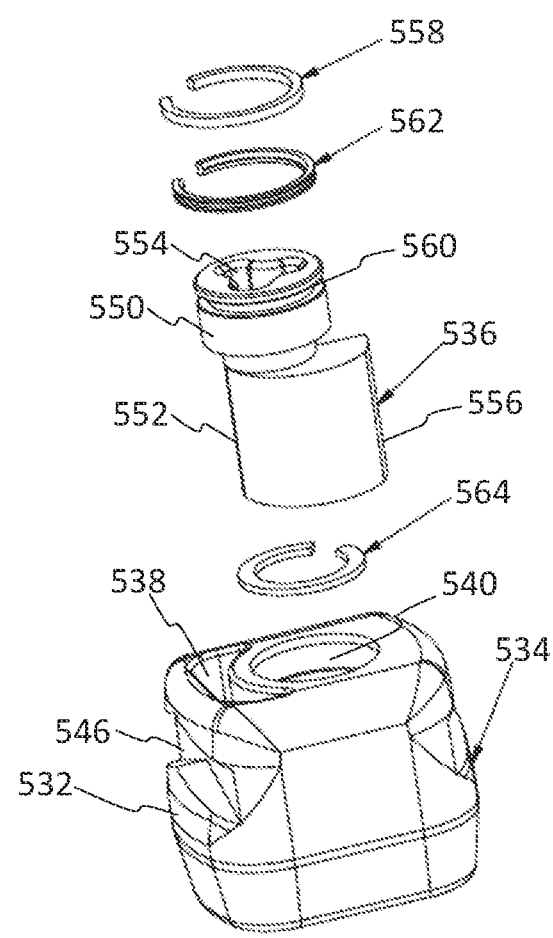
FIG. 52 is an exploded view of an implant having a cam lock according to one embodiment.

With emphasis on FIG. 52, the implant 532 includes an outer body 534 and a cam lock 536. The outer body 534 has a band slot 538 configured to accept the flexible band 12. The band slot 538 may extend from the upper surface to the lower surface of the body 534. The band slot 538 may be elongated in width to accommodate the flat profile of the band 12. The outer body 534 defines a recess 540 extending from the upper surface to the lower surface of the body 534. The recess 540 includes a pocket 542 and a through hole 544, where the cam lock 536 rests. The outer body 534 may include one or more engagement recesses 546 configured to mate with an instrument for providing tension to the flexible band 12 before locking.

The cam lock 536 may include a head 550 with a cam body 552. The head 550 may be define an instrument recess 554 in an upper surface configured to engage an instrument, such as a driver. The cam body 552 is offset relative to the longitudinal axis of the head 550 such that a cam engagement surface 556 projects laterally outward. The cam lock 536 is retained within the outer body 534 by a retaining ring 558. The cam lock retaining ring 558 may be in the form of a split ring. The split ring 558 may sit in a groove 560 near the top of the head 550 of the cam lock 536.

The implant 532 may optionally include a drag ring 562 located around the head 550 of the cam lock 536 and within the pocket 542 of the body 534. The drag ring 562 may be in the form of a split ring located beneath the retaining ring 558. The implant 532 may also optionally include a friction ring 564 to impart friction to the cam lock 536. The friction ring 564 may be in the form of a split ring located between the head 550 of the cam lock 536 and the bottom of the pocket 542 in the body 534 of the implant 532.

Figure 53A:
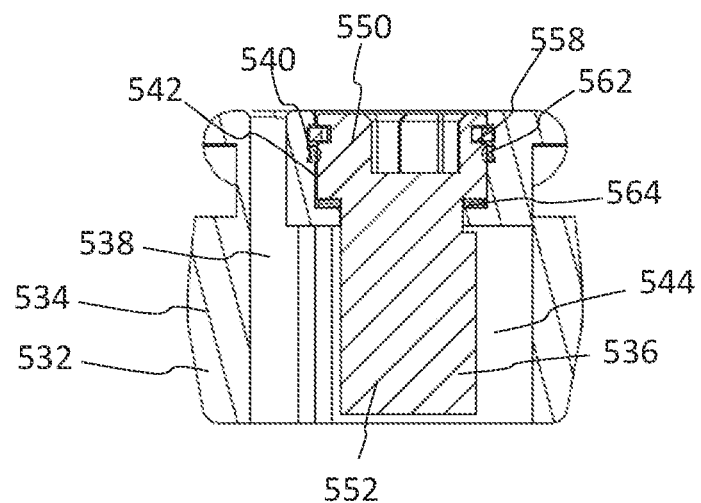
FIGS. 53A-53B show cross-sectional views of the cam lock in unlocked and locked positions, respectively.
Figure 53B:
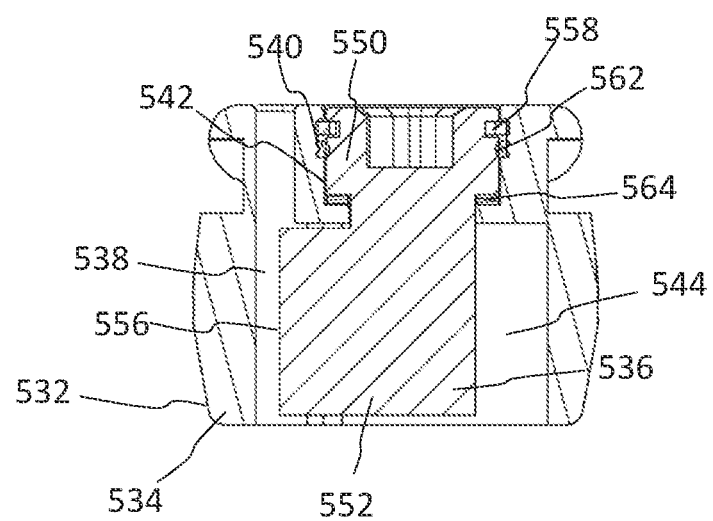
Figure 54A:
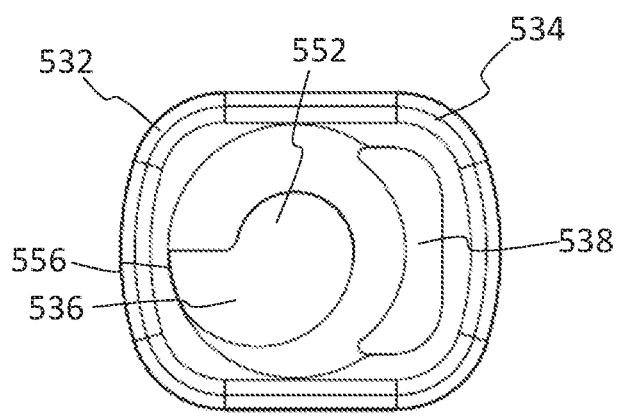
FIGS. 54A-54B show bottom views of the implant with the cam lock in unlocked and locked positions, respectively.
Figure 54B:
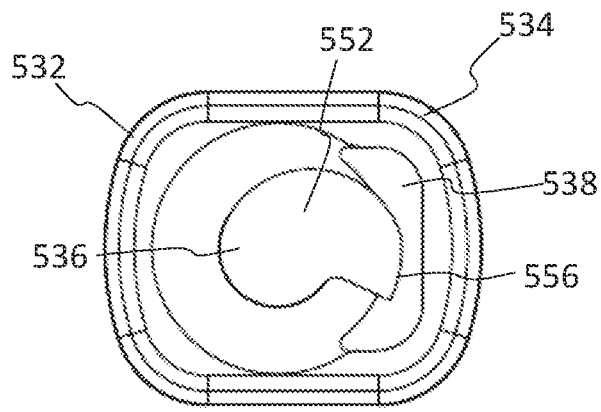

With emphasis on FIGS. 53A-53B, the cam lock 536 may be rotated into and out of engagement with the band slot 538 to secure the band 12 therein. As shown in FIG. 53A, the cam lock 536 may turn within the outer body 534 such that there is space to pass the flexible band 12 through the slot 538 in the outer body 534 when the cam lock 536 is in a first open position. As shown in FIG. 53B, when the cam lock 536 is actuated, the cam surface 556 is configured to contact the flexible band 12 against the inner surface of the outer body 534, thereby locking the band 12 in the implant 532. FIG. 54A shows a bottom view of the implant 532 with the cam lock 536 in the unlocked position, thereby allow the band 12 to pass freely through slot 538. FIG. 54B shows the implant 532 with the cam lock 536 in the locked position, thereby locking the band 12 in the implant 532.

Figure 55:
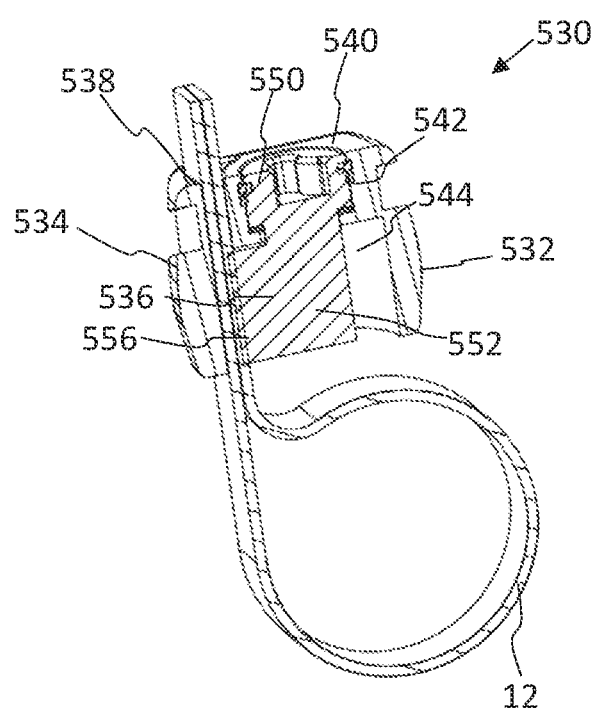
FIG. 55 is a cross-sectional view of the implant with the cam lock in the locked position securing the band.

According to one embodiment, a method of securing the flexible band 12 to bone may involve one or more of the following steps in any suitable order: (1) while the cam body 552 is in its open position, feeding a free end of flexible band 12 through the band slot 538; (2) passing the free end of the flexible band 12 around bony anatomy creating a loop that contacts bone; (3) passing the free end of the flexible band 12 back through the same band slot 538; (4) tensioning the flexible band 12 by providing a tensile force to the free end(s) of the flexible band 12 thereby causing the loop to become tight around the bony anatomy; (5) rotating the cam lock 536 to move the cam body 552 into the locked position as shown in FIG. 55, thereby securing the flexible band 12 in the implant 532; and (6) cutting and removing any excess length of the flexible band 12.

Figure 56A:
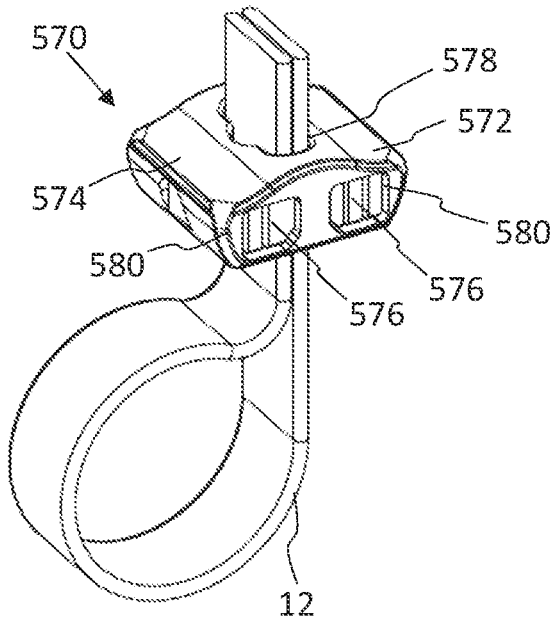
FIGS. 56A-56C show an embodiment of an implant including a housing and two spring blocks for securing the band.
Figure 56B:
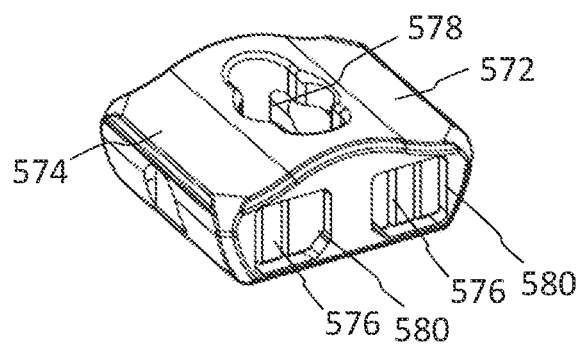
Figure 56C:
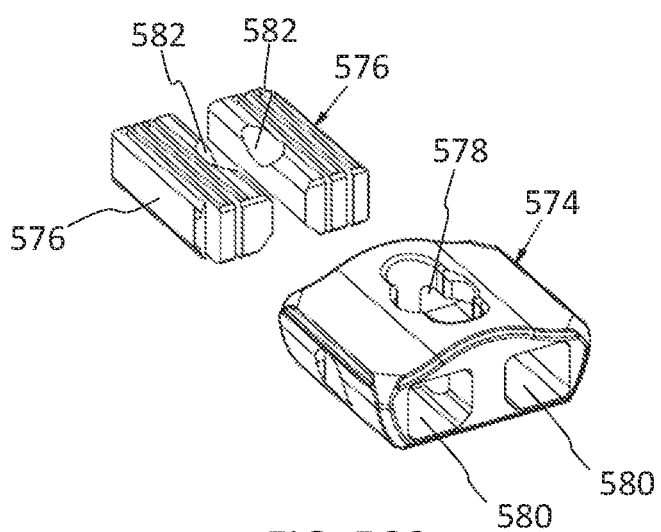

Turning now to FIGS. 56A-56C, a band clamp implant assembly or system 570 is shown according to one embodiment. Similar to implant 532, the implant 572 includes a single band slot 578, which accepts both ends of the band 12. In this embodiment, one or more spring blocks 576 are used to secure the band 12 in the implant 572.

The implant 572 includes a housing 574 and a pair of spring blocks 576. The band slot 578 in the housing 574 is configured to accept the flexible band 12. The band slot 578 may extend from an upper surface to a lower surface of the housing 574. The housing 574 may be bowed or convex along the upper surface. A pair of parallel openings 580 may extend from the front to the back of the housing 574 on either side of the band slot 578. The openings 580 may be in fluid communication with the band slot 574. The openings 580 may be oriented generally perpendicular to the band slot 578.

The spring blocks 576 may include a plurality of cuts or slits or may comprise a shape-memory material, for example, configured to allow the blocks 576 to be deformed. After deformation, the blocks 576 are then able to return to their original shape. Each of the springs blocks 576 may define a generally quadrilateral cuboid body. For example, the spring blocks 576 may have generally rectangular cuboid body with a length greater than its width and height. One or more slits may run along its length. The spring blocks 576 sit inside the housing 574 on either side of the band slot 578 such that the spring blocks 576 protrude into the band slot 578.

The spring blocks 576 may be elastically compressed to allow passage of the flexible band 12 through the slot 578. The spring blocks 576 may define a chamfer 582 on the leading edge to allow engagement of an instrument to compress the spring blocks 576 out of the slot 578, thus allowing passage of the flexible band 12. The flexible band 12 is then tensioned to provide fixation to the anatomy. When the instrument is removed from the implant 572, the spring blocks 576 return to their resting position and contact the band 12. The contact between the spring blocks 576 and the flexible band 12 secures the tension in the band 12.

Figure 57A:
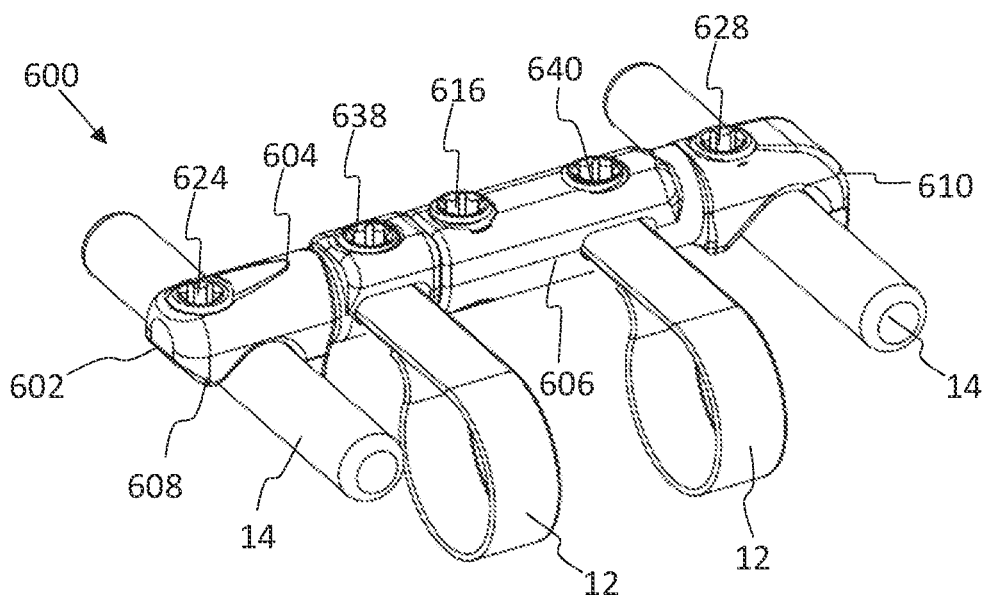
FIG. 57A-57C show an embodiment of a cross connector implant configured to secure two flexible bands.
Figure 57B:
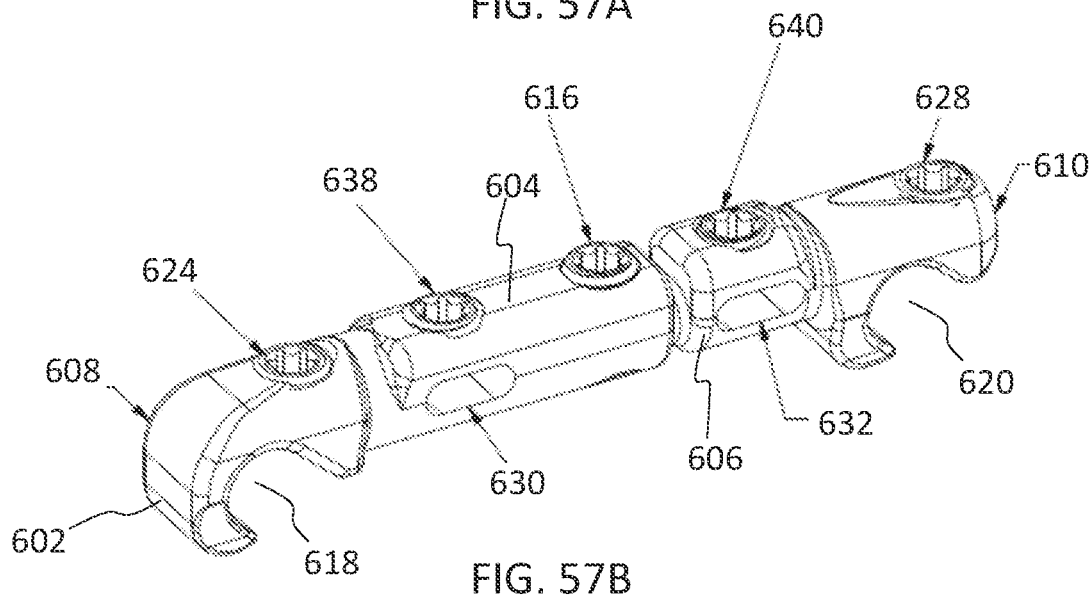
Figure 57C:
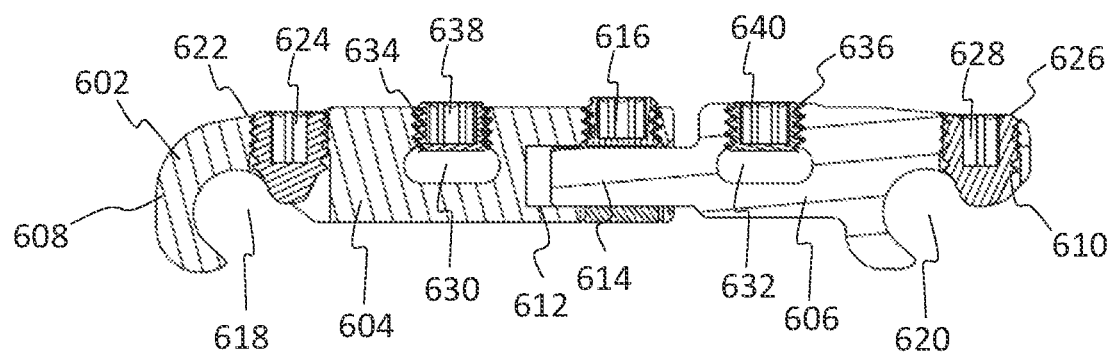
Figure 59B:
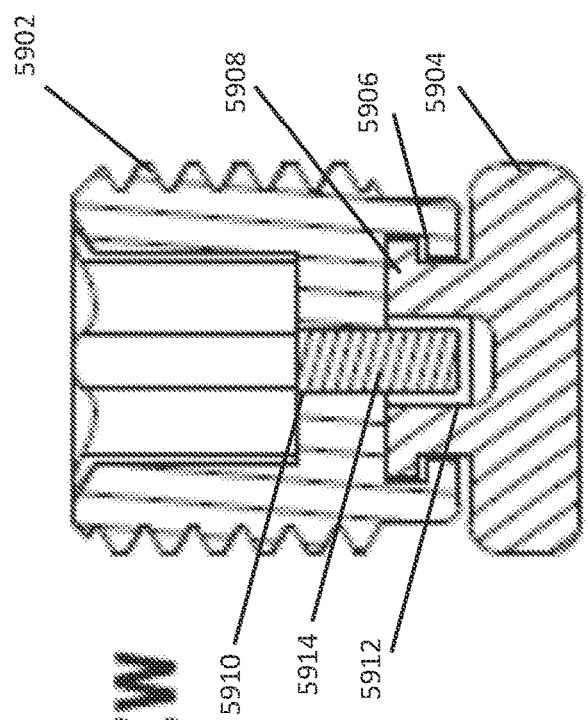
FIGS. 59A and 59B show an exemplary embodiment of a locking mechanism consistent with the principles of the present disclosure.
Figure 59A:
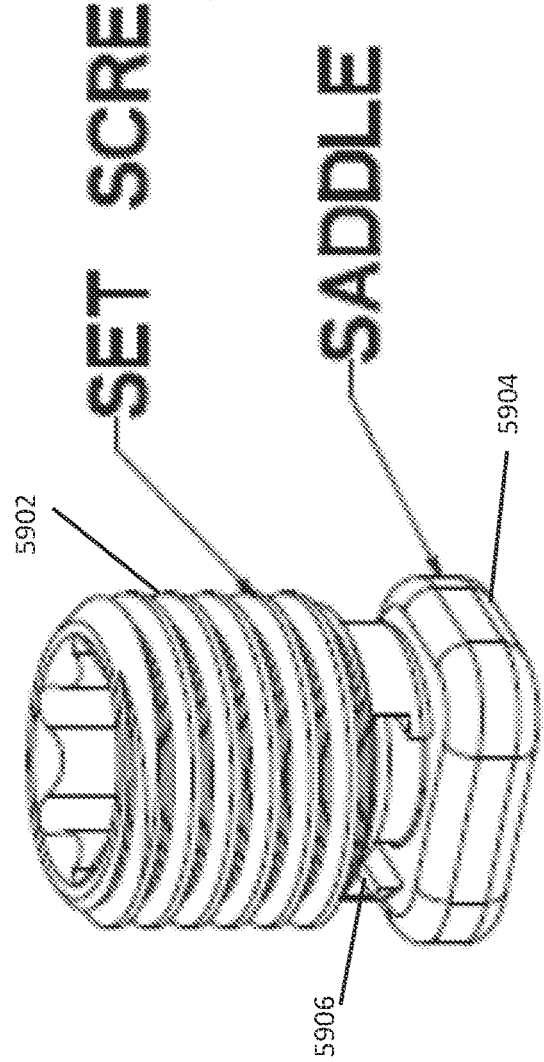

Turning now to FIGS. 57A-57C, a cross connector assembly or system 600 is shown according to one embodiment. The implant 602 is a cross connector which connects to two rods 14 and secures two separate flexible bands 12 around bone. With reference to FIG. 57A, the implant 602 includes first and second arms 604, 606 configured to translate toward and away from one another. The first arm 604 includes a first open clamp 608 configured to receive the first rod 14, and the second arm 606 includes a second open clamp 610 configured to receive the second rod 14. First and second rods 14 may extend generally parallel to one another.

As shown in FIG. 57C, the first arm 604 may define a central longitudinal bore 612 sized and dimensioned to accept an extension 614 of the second arm 614, which allows the arms 604, 606 to translate with respect to one another. In this manner, the overall length of the implant 602 may be adjusted based on the distance between the first and second rods 14. A first fastener or set screw 616 may be located at the medial end the first arm 604. The set screw 616 may be threaded downward to lock translation and the distance of the two arms 604, 606. It will be appreciated that the configuration of the bore 612 and extension 614 may be reversed or otherwise configured to allow for translation between the two arms 604, 606.

Each arm 604, 606 has an open clamp 608, 610 to accept the respective spinal rod 14 and a set screw 624, 628 to secure the implant 602 to the spinal rods 14. The first clamp 608 defines a first opening, recess, or rod slot 618 sized and dimensioned to accept the spinal rod 14. The rod slot 618 may define a generally c-shaped recess sized and dimensioned to receive the first rod 14 when bottom loaded into the implant 602. The hook of the clamp 608 may be facing inward toward the center of the implant 602. The second clamp 610 defines a second opening, recess, or rod slot 620 sized and dimensioned to accept the spinal rod 14. The rod slot 620 may define a generally c-shaped recess sized and dimensioned to receive the second rod 14 when bottom loaded into the implant 602. The hook of the clamp 610 may be facing outward away from the center of the implant 602. It will be appreciated that the slots 618, 620 may be faced in any suitable direction for attachment to the rods 14.

The first arm 604 defines a first threaded hole 622 in fluid communication with the rod slot 618. The second locking member or set screw 624 is positionable within the first threaded hole 622, and when in a downward position, a bottom surface of the set screw 624 is configured to contact and secure the spinal rod 14 within the clamp 608. Similarly, the second arm 606 defines a second threaded hole 626 in fluid communication with the rod slot 620. The third locking member or set screw 628 is positionable within the second threaded hole 626, and when in a downward position, a bottom surface of the set screw 626 is configured to contact and secure the spinal rod 14 within the clamp 610.

Each of the arms 604, 606 define a thru slot or band slot 630, 632 configured to accept the flexible bands 12. The band slots 630, 632 may be located generally parallel to one another. The band slots 630, 632 may be located such that the slots 630, 632 are positioned above the lamina. A threaded hole 634, 636 sits above and in fluid communication with each band slot 630, 632 to accept a threaded set screw 638, 640. Each of the threaded set screws 638, 640 may be threaded downward to secure the flexible bands 12. Each of the set screws 616, 624, 626, 638, 640 may define an instrument recess configured to be engaged by an instrument, such as a driver, for rotating the set screws 616, 624, 626, 638, 640 into the downward locked positions.

Turning now to FIGS. 58-81, alternative embodiments consistent with the principles of the present disclosure are illustrated. These embodiments allow locking a flexible band in tension without the presence of a spinal rod.

Referring to FIGS. 58A and 58B, a band clamp 5800 is illustrated. Band clamp 5800 is capable of securing a flexible band in tension. Band clamp 5800 has a main body 5802 with a first opening 5804 to accept a flexible band, which may be referred to as a band slot 5804 and a second opening 5806 located beneath first opening 5804, which may be referred to as an anchor slot 5806. Main body 5802 has a threaded hole 5808 in communication with band slot 5804. A threaded locking member 5810 may be positioned within the threaded hole to contact the flexible band and secure it to main body 5802.

Threaded locking member 5810 may include a threaded set screw 5902 coupled to a saddle 5904. Set screw 5902 may have a slot 5906 to accept an upper portion 5908 of saddle 5904. A hole 5910 through the long axis of set screw 5902 may be aligned with a corresponding hole 5912 along the long axis of saddle 5904 when upper portion 5908 of saddle 5904 is positioned within slot 5906 in set screw 5902. A pin 5914 may be pressed into holes 5910 and 5912 in an aligned positioned of set screw 5902 and saddle 5904 to prevent saddle 5904 from dislodging from the set screw.

In one exemplary embodiment shown in FIG. 60A, set screw 5902 and saddle 5904 may be permanently engaged with main body 5802 after assembly. Main body 5802 has geometry such that set screw 5902 is threaded into main body 5802 from the top and saddle 5904 is inserted into slot 5906 in set screw 5902 from band slot 5804. Saddle 5904 is sized such that it cannot pass through the minor diameter of the threads in main body 5802, therefore preventing disassembly when set screw 5902 is threaded upward. Main body 5802 has geometry such that saddle 5904 cannot rotate within main body 5802, but can translate up and down with actuation of set screw 5902. Main body 5802 also has relief space above band slot 5906 such that saddle 5904 is able to be positioned above band slot 5804 when set screw 5902 is threaded upward, allowing free passage of the flexible band through band slot 5906.

In an exemplary embodiment shown in FIG. 60B, set screw 5902 and saddle 5904 may be threaded into and out of main body 5802. Main body 5802 has a groove 6002 through the threads to accept a mating bump 6004 on saddle 5904, which prevents saddle 5904 from rotating when set screw 5902 is threaded up and down within main body 5802.

Figure 61:
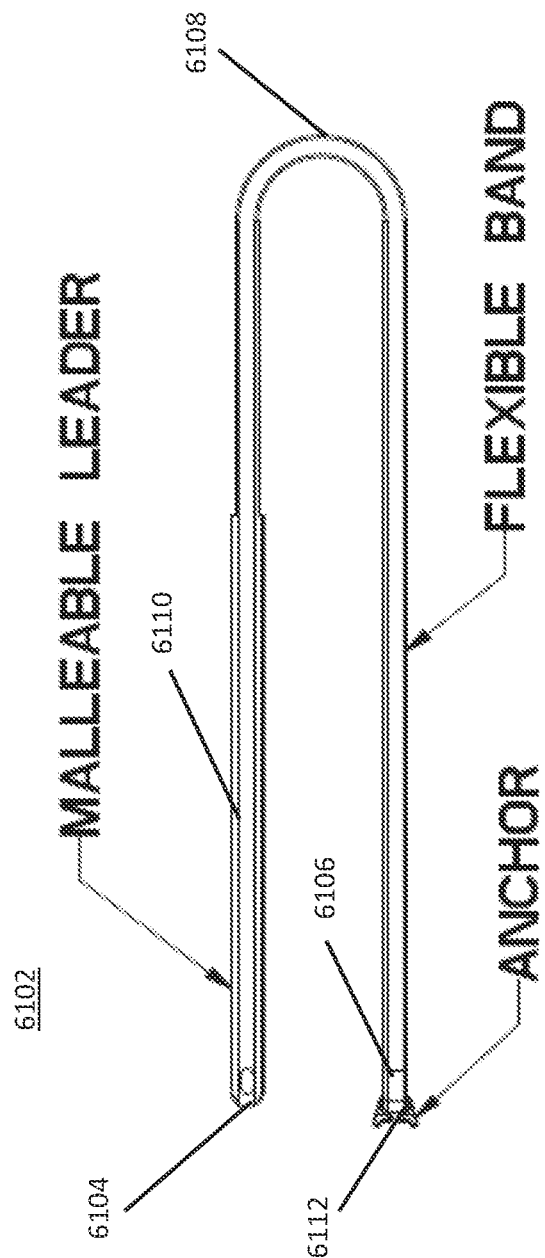
FIG. 61 shows an exemplary embodiment of a flexible band consistent with the principles of the present disclosure.
Figure 62:
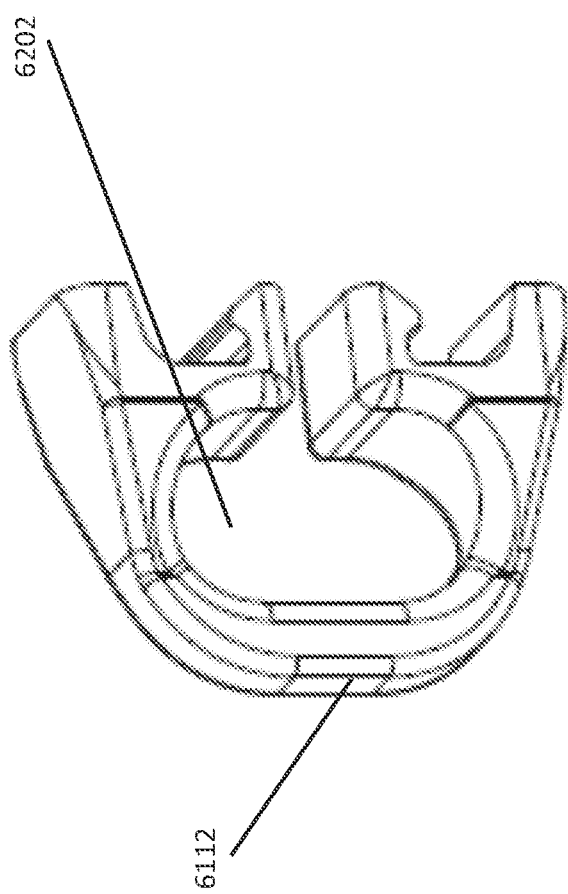
FIG. 62 shows an exemplary embodiment of an anchor consistent with the principles of the present disclosure.

As shown in FIG. 61, an exemplary flexible band 6102 consistent with the principles of the present disclosure is illustrated. Flexible band 6102 has a first end 6104, a second end 6106, and a middle portion 6108 in between. Middle portion 6108 is intended to contact bone. First end 6102 is attached to a leader 6110. A leader 6110 may be fed around anatomy to wrap flexible band 6102 around the anatomy to be fixated. Leader 6110 may be malleable or rigid. Second end 6106 of flexible band 6102 is attached to an anchor 6112. Anchor 6112 has geometry such that it may be engaged with a mating recess in the main body of the band clamp. As shown in FIG. 62, anchor 6112 may have a cut 6202 which allows anchor 6112 to contract when first entering anchor slot 5806 and then expand into a mating recess in anchor slot 5806 in main body 5802. Once positioned fully within the mating recess, anchor 6112 may spring back open to prevent disassembly. Anchor 6112 may also have a feature to engage with a mating instrument to allow disassembly.

Figure 63:
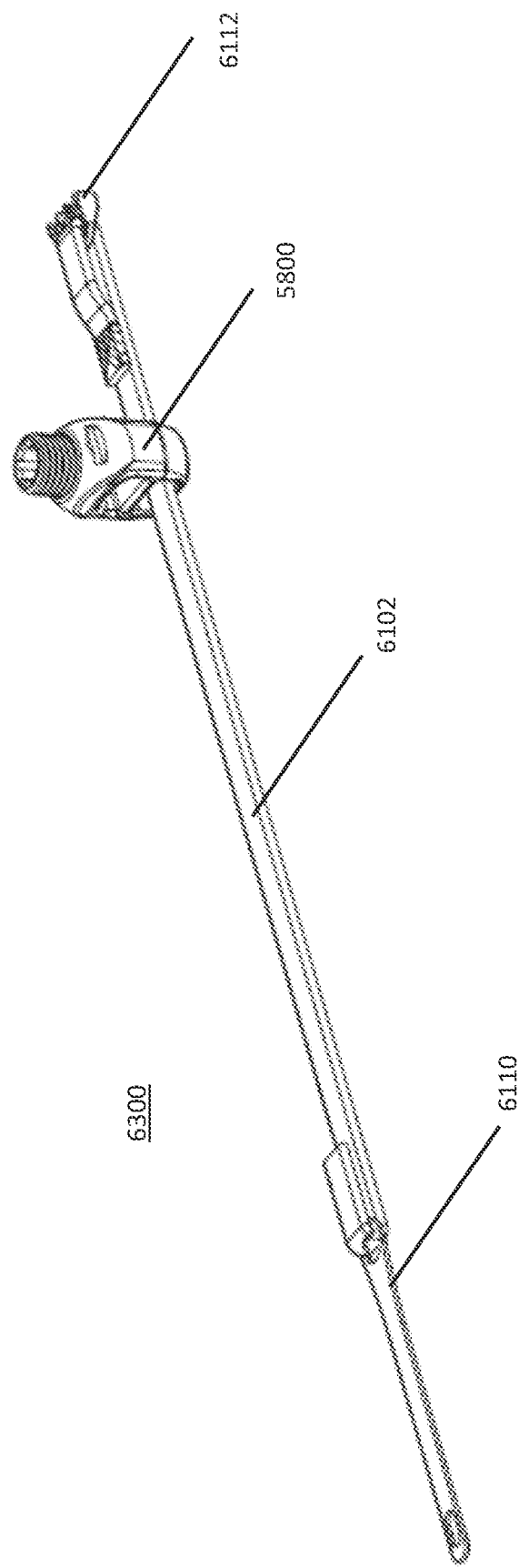
FIG. 63 shows an exemplary embodiment of a band clamp system or assembly consistent with the principles of the present disclosure.
Figure 64:
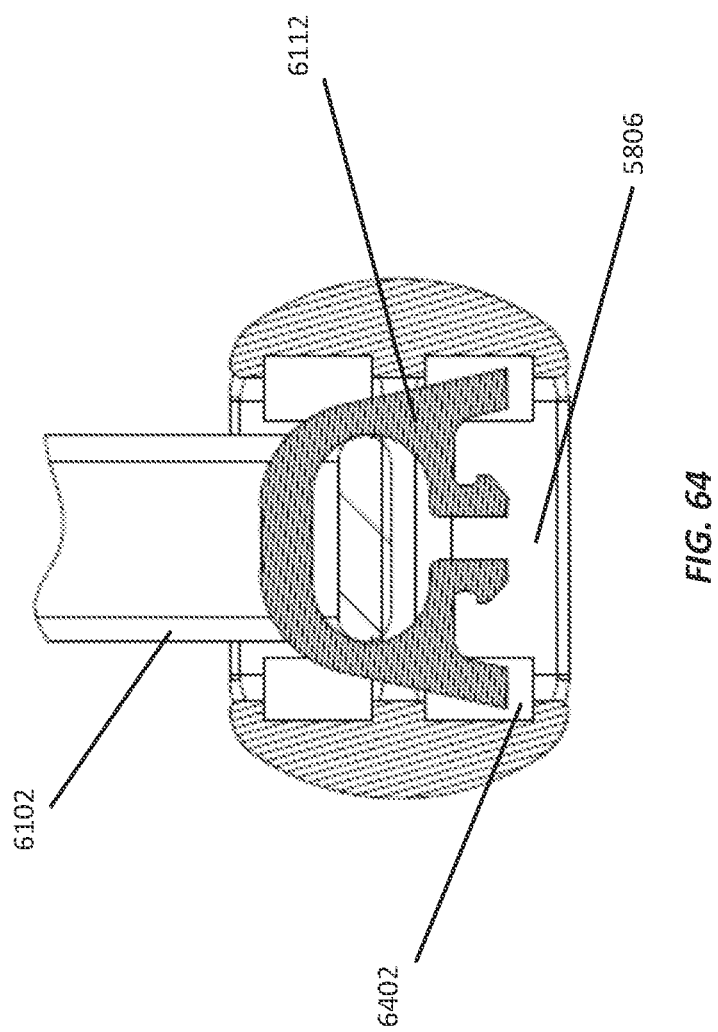
FIG. 64 shows a cross-section of an exemplary embodiment of an anchor disposed in an anchor slot consistent with the principles of the present disclosure.
Figure 65:
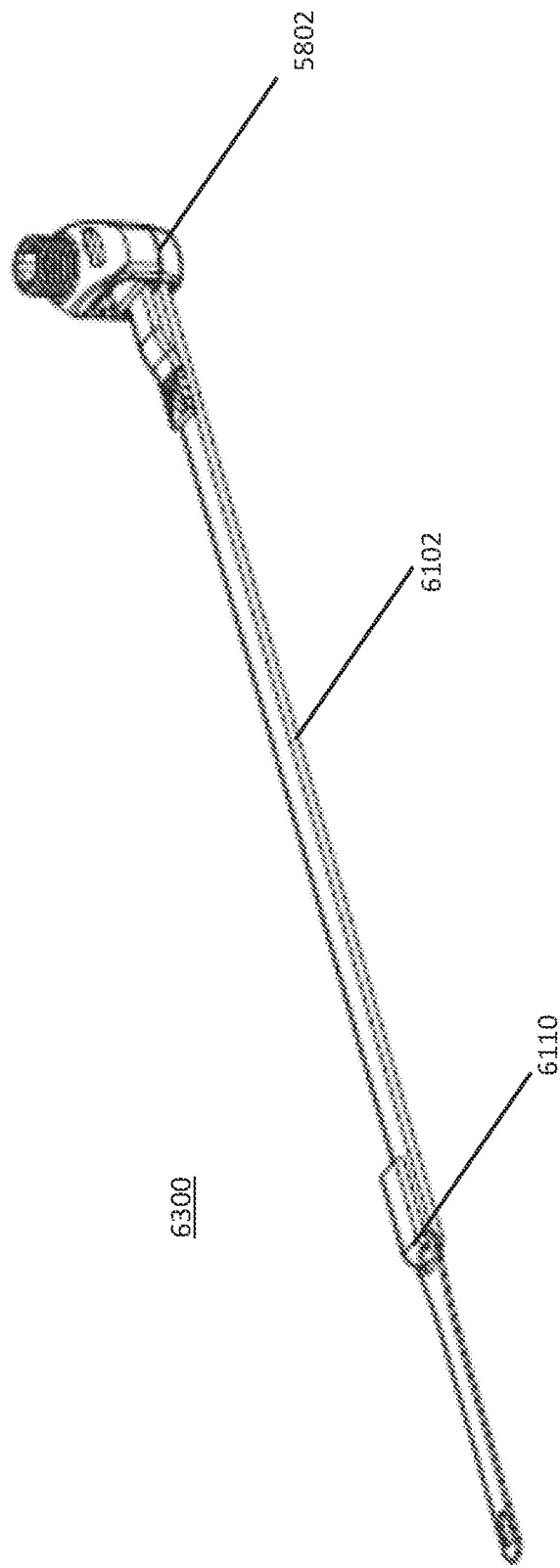
FIG. 65 shows an exemplary embodiment of a band clamp system or assembly consistent with the principles of the present disclosure.

FIG. 63 illustrates a band clamp system or assembly 6300, including band clamp 5800, flexible band 6102, leader 6110, and anchor 6112. Main body 5802 has anchor slot 5806 located beneath band slot 5804. The geometry of anchor slot 5806 is such that it can engage anchor 6112 of flexible band 6102. As shown in FIG. 63, flexible band 6102 is inserted, leader 6110 end first, through anchor slot 5806 in main body 5802 and pulled through until anchor 6112 engages a mating recess 6402. As shown in FIG. 64, engagement between anchor 6112 and the mating recess causes flexible band 6102 to become securely attached to main body 5802. FIG. 65 illustrates flexible band engaged with main body 5802 of band clamp 5800.

Figure 66:
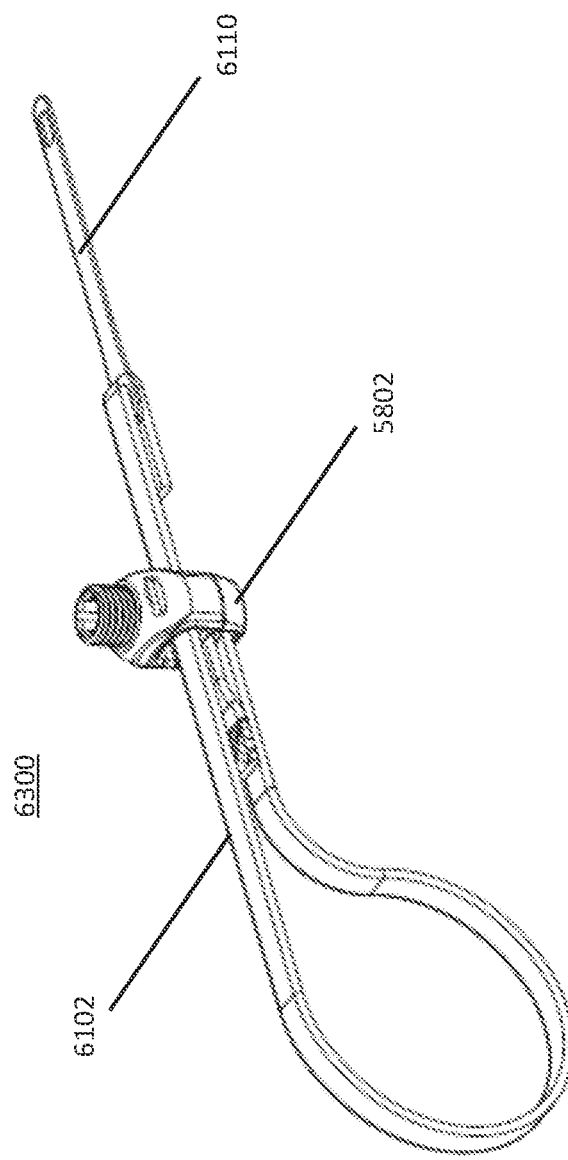
FIG. 66 shows an exemplary embodiment of a band clamp system or assembly consistent with the principles of the present disclosure.
Figure 67:
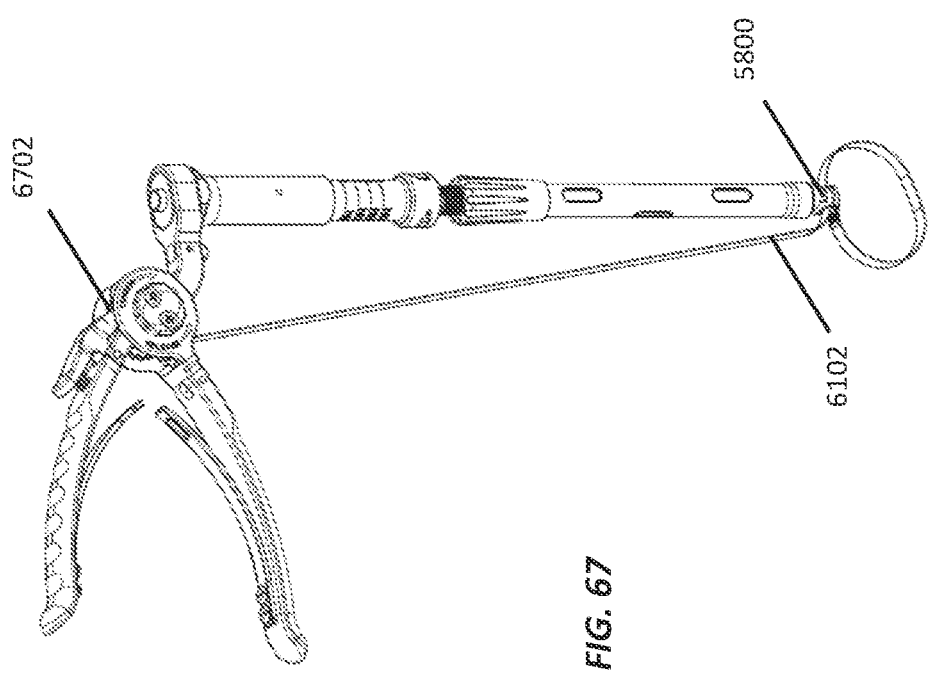
FIG. 67 shows an exemplary embodiment of a band clamp system or assembly and tensioning instrument consistent with the principles of the present disclosure.
Figure 68:
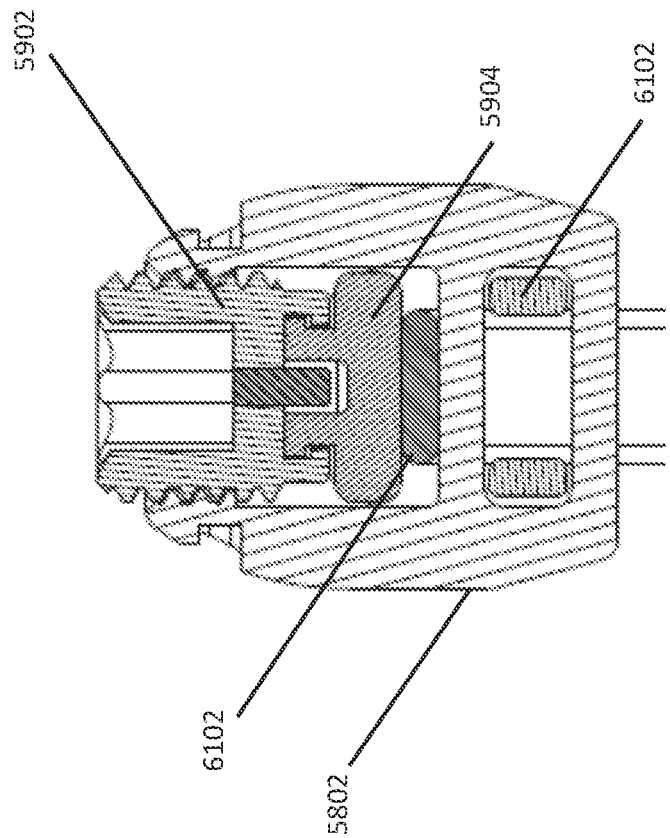
FIG. 68 shows a cross-section of an exemplary embodiment of a band clamp system or assembly consistent with the principles of the present disclosure.
Figure 69:
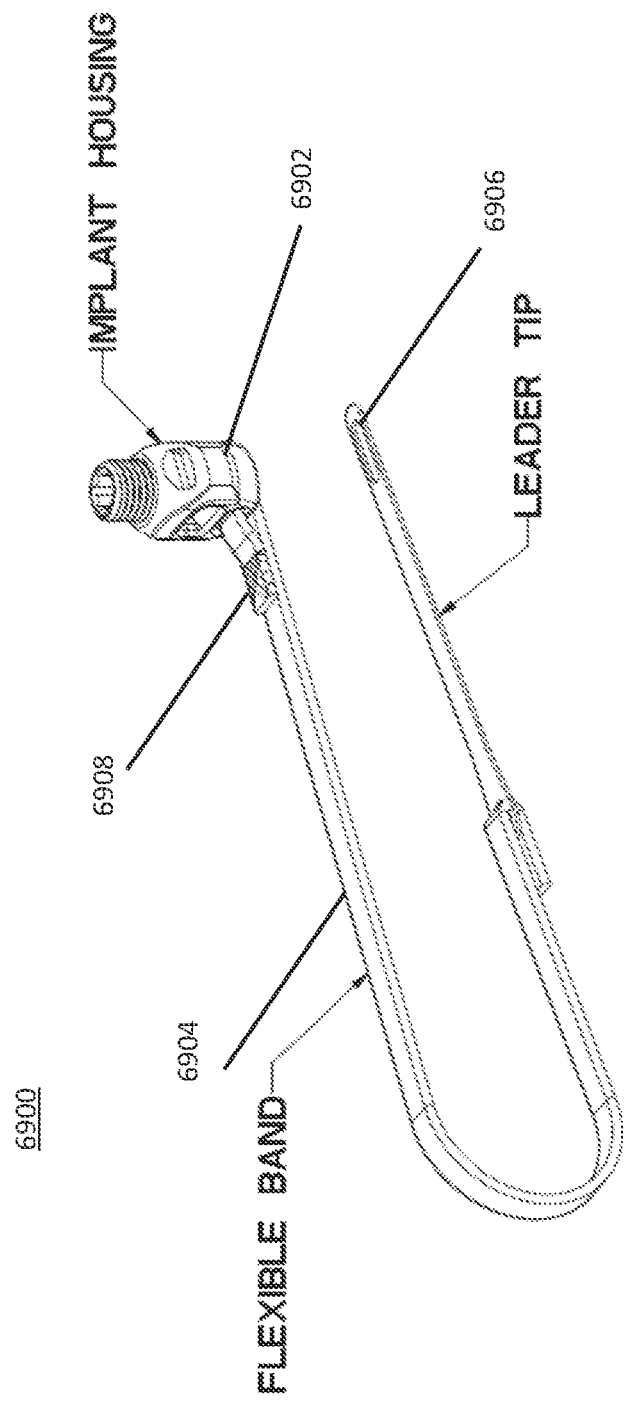
FIG. 69 shows an exemplary embodiment of a band clamp system or apparatus consistent with the principles of the present disclosure.

As shown in FIG. 66, the free end of flexible band 6102 is then wrapped around the patient anatomy to be fixated and passed back through band slot 5806 to create a loop. As shown in FIG. 67, the loop is tensioned by pulling on the free end of flexible band 6102 with a tensioning instrument or ratcheting tensioner 6702. Once the desired amount of tension is placed on flexible band 6102 to achieve fixation, set screw 5902 is threaded downward forcing the saddle to contact and secure flexible band 6102 in band clamp 5800, as shown in FIG. 68.

FIGS. 69-72 illustrate a band clamp system 6900, including band clamp 6902, flexible band 6904, and leader tip 6906. Band clamp system 6900 is a band clamp 6902 that is connected to flexible band 6904. Band clamp 6902 has a set screw component 6910 and a saddle component 6912 for securing flexible band 6904 similar to what has been previously described with respect to FIGS. 58A-68. Flexible band 6904 has leader tip 6906 on a first end for passage around bony anatomy. Leader tip 6906 may be malleable in order to shape it to more easily pass around anatomy.

Figure 70B:
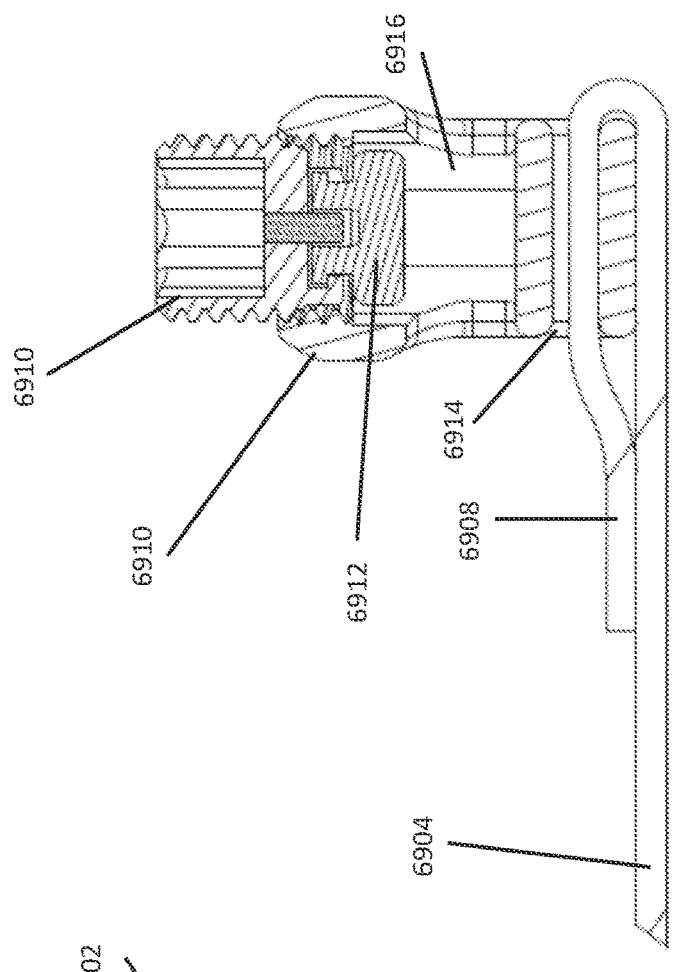
FIGS. 70A and 70B show an exemplary embodiment of a band clamp consistent with the principles of the present disclosure.
Figure 70A:
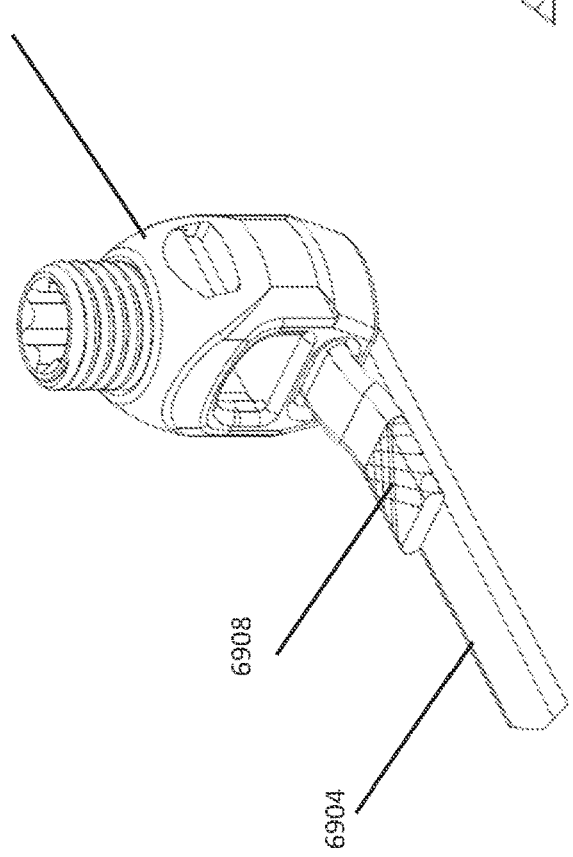

As shown in FIGS. 70A-70B, band clamp 6902 has two slots. One slot 6914 is where flexible band 6904 is looped and sewn into place at a sewn portion 6908 to create one assembly at a second end. The second slot 6916 is where the opposite end of flexible band 6904 is fed back through band clamp 6902 to create a loop. Band clamp 6902 has a threaded hole and relief space intersecting the upper band slot (FIG. 70B). The set screw and saddle components are coupled together and travel up and down such that the set screw is always engaged with the threaded hole and the saddle is positioned within the relief space. The relief space is shaped such that the saddle cannot rotate during translation.

Figure 72:
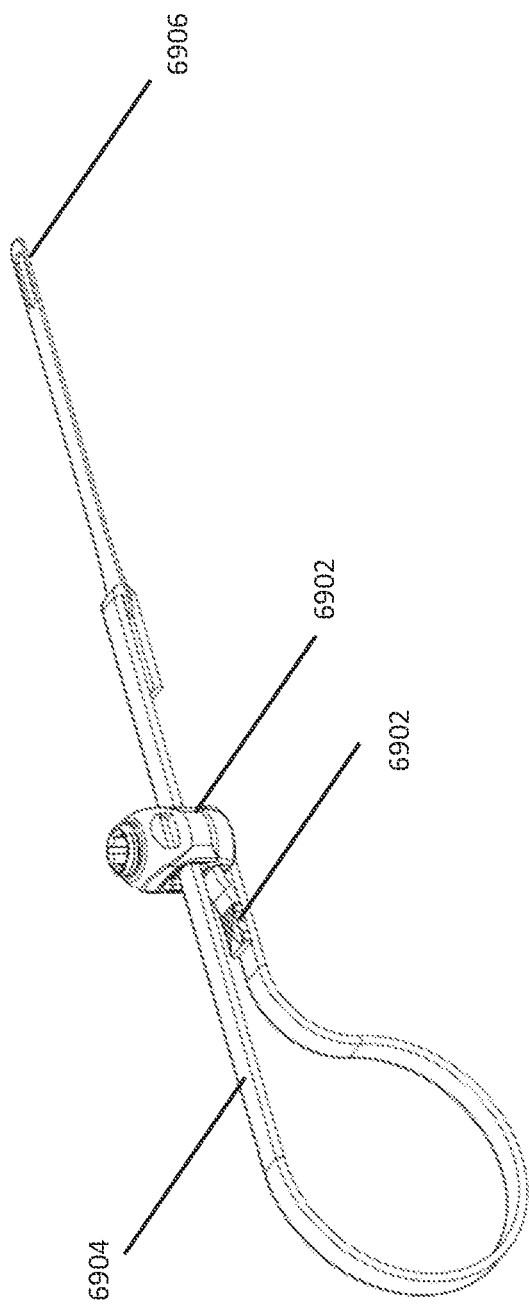
FIGS. 72 and 73 show an exemplary embodiment of a band clamp system consistent with the principles of the present disclosure.

The set screw may be positioned in an up position where the saddle is located in the relief space above the band slot and the band slot is free to accept flexible band as shown in FIG. 71A. When the set screw is threaded downward the saddle may secure flexible band by contacting it in the band slot as shown in FIG. 71B. Band clamp 6902 may also have a feature for engagement with an insertion and tensioning instrument. FIG. 72 illustrates flexible band 6904 looped back through band clamp 6902.

Figure 73:
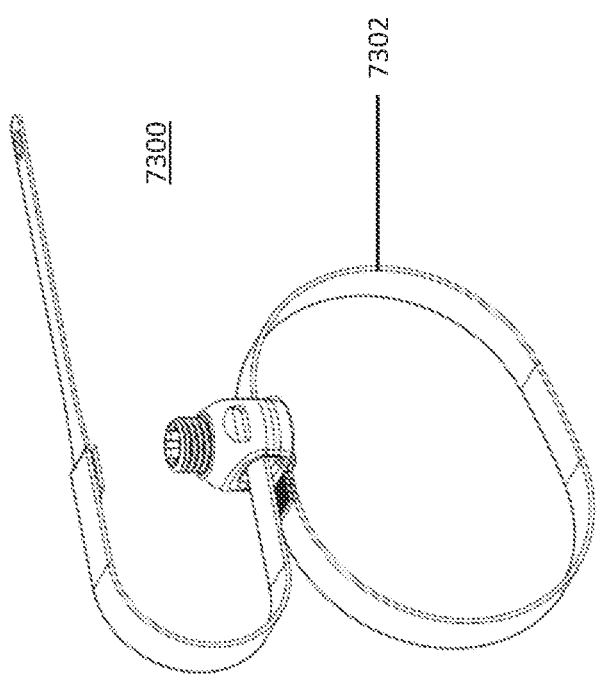

FIG. 73 illustrates an exemplary embodiment of a band clamp assembly 7300 consistent with the principles of the present disclosure. Here, band clamp 7302 is similar to previously described band clamps, however, band clamp 7302 has one slot for sewing a portion of a flexible rod which is then looped back into the same slot.

Figure 74D:
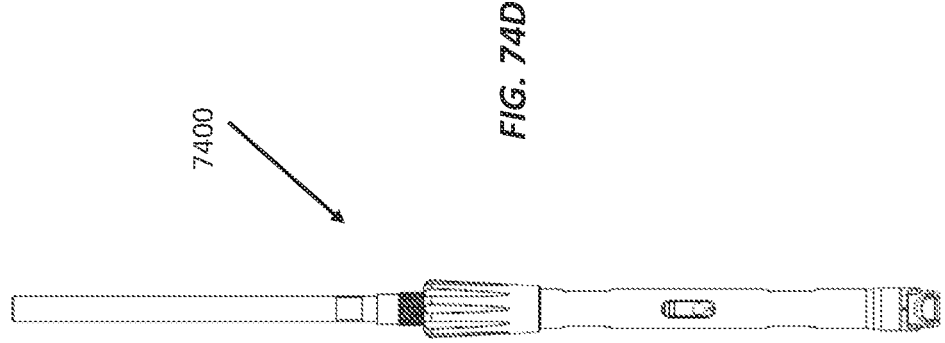
FIG. 74D shows an exemplary embodiment of an instrument assembly consistent with the principles of the present disclosure.
Figure 74A:
FIG. 74A shows an exemplary embodiment of an inserter fork consistent with the principles of the present disclosure.
Figure 74B:
FIG. 74B shows an exemplary embodiment of an outer sleeve consistent with the principles of the present disclosure.
Figure 74C:
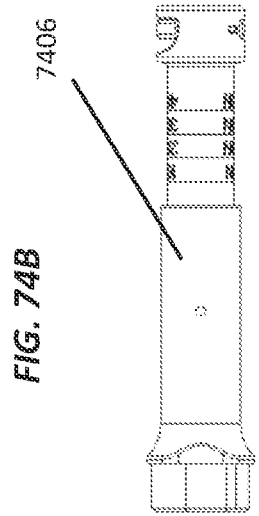
FIG. 74C shows an exemplary embodiment of a tension indicator consistent with the principles of the present disclosure.
Figure 75:
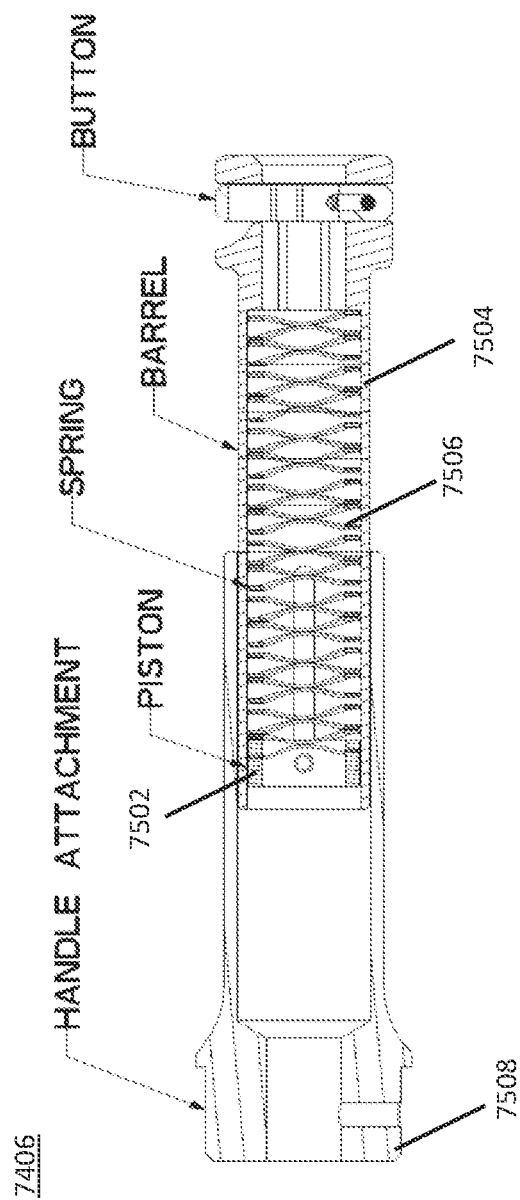
FIG. 75 shows an exemplary embodiment of a tension indicator consistent with the principles of the present disclosure.

Turning now to FIGS. 74A-80, an instrument assembly 7400 of a tensioning instrument may include an inserter fork 7402, an outer sleeve 7404, and tension indicator 7406 consistent with the principles of the present disclosure is illustrated. Assembly 7400 may be used with a tensioning instrument (such as, for example, tensioning instrument 6702) to apply tension to one of band clamp assemblies 5800, 6300, 6900, and 7300 (see, FIG. 67). FIG. 74A depicts inserter fork 7402, FIG. 74B depicts outer sleeve 7404, and FIG. 74C depicts tension indicator 7406.

Inserter fork 7402 and outer sleeve 7404 couple together via a thread. A distal end of inserter fork 7402 has geometry for engagement with the band clamps previously described, for example band clamps with assemblies 5800, 6300, 6900, and 7300.

A distal end of inserter fork 7402 is splayed at rest in order to accept a band clamp. Outer sleeve 7404 may be threaded distally, which squeezes the inserter fork into a locked position in order to securely hold the band clamp as shown in FIG. 74D.

Figure 76:
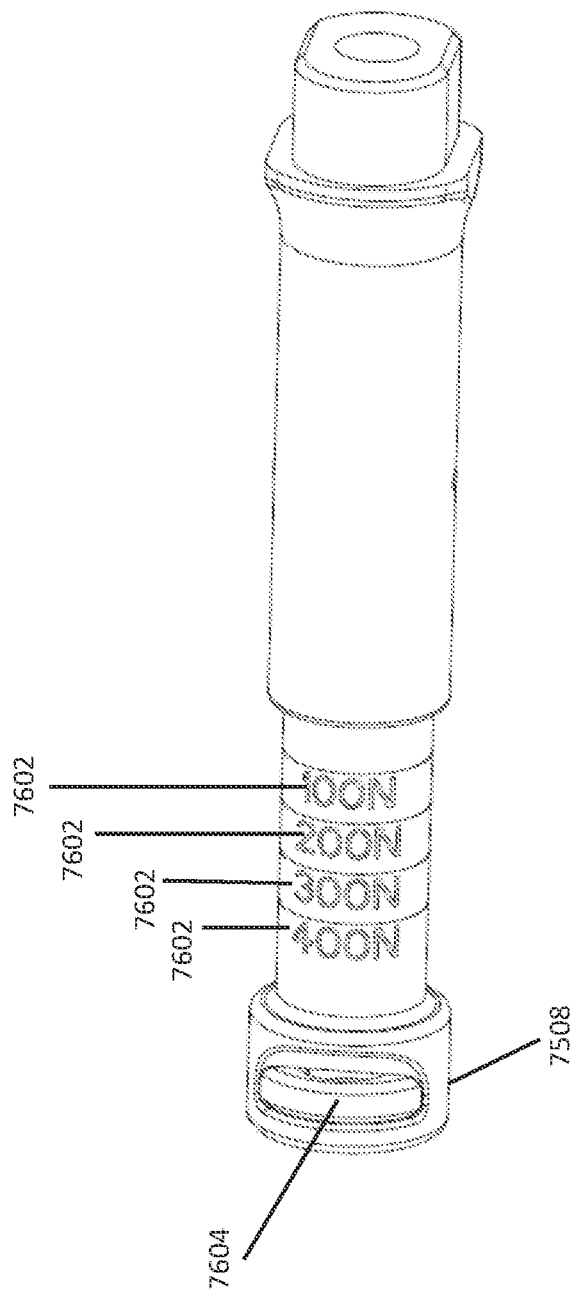
FIG. 76 shows an exemplary embodiment of a tension indicator consistent with the principles of the present disclosure.

Tension indicator 7406 has a piston 7502 that rides inside a barrel 7504. Piston 7502 contacts a spring 7506 such that the force required to move piston 7502 is directly correlated with the distance the piston has moved. Tension indicator 7406 has a handle attachment 7508 coupled to piston 7502 via a pin through a slot in the barrel. Handle attachment 7508 may slide over barrel 7504, which translates piston 7502 and compresses spring 7506. Barrel 7504 may have etchings 7602 on it such that the position of handle attachment 7508 indicates the amount of force exerted on spring 7506 as shown in FIG. 76. Handle attachment 7508 has geometry 7604 to engage with a ratcheting tensioner such as tensioning instrument 6702.

Figure 77:
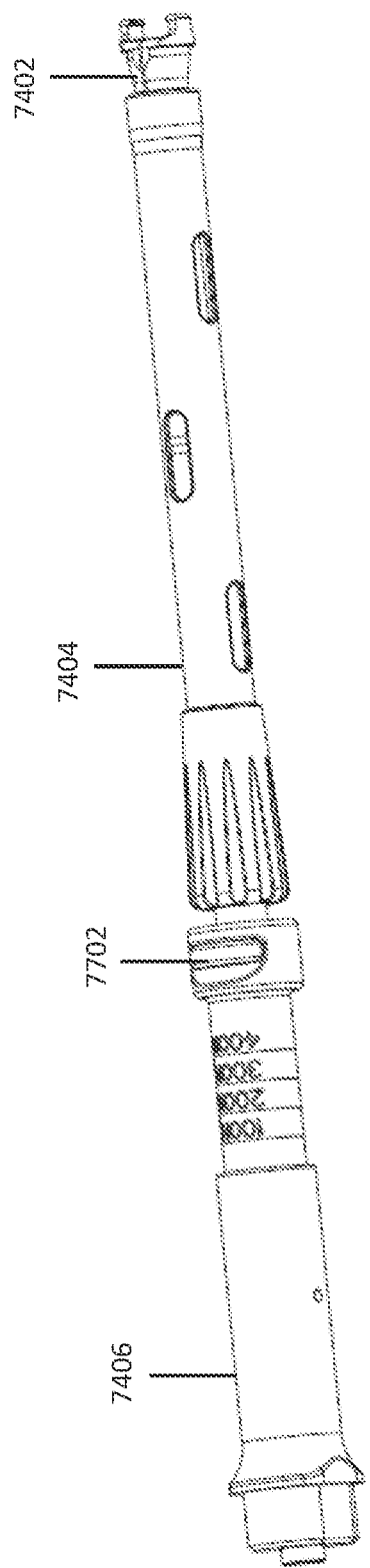
FIG. 77 shows an exemplary embodiment of an instrument assembly consistent with the principles of the present disclosure.
Figure 78:
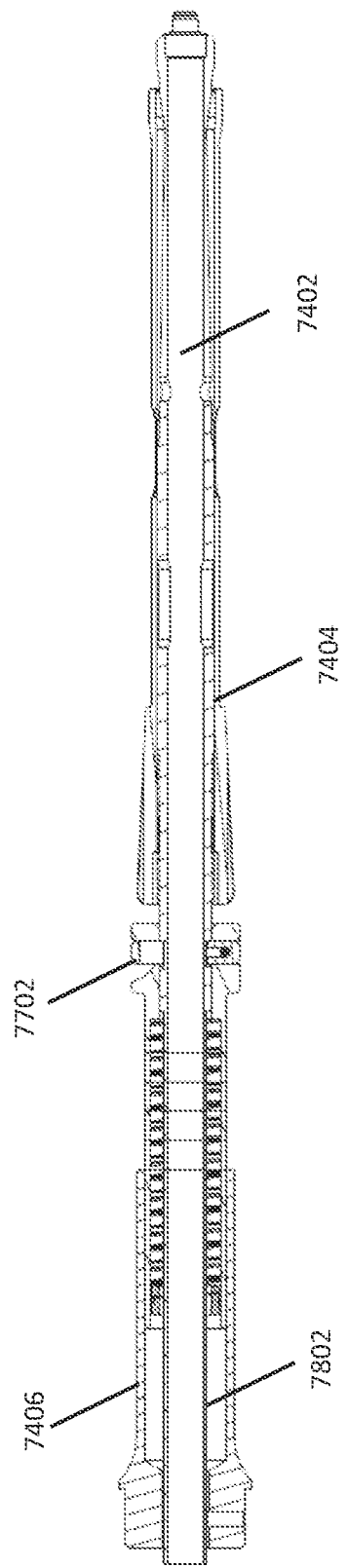
FIG. 78 shows a cross-section of an exemplary embodiment of an instrument assembly consistent with the principles of the present disclosure.
Figure 79:
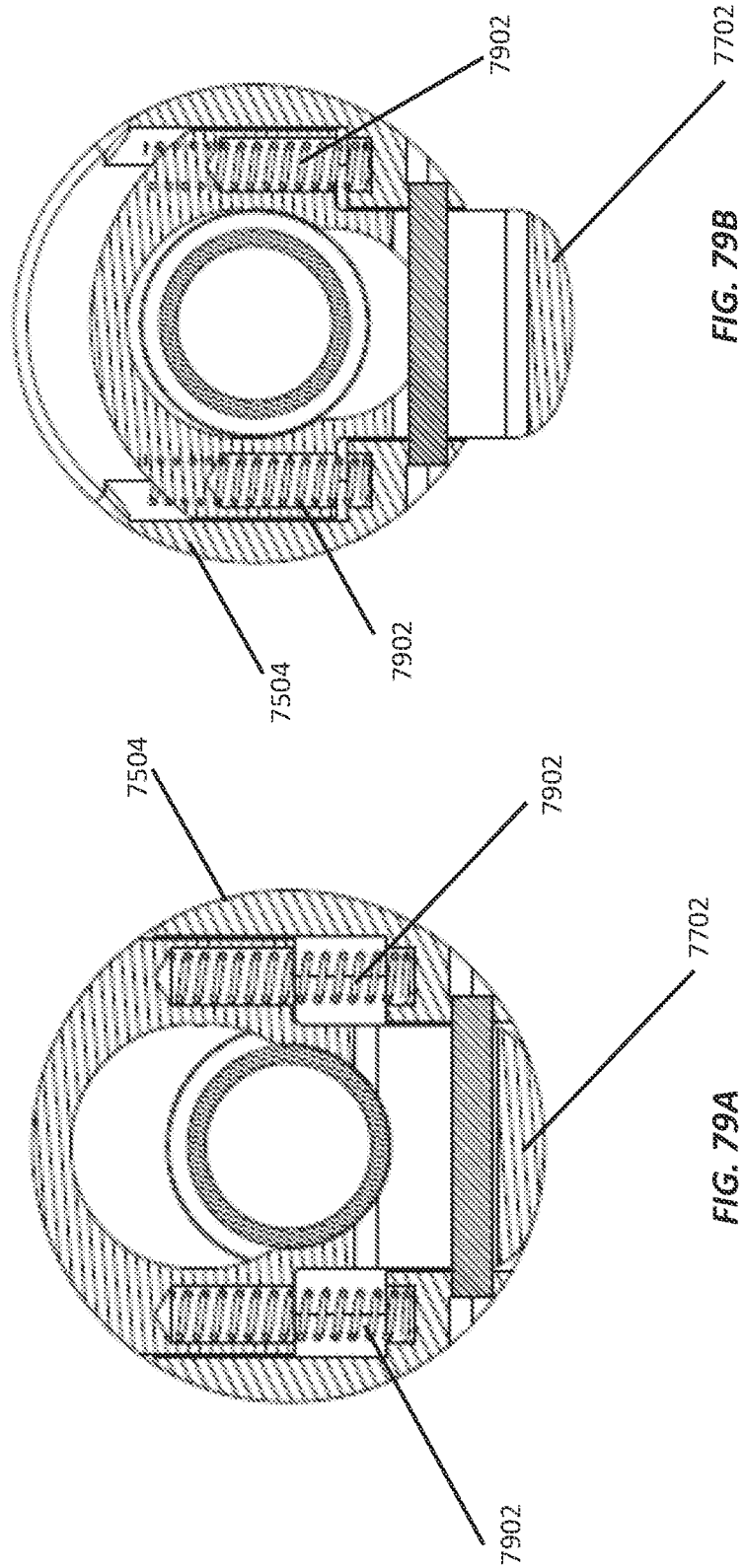
FIGS. 79A, 79B, and 80 shows a cross-section of an exemplary embodiment of an instrument assembly consistent with the principles of the present disclosure.
Figure 80:
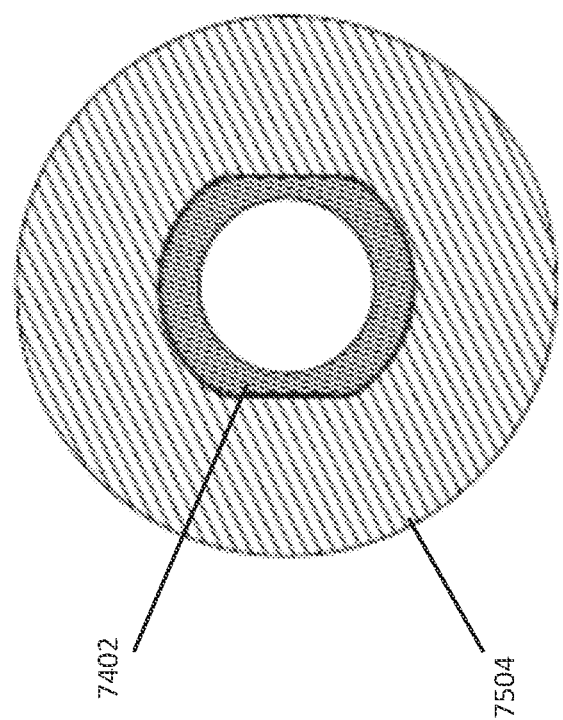
Figure 81:
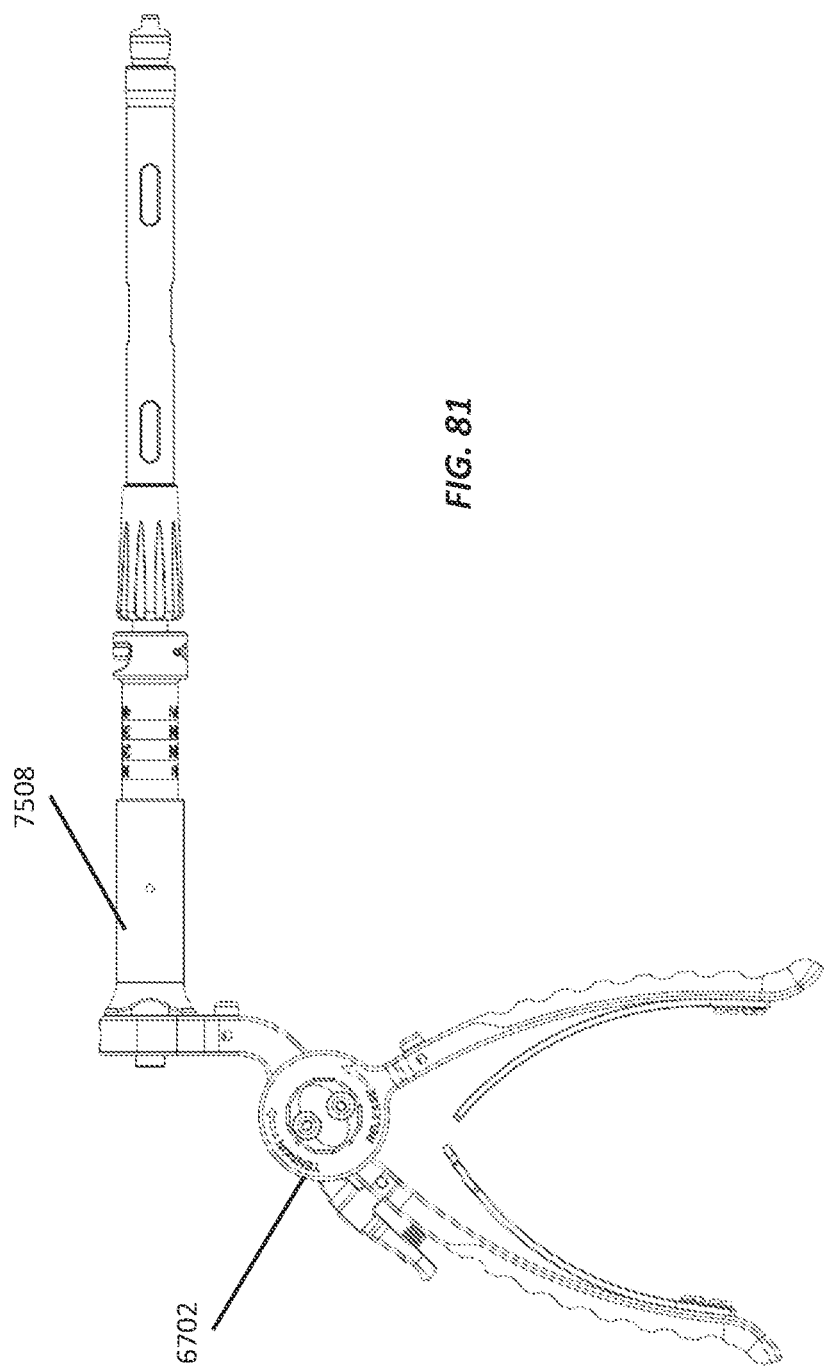
FIG. 81 shows an exemplary embodiment of a tensioning instrument including the instrument assembly consistent with the principles of the present disclosure.

As shown in FIGS. 77-78, tension indicator 7406 has a thru hole 7802 to accept inserter fork 7402 and a button assembly 7702 to engage with inserter fork 7402. Button 7702 is positioned within a slot 7704 in the barrel 7504 and coupled via a pin. The pin is positioned within a slot in the button such that the button can slide up and down within the slot in barrel 7504. Two compression springs 7902 are captured between the button 7702 and barrel 7504 causing button 7702 to remain in an up position at rest. Inserter fork 7402 has a slot to mate with the button assembly 7702 on the tension indicator 7406. Button 7702 has geometry such that inserter fork 7402 can slide through button 7702 freely when button 7702 is pressed into the down position as shown in FIG. 79A. Inserter fork 7402 and barrel 7504 have mating geometry which prevents rotation between the two parts during engagement as shown in FIG. 80.

Handle attachment 7508 of the tension indicator 7406 has a feature to engage with the ratcheting tensioner 6702. Ratcheting tensioner 6702 may tension flexible band causing a force to be applied to spring 7506 in tension indicator 7406. Therefore, the instrument assembly is able to indicate to the user how much tension is in the band based on how far the spring is compressed. This is indicated by the etchings on the barrel. It is advantageous for the user to know how much tension is in the band in order to achieve adequate fixation.

An exemplary method of fixating the spine using band clamp assembly 6300, instrument assembly 7400, and ratcheting tensioner 6702 will described in the following steps:

1. Use leader 6110 on flexible band 6102 to wrap flexible band 6102 around the bony structures to be fixated.
2. Pass the end of flexible band 6102 back though band slot 5804 on band clamp 5800.
3. Thread outer sleeve 7404 onto inserter fork 7402.
4. Engage tension indicator 7406 onto inserter fork 7402.
5. Engage ratcheting tensioner 6702 onto tension indicator 7406.
6. Engage inserter fork 7402 onto main body 5802 and thread outer sleeve 7404 down to securely capture main body 5802 onto inserter fork 7402.
7. Position main body 5802 in the desired location on the spine.
8. Feed the end of flexible band 6102 through the spool on the ratcheting tensioner 6702.
9. Actuate the handles of ratcheting tensioner 6702 to wrap flexible band 6102 around the spool, thereby applying tension to flexible band 6102.
10. Stop tensioning flexible band 6102 when tension indicator 7406 indicates a desired amount of tension.
11. Insert a final tightening driver shaft through inserter fork 7402 and into set screw 5902 on band clamp 5800.
12. Tighten set screw 5902 to lock flexible band 6102 to main body 5802.
13. Cut the excess length of flexible band 6102 near main body 5802.
14. Disengage the instrument assembly from the implant.

The various implants allow the surgeon to fixate the spine by securing the sublaminar band to the spinal rod construct or by securing two vertebral levels to each other. Sublaminar bands may be useful when traditional pedicle screw fixation is compromised or not possible, for example, in the case of patients with dysmorphic vertebrae, osteoporosis and/or fractured pedicles. The implants may help to fixate the spine using the sublaminar band(s) in these types of clinical scenarios.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A band clamp implant assembly comprising:
a band clamp including a main body, a threaded locking member, a band slot, and an anchor slot, wherein the main body includes a mating recess; and
a flexible band having a first end, a second end, and a middle portion therebetween, wherein a leader is attached to the first end, an anchor is attached to the second end, and the middle portion is configured to contact bone, wherein the anchor is configured to engage the mating recess, wherein the leader is configured to loop around patient anatomy and pass through the band slot, and wherein the threaded locking member is configured to lock the flexible band in the band clamp
wherein the anchor has a cut to allow the anchor to contact to enter the anchor slot and then expand to be received into the mating recess.

2. The assembly of claim 1, wherein the leader is configured to pass through the anchor slot until the anchor engages with the mating recess, the leader further configured to wrap around patient anatomy and then be inserted into the band slot to create a loop around the patient anatomy with the middle portion of the flexible band.

3. The assembly of claim 2, wherein the locking member locks the flexible band to the main body of the band clamp after the leader is passed through the band slot.

4. The assembly of claim 3, wherein tension is provided to the flexible band prior to the locking member locking the flexible band to the band clamp.

5. The assembly of claim 1, wherein the locking member is threaded into the main body of the band clamp.

6. The assembly of claim 5, wherein the locking member includes a threaded set screw and a saddle.

7. The assembly of claim 6, wherein the threaded set screw is configured to receive the saddle via a slot in the threaded set screw.

8. The assembly of claim 7, wherein the saddle engages the flexible band to lock the flexible band in the band clamp.

9. The assembly of claim 1, wherein the anchor slot is disposed under the band slot.

10. A system for fixating adjacent vertebral bodies, said system comprising:
   a band clamp including a main body, a threaded locking member, a band slot, and an anchor slot, wherein the main body includes a mating recess;
   a flexible band having a first end, a second end, and a middle portion therebetween, wherein a leader is attached to the first end, an anchor is attached to the second end, and the middle portion is configured to contact bone, wherein the anchor is configured to engage the mating recess, wherein the leader is configured to loop around patient anatomy and pass through the band slot, and wherein the threaded locking member is configured to lock the flexible band in the band clamp; and
   a tensioning instrument configured to provide tension to the flexible band prior to locking the flexible band in the band clamp
   wherein the anchor has a cut to allow the anchor to contact to enter the anchor slot and then expand to be received into the mating recess.

11. The system of claim 10, wherein the leader is configured to pass through the anchor slot until the anchor engages with the mating recess, the leader further configured to wrap around patient anatomy and then be inserted into the band slot to create a loop around the patient anatomy with the middle portion of the flexible band.

12. The system of claim 11, wherein the locking member locks the flexible band to the main body of the band clamp after the leader is passed through the band slot.

13. The system of claim 12, wherein the tensioning instrument is a ratcheting tensioner connected to an instrument assembly.

14. The system of claim 10, wherein the locking member is threaded into the main body of the band clamp.

15. The system of claim 14, wherein the locking member includes a threaded set screw and a saddle.

16. The system of claim 15, wherein the threaded set screw is configured to receive the saddle via a slot in the threaded set screw.

17. The system of claim 16, wherein the saddle engages the flexible band to lock the flexible band in the band clamp.

18. The system of claim 10, wherein the anchor slot is disposed under the band slot.

* * * * *